United States Patent
Wong et al.

(10) Patent No.: US 10,214,765 B2
(45) Date of Patent: *Feb. 26, 2019

(54) CELL-PERMEABLE PROBES FOR IDENTIFICATION AND IMAGING OF SIALIDASES

(71) Applicant: Academina Sinica, Taipei (TW)

(72) Inventors: Chi-Huey Wong, Rancho Santa Fe, CA (US); Jim-Min Fang, Taipei (TW); Yih-Shyun E. Cheng, Taipei (TW); Chamg-Sheng Tsai, New Taipei (TW)

(73) Assignee: Academia Sinica, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/881,581

(22) Filed: Jan. 26, 2018

(65) Prior Publication Data

US 2018/0155761 A1    Jun. 7, 2018

Related U.S. Application Data

(62) Division of application No. 14/422,310, filed as application No. PCT/US2013/055472 on Aug. 16, 2013, now Pat. No. 9,914,956.

(60) Provisional application No. 61/684,751, filed on Aug. 18, 2012.

(51) Int. Cl.
| | |
|---|---|
| C07H 5/00 | (2006.01) |
| C07H 13/04 | (2006.01) |
| C07H 13/12 | (2006.01) |
| C12N 9/24 | (2006.01) |
| C12Q 1/04 | (2006.01) |
| C12Q 1/34 | (2006.01) |
| C12Q 1/40 | (2006.01) |
| C12Q 1/70 | (2006.01) |

(52) U.S. Cl.
CPC ............ C12Q 1/40 (2013.01); C07H 5/00 (2013.01); C07H 13/04 (2013.01); C07H 13/12 (2013.01); C12N 9/2402 (2013.01); C12Q 1/04 (2013.01); C12Q 1/34 (2013.01); C12Q 1/70 (2013.01); *C12Y 302/01018* (2013.01); *G01N 2333/11* (2013.01)

(58) Field of Classification Search
CPC ........ C07H 13/04; C07H 13/12; C07H 5/00; C12Q 1/34; C12Q 1/70; C12Q 1/04; C12Q 1/40; C12N 9/2402; G01N 2333/11
See application file for complete search history.

(56) References Cited

U.S. PATENT DOCUMENTS

| | | |
|---|---|---|
| 3,773,919 A | 11/1973 | Boswell et al. |
| 3,896,111 A | 7/1975 | Kupchan et al. |
| 4,137,230 A | 1/1979 | Hashimoto et al. |
| 4,151,042 A | 4/1979 | Higashide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,270,537 A | 6/1981 | Romaine |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| RE30,985 E | 6/1982 | Cartaya |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,376,110 A | 3/1983 | David et al. |
| 4,419,446 A | 12/1983 | Howley et al. |
| 4,424,219 A | 1/1984 | Hashimoto et al. |
| 4,450,254 A | 5/1984 | Isley et al. |
| 4,560,655 A | 12/1985 | Baker |
| 4,596,556 A | 6/1986 | Morrow et al. |
| 4,596,792 A | 6/1986 | Vyas |
| 4,599,230 A | 7/1986 | Milich et al. |
| 4,599,231 A | 7/1986 | Milich et al. |
| 4,601,903 A | 7/1986 | Frasch |
| 4,601,978 A | 7/1986 | Karin |
| 4,657,866 A | 4/1987 | Kumar |
| 4,676,980 A | 6/1987 | Segal et al. |

(Continued)

FOREIGN PATENT DOCUMENTS

| | | |
|---|---|---|
| EP | 0404097 A2 | 12/1990 |
| EP | 0341735 B1 | 9/1992 |

(Continued)

OTHER PUBLICATIONS

U.S. Appl. No. 15/005,930, filed Jan. 25, 2016, Wong et al.
U.S. Appl. No. 15/011,543, filed Jan. 30, 2016, Wong et al.
U.S. Appl. No. 15/011,544, filed Jan. 30, 2016, Wong et al.
U.S. Appl. No. 15/173,496, filed Jun. 3, 2016, Wong et al.
Abbas et al., "Functional diversity of helper T lymphocytes," *Nature*, Oct. 31, 1996, 383(6603):787-793.
Abrahmsén et al, "Analysis of signals for secretion in the staphylococcal protein A gene," *EMBO J.*, Dec. 30, 1985, 4(13B):3901-3906.

(Continued)

*Primary Examiner* — Lawrence E Crane
(74) *Attorney, Agent, or Firm* — Duane Morris LLP

(57) ABSTRACT

Provided herein are compounds for use as sialidase inhibitors, including alkynyl-3-fluorosialyl fluoride. The compounds, which include the compound DFSA, function by trapping a 3-fluorosialylenzyme intermediate (reporter-inhibitor-enzyme conjugate). These compounds can be conjugated with a detectable tagging moiety for isolation and identification of sialidases.

16 Claims, 12 Drawing Sheets

Specification includes a Sequence Listing.

(56) References Cited

U.S. PATENT DOCUMENTS

| | | |
|---|---|---|
| 4,741,900 A | 5/1988 | Alvarez et al. |
| 4,767,704 A | 8/1988 | Cleveland et al. |
| 4,790,824 A | 12/1988 | Morrow et al. |
| 4,816,567 A | 3/1989 | Cabilly et al. |
| 4,849,222 A | 7/1989 | Broaddus |
| 4,886,499 A | 12/1989 | Cirelli et al. |
| 4,927,762 A | 5/1990 | Darfler |
| 4,940,460 A | 7/1990 | Casey et al. |
| 4,941,880 A | 7/1990 | Burns |
| 4,965,199 A | 10/1990 | Capon et al. |
| 4,970,198 A | 11/1990 | Lee et al. |
| 4,975,278 A | 12/1990 | Senter et al. |
| 5,004,697 A | 4/1991 | Pardridge |
| 5,015,235 A | 5/1991 | Crossman |
| 5,053,394 A | 10/1991 | Ellestad et al. |
| 5,061,620 A | 10/1991 | Tsukamoto et al. |
| 5,064,413 A | 11/1991 | McKinnon et al. |
| 5,075,109 A | 12/1991 | Tice et al. |
| 5,079,233 A | 1/1992 | Lee |
| 5,100,669 A | 3/1992 | Hyon et al. |
| 5,112,596 A | 5/1992 | Malfroy-Camine |
| 5,122,469 A | 6/1992 | Mather et al. |
| 5,141,496 A | 8/1992 | Dalto et al. |
| 5,190,521 A | 3/1993 | Hubbard et al. |
| 5,208,020 A | 5/1993 | Chari et al. |
| 5,229,275 A | 7/1993 | Goroff |
| 5,264,365 A | 11/1993 | Georgiou et al. |
| 5,268,164 A | 12/1993 | Kozarich et al. |
| 5,312,335 A | 5/1994 | McKinnon et al. |
| 5,326,856 A | 7/1994 | Coughlin et al. |
| 5,328,483 A | 7/1994 | Jacoby |
| 5,334,144 A | 8/1994 | Alchas et al. |
| 5,339,163 A | 8/1994 | Homma et al. |
| 5,362,852 A | 11/1994 | Geoghegan |
| 5,369,017 A | 11/1994 | Wong et al. |
| 5,374,541 A | 12/1994 | Wong et al. |
| 5,383,851 A | 1/1995 | McKinnon, Jr. et al. |
| 5,395,541 A | 3/1995 | Carpenter et al. |
| 5,416,064 A | 5/1995 | Chari et al. |
| 5,417,662 A | 5/1995 | Hjertman et al. |
| 5,466,220 A | 11/1995 | Brenneman |
| 5,480,381 A | 1/1996 | Weston |
| 5,500,362 A | 3/1996 | Robinson et al. |
| 5,503,627 A | 4/1996 | McKinnon et al. |
| 5,506,206 A | 4/1996 | Kozarich et al. |
| 5,508,192 A | 4/1996 | Georgiou et al. |
| 5,518,725 A | 5/1996 | Daynes et al. |
| 5,520,639 A | 5/1996 | Peterson et al. |
| 5,527,288 A | 6/1996 | Gross et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,189 A | 10/1996 | Parsons |
| 5,569,825 A | 10/1996 | Lonberg et al. |
| 5,571,894 A | 11/1996 | Wels et al. |
| 5,580,717 A | 12/1996 | Dower et al. |
| 5,585,089 A | 12/1996 | Queen et al. |
| 5,587,458 A | 12/1996 | King et al. |
| 5,591,669 A | 1/1997 | Krimpenfort et al. |
| 5,591,828 A | 1/1997 | Bosslet et al. |
| 5,599,302 A | 2/1997 | Lilley et al. |
| 5,606,040 A | 2/1997 | McGahren et al. |
| 5,624,821 A | 4/1997 | Winter et al. |
| 5,625,126 A | 4/1997 | Lonberg et al. |
| 5,633,425 A | 5/1997 | Lonberg et al. |
| 5,635,483 A | 6/1997 | Pettit et al. |
| 5,639,635 A | 6/1997 | Joly et al. |
| 5,641,870 A | 6/1997 | Rinderknecht et al. |
| 5,643,577 A | 7/1997 | Pang et al. |
| 5,648,237 A | 7/1997 | Carter |
| 5,648,260 A | 7/1997 | Winter et al. |
| 5,649,912 A | 7/1997 | Peterson |
| 5,661,016 A | 8/1997 | Lonberg et al. |
| 5,663,149 A | 9/1997 | Pettit et al. |
| 5,674,988 A | 10/1997 | Sabesan |
| 5,677,180 A | 10/1997 | Robinson et al. |
| 5,686,416 A | 11/1997 | Kozarich et al. |
| 5,690,938 A | 11/1997 | Ermak et al. |
| 5,693,762 A | 12/1997 | Queen et al. |
| 5,704,911 A | 1/1998 | Parsons |
| 5,712,374 A | 1/1998 | Kuntsman et al. |
| 5,714,374 A | 2/1998 | Arnold et al. |
| 5,714,586 A | 2/1998 | Kunstman et al. |
| 5,731,168 A | 3/1998 | Cater et al. |
| 5,733,743 A | 3/1998 | Johnson et al. |
| 5,736,137 A | 4/1998 | Anderson et al. |
| 5,739,116 A | 4/1998 | Hamann et al. |
| 5,767,285 A | 6/1998 | Hamann et al. |
| 5,770,701 A | 6/1998 | McGahren et al. |
| 5,773,001 A | 6/1998 | Hamann et al. |
| 5,780,588 A | 7/1998 | Pettit et al. |
| 5,814,344 A | 9/1998 | Tice et al. |
| 5,820,883 A | 10/1998 | Tice et al. |
| 5,821,337 A | 10/1998 | Carter et al. |
| 5,837,234 A | 11/1998 | Gentile et al. |
| 5,840,523 A | 11/1998 | Simmons et al. |
| 5,849,716 A | 12/1998 | Akimoto |
| 5,853,763 A | 12/1998 | Tice et al. |
| 5,869,046 A | 2/1999 | Presta et al. |
| 5,877,296 A | 3/1999 | Hamann et al. |
| 5,893,397 A | 4/1999 | Peterson et al. |
| 5,993,412 A | 11/1999 | Deily et al. |
| 6,004,940 A | 12/1999 | Marasco et al. |
| 6,027,888 A | 2/2000 | Georgiou et al. |
| 6,083,715 A | 7/2000 | Georgiou et al. |
| 6,111,132 A | 8/2000 | Kim et al. |
| 6,143,724 A | 11/2000 | Ohira et al. |
| 6,210,670 B1 | 4/2001 | Berg |
| 6,265,150 B1 | 7/2001 | Terstappen et al. |
| 6,329,173 B1 | 12/2001 | Marasco et al. |
| 6,340,702 B1 | 1/2002 | Honda et al. |
| 6,399,071 B1 | 6/2002 | Duthaler |
| 6,455,571 B1 | 9/2002 | Maring et al. |
| 6,506,564 B1 | 1/2003 | Mirkin et al. |
| 6,528,286 B1 | 3/2003 | Ryll |
| 6,548,476 B1 | 4/2003 | Wu et al. |
| 6,680,054 B1 | 1/2004 | Reece et al. |
| 6,696,304 B1 | 2/2004 | Davies |
| 6,703,019 B1 | 3/2004 | Malfroy-Camine |
| 6,824,780 B1 | 11/2004 | Devaux et al. |
| 6,855,551 B2 | 2/2005 | Bawendi et al. |
| 6,873,914 B2 | 3/2005 | Winfield et al. |
| 6,984,630 B1 | 1/2006 | Descamps et al. |
| 6,994,966 B2 | 2/2006 | Dukler |
| 7,019,288 B2 | 3/2006 | Becker |
| 7,090,973 B1 | 8/2006 | Breton |
| 7,151,164 B2 | 12/2006 | Hansen et al. |
| 7,157,433 B2 | 1/2007 | Mercep et al. |
| 7,205,333 B2 | 4/2007 | Wu et al. |
| 7,488,491 B2 | 2/2009 | Tsjui et al. |
| 7,498,298 B2 | 3/2009 | Doronina et al. |
| 7,854,934 B2 | 12/2010 | Danishefsky |
| 7,888,337 B2 | 2/2011 | Wong et al. |
| 7,923,013 B2 | 4/2011 | Tsuji et al. |
| 7,928,077 B2 | 4/2011 | Wong et al. |
| 7,943,330 B2 | 5/2011 | Wong et al. |
| 7,960,139 B2 | 6/2011 | Sawa et al. |
| 7,977,097 B1 | 7/2011 | Gay et al. |
| 8,022,043 B2 | 9/2011 | Porcelli |
| 8,088,387 B2 | 1/2012 | Steeves et al. |
| 8,101,179 B2 | 1/2012 | Numazaki et al. |
| 8,268,969 B2 | 9/2012 | Wong et al. |
| 8,383,554 B2 | 2/2013 | Wong et al. |
| 8,507,660 B2 | 8/2013 | Wong et al. |
| 8,680,020 B2 | 3/2014 | Wong et al. |
| 8,716,465 B2 | 5/2014 | Rossi et al. |
| 8,802,438 B2 | 8/2014 | Rossi et al. |
| 8,815,941 B2 | 8/2014 | Withers |
| 8,883,506 B2 | 11/2014 | Rossi et al. |
| 8,906,832 B2 | 12/2014 | Wong et al. |
| 8,907,111 B2 | 12/2014 | Withers |
| 9,187,552 B2 | 11/2015 | Stadheim |
| 9,221,859 B2 | 12/2015 | Withers |

(56) References Cited

U.S. PATENT DOCUMENTS

| | | | |
|---|---|---|---|
| 9,382,284 B2 | 7/2016 | Withers | |
| 9,434,786 B2 | 9/2016 | Wang | |
| 9,759,726 B2 * | 9/2017 | Wong | C07D 309/14 |
| 9,803,177 B2 | 10/2017 | Rossi et al. | |
| 9,914,956 B2 * | 3/2018 | Wong | C12Q 1/40 |
| 2002/0025313 A1 | 2/2002 | Micklus et al. | |
| 2002/0038086 A1 | 3/2002 | Hynynen et al. | |
| 2002/0065259 A1 | 5/2002 | Schatzberg et al. | |
| 2003/0073713 A1 | 4/2003 | Schoenhard | |
| 2003/0083299 A1 | 5/2003 | Ferguson | |
| 2003/0104402 A1 | 6/2003 | Zauderer et al. | |
| 2003/0118592 A1 | 6/2003 | Ledbetter et al. | |
| 2003/0129186 A1 | 7/2003 | Beliveau et al. | |
| 2003/0162695 A1 | 8/2003 | Schatzberg et al. | |
| 2003/0175884 A1 | 9/2003 | Umana et al. | |
| 2003/0219433 A1 | 11/2003 | Hansen et al. | |
| 2004/0072290 A1 | 4/2004 | Umana et al. | |
| 2004/0086423 A1 | 5/2004 | Wohlstadter | |
| 2004/0131692 A1 | 7/2004 | Kreuter et al. | |
| 2004/0137557 A1 | 7/2004 | DeFrees et al. | |
| 2004/0204354 A1 | 10/2004 | Nelson et al. | |
| 2004/0259142 A1 | 12/2004 | Chai et al. | |
| 2005/0085413 A1 | 4/2005 | Jin et al. | |
| 2005/0089473 A1 | 4/2005 | Black et al. | |
| 2005/0106108 A1 | 5/2005 | Hansen et al. | |
| 2005/0123546 A1 | 6/2005 | Umana et al. | |
| 2005/0124533 A1 | 6/2005 | Schatzberg et al. | |
| 2005/0221337 A1 | 10/2005 | Seeberger et al. | |
| 2005/0221397 A1 | 10/2005 | Saito | |
| 2005/0255491 A1 | 11/2005 | Lee | |
| 2006/0019256 A1 | 1/2006 | Clarke et al. | |
| 2006/0073122 A1 | 4/2006 | Koezuka et al. | |
| 2006/0073161 A1 | 4/2006 | Breton | |
| 2006/0211856 A1 | 9/2006 | Tsuji et al. | |
| 2006/0286140 A1 | 12/2006 | Wickstrom et al. | |
| 2006/0286637 A1 | 12/2006 | Hamilton | |
| 2007/0059769 A1 | 3/2007 | Blixt et al. | |
| 2007/0065949 A1 | 3/2007 | Hutchens | |
| 2007/0207090 A1 | 9/2007 | Giudice | |
| 2007/0213278 A1 | 9/2007 | Wong et al. | |
| 2007/0219351 A1 | 9/2007 | Fiume et al. | |
| 2007/0224189 A1 | 9/2007 | Lazar et al. | |
| 2007/0238871 A1 | 10/2007 | Tsuji et al. | |
| 2008/0070324 A1 | 3/2008 | Floyd | |
| 2008/0220988 A1 | 9/2008 | Zhou | |
| 2008/0260774 A1 | 10/2008 | Wong et al. | |
| 2009/0035179 A1 | 2/2009 | Rakow et al. | |
| 2009/0081255 A1 | 3/2009 | Bublot et al. | |
| 2009/0123439 A1 | 5/2009 | Yun et al. | |
| 2009/0285837 A1 | 11/2009 | Kao et al. | |
| 2009/0298797 A1 | 12/2009 | Zheng et al. | |
| 2009/0317837 A1 | 12/2009 | Wong et al. | |
| 2010/0009339 A1 | 1/2010 | Bovin et al. | |
| 2010/0022026 A1 | 1/2010 | Rump et al. | |
| 2010/0047827 A1 | 2/2010 | Laine et al. | |
| 2010/0047828 A1 | 2/2010 | Sorenson et al. | |
| 2010/0068806 A1 | 3/2010 | Laine et al. | |
| 2010/0112195 A1 | 5/2010 | Kodas et al. | |
| 2010/0113397 A1 | 5/2010 | Wong et al. | |
| 2010/0136009 A1 | 6/2010 | Papkoff et al. | |
| 2010/0136042 A1 | 6/2010 | Wong et al. | |
| 2010/0173323 A1 | 7/2010 | Strome | |
| 2011/0086408 A1 | 4/2011 | Power | |
| 2011/0104188 A1 | 5/2011 | Tashiro et al. | |
| 2011/0124116 A1 | 5/2011 | Wohlstadter et al. | |
| 2011/0137570 A1 | 6/2011 | Lapadula et al. | |
| 2011/0237459 A1 | 9/2011 | Nova et al. | |
| 2011/0263828 A1 | 10/2011 | Wong et al. | |
| 2012/0046346 A1 | 2/2012 | Rossi et al. | |
| 2012/0171201 A1 | 7/2012 | Sapra | |
| 2012/0178705 A1 | 7/2012 | Liang et al. | |
| 2012/0178802 A1 | 7/2012 | Withers et al. | |
| 2012/0226024 A1 | 9/2012 | Wang et al. | |
| 2012/0294859 A1 | 11/2012 | Goletz et al. | |
| 2012/0322864 A1 | 12/2012 | Rossi et al. | |
| 2012/0322865 A1 | 12/2012 | Rossi et al. | |
| 2012/0328646 A1 | 12/2012 | Wong et al. | |
| 2013/0189258 A1 | 7/2013 | Rother et al. | |
| 2013/0196356 A1 | 8/2013 | Jackson et al. | |
| 2013/0230886 A1 | 9/2013 | Votsmeier et al. | |
| 2013/0295104 A1 | 11/2013 | Deckert et al. | |
| 2013/0337018 A1 | 12/2013 | Fox | |
| 2014/0051127 A1 | 2/2014 | Wong et al. | |
| 2014/0086916 A1 | 3/2014 | Zha | |
| 2014/0127241 A1 | 5/2014 | Leuschner et al. | |
| 2014/0178365 A1 | 6/2014 | Ghaderi et al. | |
| 2014/0302028 A1 | 10/2014 | Zha | |
| 2014/0308746 A1 | 10/2014 | Rossi et al. | |
| 2015/0087814 A1 | 3/2015 | Wang | |
| 2015/0160217 A1 | 6/2015 | Wong et al. | |
| 2015/0225766 A1 | 8/2015 | Wong et al. | |
| 2015/0309041 A1 | 10/2015 | Wong et al. | |
| 2015/0344544 A1 | 12/2015 | Wong et al. | |
| 2015/0344551 A1 | 12/2015 | Wong et al. | |
| 2015/0344559 A1 | 12/2015 | Wong et al. | |
| 2015/0344585 A1 | 12/2015 | Wong et al. | |
| 2015/0344587 A1 | 12/2015 | Wong et al. | |
| 2016/0009803 A1 | 1/2016 | Rother et al. | |
| 2016/0102151 A1 | 4/2016 | Wong et al. | |
| 2016/0215061 A1 | 7/2016 | Shaeen | |
| 2016/0274121 A1 | 9/2016 | Wong et al. | |
| 2016/0280794 A1 | 9/2016 | Wong et al. | |
| 2016/0289340 A1 | 10/2016 | Wong et al. | |
| 2017/0275389 A1 | 9/2017 | Wong et al. | |
| 2017/0283878 A1 | 10/2017 | Wong et al. | |

FOREIGN PATENT DOCUMENTS

| | | |
|---|---|---|
| EP | 0425235 B1 | 9/1996 |
| EP | 1208909 A2 | 5/2002 |
| EP | 1391213 A1 | 2/2004 |
| EP | 2123271 | 11/2009 |
| EP | 2187217 A1 | 5/2010 |
| JP | 05-222085 | 8/1993 |
| JP | 05-507068 | 10/1993 |
| JP | 05-339283 A | 12/1993 |
| JP | 11-343295 A | 12/1999 |
| JP | 2005-06008 | 5/2000 |
| WO | WO 87/00195 A1 | 1/1987 |
| WO | WO 90/03430 A1 | 4/1990 |
| WO | WO 91/00360 A1 | 1/1991 |
| WO | WO 91/10741 A1 | 7/1991 |
| WO | WO 92/00373 A1 | 1/1992 |
| WO | WO 92/006691 | 4/1992 |
| WO | WO 92/09690 A2 | 6/1992 |
| WO | WO 93/01161 A1 | 1/1993 |
| WO | WO 93/06213 A1 | 4/1993 |
| WO | WO 93/07861 A1 | 4/1993 |
| WO | WO 93/08829 A1 | 5/1993 |
| WO | WO 93/09764 | 5/1993 |
| WO | WO 93/16185 A2 | 8/1993 |
| WO | WO 93/021232 A1 | 10/1993 |
| WO | WO 94/04690 A1 | 3/1994 |
| WO | WO 94/11026 | 5/1994 |
| WO | WO 94/29351 | 12/1994 |
| WO | WO 95/11010 A1 | 4/1995 |
| WO | WO 96/07754 A1 | 3/1996 |
| WO | WO 96/16673 A1 | 6/1996 |
| WO | WO 96/33735 A1 | 10/1996 |
| WO | WO 96/34096 A1 | 10/1996 |
| WO | WO 97/05267 A2 | 2/1997 |
| WO | WO 97/013537 | 4/1997 |
| WO | WO 97/17852 A1 | 5/1997 |
| WO | WO 97/037705 | 10/1997 |
| WO | WO 98/00558 A1 | 1/1998 |
| WO | WO 98/02463 A1 | 1/1998 |
| WO | WO 98/24893 A2 | 6/1998 |
| WO | WO 99/034850 | 7/1999 |
| WO | WO 99/49019 A2 | 9/1999 |
| WO | WO 99/051642 | 10/1999 |
| WO | WO 99/057134 A1 | 11/1999 |
| WO | WO 01/42505 A2 | 6/2001 |
| WO | WO 01/86001 A1 | 11/2001 |
| WO | WO 02/088172 | 11/2002 |

(56) References Cited

FOREIGN PATENT DOCUMENTS

| WO | WO 03/040104 A1 | 5/2003 |
|---|---|---|
| WO | WO 03/68821 A2 | 8/2003 |
| WO | WO 03/077945 A1 | 9/2003 |
| WO | WO 2004/035607 A2 | 4/2004 |
| WO | WO 2004/056312 A2 | 7/2004 |
| WO | WO 2004/063351 | 7/2004 |
| WO | WO 2004/103404 A1 | 12/2004 |
| WO | WO 2005/030258 A2 | 4/2005 |
| WO | WO 2005/044859 | 5/2005 |
| WO | WO 2005/088310 A2 | 9/2005 |
| WO | WO 2005/103081 A2 | 11/2005 |
| WO | WO 2006/055925 A2 | 5/2006 |
| WO | WO 2006/064983 A1 | 6/2006 |
| WO | WO 2006/106959 | 10/2006 |
| WO | WO 2006/126069 A2 | 11/2006 |
| WO | WO 2006/130458 A2 | 12/2006 |
| WO | WO 2007/078873 A1 | 7/2007 |
| WO | WO 2007/0133855 | 11/2007 |
| WO | WO 2007/146847 A2 | 12/2007 |
| WO | WO 2008/020596 A2 | 2/2008 |
| WO | WO 2008/087260 A1 | 7/2008 |
| WO | WO 2008/118013 | 10/2008 |
| WO | WO 2008/133801 A1 | 11/2008 |
| WO | WO 2008/0133857 A1 | 11/2008 |
| WO | WO 2009/029888 A3 | 3/2009 |
| WO | WO 2010/006315 A2 | 1/2010 |
| WO | WO 2010/009271 A1 | 1/2010 |
| WO | WO 2010/011703 | 1/2010 |
| WO | WO-2010/029302 A2 | 3/2010 |
| WO | WO 2011/005756 A1 | 1/2011 |
| WO | WO 2011/006237 A1 | 1/2011 |
| WO | WO 2011/031236 A1 | 3/2011 |
| WO | WO 2011/074621 A1 | 6/2011 |
| WO | WO 2011/089004 A1 | 7/2011 |
| WO | WO 2011/130332 | 10/2011 |
| WO | WO 2011/143262 A2 | 11/2011 |
| WO | WO 2011/145957 A1 | 11/2011 |
| WO | WO 2012/082635 A1 | 6/2012 |
| WO | WO 2012/094540 A2 | 7/2012 |
| WO | WO 2013/011347 A1 | 1/2013 |
| WO | WO 2013/024895 A1 | 2/2013 |
| WO | WO 2013/088395 A1 | 6/2013 |
| WO | WO-2013/106937 A1 | 7/2013 |
| WO | WO 2013/120066 A1 | 8/2013 |
| WO | WO 2013/130603 A1 | 9/2013 |
| WO | WO 2013/152034 A1 | 10/2013 |
| WO | WO 2013/155375 A1 | 10/2013 |
| WO | WO 2013/181585 A2 | 12/2013 |
| WO | WO 2014/031498 | 2/2014 |
| WO | WO 2014/078373 A1 | 5/2014 |
| WO | WO 2014/210397 A1 | 12/2014 |
| WO | WO 2014/210564 | 12/2014 |
| WO | WO 2015/026484 A1 | 2/2015 |
| WO | WO 2015/035337 A1 | 3/2015 |
| WO | WO 2015/038963 A1 | 3/2015 |
| WO | WO 2015/184008 | 12/2015 |
| WO | WO 2016/040369 A2 | 3/2016 |
| WO | WO 2016-118090 A1 | 7/2016 |
| WO | WO 2014/031762 A1 | 2/2017 |

OTHER PUBLICATIONS

Achtman, M., Epidemic Spread and Antigenic Variability of Neisseria Meningitidis, Trends Microbial 1995, 3, 186-192.
Adam et al., "Proteomic profiling of mechanistically distinct enzyme classes using a common chemotype," *Nat. Biotechnol.*, Aug. 2002, 20(8):805-809.
Agard, N. et al., A Strain-Promoted [3+2]Azide-Alkyne Cycloaddition for Covalent Modification of Biomolecules in Living Systems, J. Am. Chem. Soc. 2004, 126, 15046-15047.
Ahmadi, T. S. et al., Shape-Controlled Synthesis of Colloidal Platinum Nanoparticles, Science, 272, 1924 (1996).
Ahmed et al.,Structural Characterization of Anti-Inflammatory Immunoglobulin G Fc Proteins, K Mol Biol (2014) 426, 3166-3179.
Altevogt, Peter et al., Different Patterns of Lectin Binding and Cell Surface Sialylation Detected on Related High- and Low-Metastatic Tumor Lines, Cancer Res. 43, 5138-5144, 1983.
Altschul SF et al., "Basic local alignment search tool", *J Mol Biol*. Oct. 5, 1990;215(3):403-10.
Altschul SF, et al., "Gapped BLAST and PSI-BLAST: a new generation of protein database search programs", *Nucleic Acids Res*. Sep. 1, 1997;25(17):3389-402.
Amin, M. N. et al. Synthetic glycopeptides reveal the glycan specificity of HIV-neutralizing antibodies. Nat. Chem. Biol. 9, 521-526, (2013).
Anderson et al., "Stimulation of Natural Killer T Cells by Glycolipids", *Molecules*, May 2013, 18(12), 15662-15688.
Andrews et al., Synthesis and influenza virus sialidase inhibitory activity of analogues of 4-Guanidino-Neu5Ac2en (Zanamivir modified in the glycerol side-chain. Eur J Med Chem Jul.-Aug. 1999;34(7-8):563-74.
Angata et al., "Chemical diversity in the sialic acids and related α-keto acids: an evolutionary perspective," *Chem. Rev.*, Feb. 2002, 102(2):439-469.
Anthony, Robert et al., Recapitulation of IVIG Anti-Inflammatory Activity with a Recombinant IgG Fc, Science Apr. 18, 2008. 320:373-376.
Arase et al., "NK1.1$^+$ CD4$^+$ CD8$^-$ thymocytes with specific lymphokine secretion," *Eur. J. Immunol.*, Jan. 1993, 23(1):307-310.
Arié et al., "Chaperone function of FkpA, a heat shock prolyl isomerase, in the periplasm of *Escherichia coli*," *Mol. Microbiol.*, Jan. 2001, 39(1):199-210.
Aspeslagh et al., "Galactose-modified iNKT cell agonists stabilized by an induced fit of CD1d prevent tumour metastasis," *EMBO J.*, Jun. 1, 2011, 30(11):2294-2305.
Astronomo, R. D. & Burton, D.R. Carbohydrate vaccines: developing sweet solutions to sticky situations? Nat. Rev. Drug. Discov. 9, 308-324, (2010).
Bachmann, *Cellular and Molecular Biology, vol. 2, Chapter 72: Derivations and Genotypes of Some Mutant Derivatives of Escherichia coli K-12*, Neidhardt et al., eds., 1987, pp. 1190-1219, American Society for Microbiology, Washington, D.C.
Bacilieri, Magdalena et al., Ligand-Based Drug Design Methodologies in Drug Discovery Process: An Overview, Current Drug Discovery Technologies, vol. 3 (3), Sep. 2006, p. 155-165.
Bacteroides Fragilis NCTC 9343, Complete Genome., Mar. 3, 2005, XP002775523, Database Accession No. CR626927, 2 Pages.
Bacteroides Thetaiotaomicron VPI-5482, Section 8 of 21 of the Complete Genome, XP002775522, Jan. 6, 2006, Database Accession No. AE016933, 2 Pages.
Bai, Dan et al., Exploring Forster Electronic Energy Transfer in a Decoupled Anthracenyl-based Borondipyrromethene (Bodipy) Dyad, Physical Chemistry Chemical Physics (2012), 14(13), 4447-4456.
Bailey, Ryan et al., Real-Time Multicolor DNA Detection with Chemoresponsive Diffraction Gratings and Nanoparticle Probes, J. Am Chem. Soc., 2003, 125, 13541-13547.
Baldwin et al., "Monoclonal antibodies in cancer treatment," *Lancet*, Mar. 15, 1986, 327(8481):603-605.
Banchereau et al., "Dendritic cells and the control of immunity," *Nature*, Mar. 19, 1998, 392(6673):245-252.
Barbas et al., "Assembly of combinatorial antibody libraries on phage surfaces: the gene III site," *Proc. Natl. Acad. Sci. U.S.A.*, Sep. 15, 1991, 88(18):7978-7982.
Barbas et al., "In vitro evolution of a neutralizing human antibody to human immunodeficiency virus type 1 to enhance affinity and broaden strain cross-reactivity," *Proc. Nat. Acad. Sci. U.S.A.*, Apr. 26, 1994, 91(9):3809-3813.
Barbas et al., "Semisynthetic combinatorial antibody libraries: a chemical solution to the diversity problem," *Proc. Natl. Acad. Sci. U.S.A.*, May 15, 1992, 89(10):4457-4461.
Bardotti, Angela et al., Size Determination of Bacterial Capsular Oligosaccharides Used to Prepare Conjugated Vaccines Against Neisseria Meningitidis Groups Y and W135, Vaccine 2005, 23, 1887-1899.
Barnes et al., "Methods for growth of cultured cells in serum-free medium," *Anal. Biochem.*, Mar. 1, 1980, 102(2):255-270.

(56) References Cited

OTHER PUBLICATIONS

Barouch, D. H. Challenges in the development of an HIV-I vaccine. Nature 455, 613-619, (2008).
Barry, C.S. et al., 'Naked' and Hydrated Confirmers of the Conserved Core Pentasaccharide of N-Linked Glycoproteins and Its Building Blocks, Journal of the American Chemical Society, 2013, vol. 135(45), p. 16895-16903.
Basak et al., In Vitro Elucidation of Substrate Specificity and Bioassay of Proprotein Convertase 4 Using Intramolecularly Quenched Fluorogenic Peptides, Biochem. J. Jun. 1, 2004, 380(pt 2): 505-514.
Baselga J, et al., "Phase II study of weekly intravenous recombinant humanized anti-p185HER2 monoclonal antibody in patients with HER2/neu-overexpressing metastatic breast cancer", *J Clin Oncol.* Mar. 1996;14(3):737-44.
Baskin, J.M.; Amacher, S. L.; Bertozzi, C.R."In vivo imaging of membraneassociated glycans in developing zebrafish." Science 2008, 320, 664-667.
Bass et al., "Hormone phage: an enrichment method for variant proteins with altered binding properties," *Proteins*, 1990, 8(4):309-314.
Bassell, G.J. et al., Single mRNAs Visualized by Ultrastructural in Situ Hybridization are Principally Localized at Actin Filament Intersections in Fibroblasts, J. Cell Biol., 126, 863-876 (1994.
Baz et al., Emergence of oseltamivir-resistant pandemic H1N1 virus during prophylaxis. N Engl J Med. Dec. 3, 2009;361(23):2296-7. doi: 10.1056/NEJMc0910060. Epub Nov. 11, 2009.
Beck A., "Biosimilar, biobetter and next generation therapeutic antibodies" *MAbs.* Mar.-Apr. 2011;3(2):107-10. Epub Mar. 1, 2011.
Beckman et al., Antibody constructs in cancer therapy: protein engineering strategies to improve exposure in solid tumors, cancer, 109(2): 170-179 (2007).
Bendayan, Moise, Possibilities of False Immunocytochemical Results Generated by the Use of Momoclonal Antibodies: The Example of the Anti-Proinsulin Antibody, J. Histochem. Cytochem, 43: 881-886, (1995).
Bennett, Clay et al., Chemoenzymatic Approaches to Glycoprotein Synthesis, Chem. Soc. Rev. 2007, 36:1227-1238.
Berg, Jan-Olof et al., Purification of Glycoside Hydrolases From Bacteroides Fragilis, Applied and Environmental Microbiology, vol. 40, No. 1, Jul. 1980, p. 40-47.
Berge, Steven et al. J. Pharmaceutical Sciences (1977) 66: 1-19.
Berra et al., "Correlation between ganglioside distribution and histological grading of human astrocytomas," *Int. J. Cancer*, Sep. 15, 1985, 36(3):363-366.
Best, M. D. "Click chemistry and bioorthogonal reactions: unprecedented selectivity in the labeling of biological molecules." Biochemistry 2009, 48, 6571-6584.
Bertozzi, CR et al., Glycans in Cancer and Inflammation—Potential for Therapeutics and Diagnostics, Nat Rev Drug Discovery, 2005, 4, 477-488.
Bigi et al., "Human sialidase NEU4 long and short are extrinsic proteins bound to outer mitochondrial membrane and the endoplasmic reticulum, respectively," *Glycobiology*, Feb. 2010, 20(2):148-157.
Birklé et al., "Role of tumor-associated gangliosides in cancer progression," *Biochimie*, Mar.-Apr. 2003, 85(3-4):455-463.
Blixt, O. et al. Printed covalent glycan array for ligand profiling of diverse glycan binding proteins. Proc. Natl. Acad. Sci. U.S. A. 101, 17033-17038, (2004.
Bobo et al., "Convection-enhanced delivery of macromolecules in the brain," *Proc. Natl. Acad. Sci. U.S.A.*, Mar. 15, 1994, 91(6) 2076-2080.
Boens, N. et al., "Fluorescent indicators based on BODIPY." Chem. Soc. Rev. 2012, 41, 1130-1172.
Boerner et al., "Production of antigen-specific human monoclonal antibodies from in vitro-primed human splenocytes," *J. Immunol.*, Jul. 1, 1991, 147(1):86-95.
Borg et al., "CD1d-lipid-antigen recognition by the semi-invariant NKT T-cell receptor," *Nature*, Jul. 5, 2007, 448(7149):44-49.

Bosmann et al., "Enzyme activity in invasive tumors of human breast and colon," *Proc. Natl. Acad. Sci. USA*, May 1974, 71(5):1833-1837.
Bost, Kenneth et al., Antibodies Against a Peptide Sequence Within the HIV Envelope Protein Crossreacts With Human Interleukin-2, Immunol. Invest., 17: 577-586 (1988).
Bothmann et al., "The periplasmic *Escherichia coli* peptidylprolyl cis,trans-isomerase FkpA. I. Increased functional expression of antibody fragments with and without cis-prolines," *J. Biol. Chem.*, Jun. 2, 2000, 275(22):17100-17105.
Boyer, David et al., Photothermal Imaging of Nanometer-Sized Metal Particles Among Scatterers, Science, 2002, 297, 1160-116 3.
Braun-Howland et al., Development of a Rapid Method for Detecting Bacterial Cell In Situ Using 16S rRNA-Targeted Probes, Biotechniques, 13, 928-931 (1992).
Brennan et al., "Preparation of bispecific antibodies by chemical recombination of monoclonal immunoglobulin $G_1$ fragments," *Science*, Jul. 5, 1985, 229(4708):81-83.
Bricard et al., "Enrichment of human $CD4^+$ $V\alpha24/V\beta11$ invariant NKT cells in intrahepatic malignant tumors," *J. Immunol.*, Apr. 15, 2009, 182(2):5140-5151.
Brimble et al., "The cell surface glycosphingolipids SSEA-3 and SSEA-4 are not essential for human ESC pluripotency," *Stem Cells*, Jan. 2007, 25(1):54-62.
Brodeur et al., *Monoclonal Antibody Production Techniques and Applications*, Chapter 4: Mouse-Human Myeloma Partners for the Production of Heterohybridomas, Schook, ed., 1987, pp. 51-63, Marcel Dekker, Inc., New York.
Bruchez, Marcel et al. Semiconductor Nanocrystals as Fluorescent Biological Labels, Science 281:2013-2016, 1998.
Brüggemann et al., "Designer mice: the production of human antibody repertoires in transgenic animals," *Year in Immunol.*, 1993, 7:33-40.
Buchini et al., "Towards a new generation of specific *Trypanosoma cruzi* trans-sialidase inhibitors," *Angew. Chem. Int. Ed. Engl.*, 2008, 47(14):2700-2703.
Burton, D.R., Mascola, J. R. Antibody responses to envelope glycoproteins in HIV-I infection. Nature Immunol. 16, 571-6, (2015).
Calarese, D. A. et al. Antibody domain exchange is an immunological solution to carbohydrate cluster recognition. Science 300, 2065-2071, (2003).
Cao, Y. C. et al., Nanoparticles with Raman Spectroscopic Fingerprints for DNA and RNA Detection, Science, 2002, 289, 1757-60.
Capel PJ et al., "Heterogeneity of human IgG Fc receptors" *Immunomethods*. Feb. 1994;4(1):25-34.
Carlsson, Jan et al., Protein Thiolation and Reversible Protein-Protein Conjugation, Biochem J 173: 723-737 (1978).
Carter et al., "High level *Escherichia coli* expression and production of a bivalent humanized antibody fragment," *Nature Biotechnology*, Feb. 1992, 10(2):163-167.
Carter et al., "Humanization of an anti-p185$^{HER2}$ antibody for human cancer therapy," *Proc. Natl. Acad. Sci. U.S.A.*, May 15, 1992, 89(10):4285-4289.
Carter PJ. "Potent antibody therapeutics by design" *Nat Rev Immunol.* May 2006;6(5):343-357.
Carter, A rationale for using steroids in the treatment of severe cases of H5N1 avian influenza. J Med Microbiol. Jul. 2007;56(Pt 7):875-83.
Centers for Disease Control and Prevention (CDC), "Influenza activity—United States and worldwide, 2007-08 season" *MMWR*, Jun. 27, 2008, 57(25):692-697.
Cespedes et al., Mouse models in oncogenesis and cancer therapy, Clin Transl Oncl., 8(5): 318-329 (2006).
Chan, Warren et al., Quantum Dot Bioconjugates for Ultrasensitive Nonisotopic Detection, Science 281:2016-2018 (1998).
Chandler et al., Synthesis of the potent influenza neuraminidase inhibitor 5-guanidino Neu5Ac2en. X-Ray molecular structure of 5-acetaminido-4amino-2,6-anahydro-3,4,5-tryoxy-D-erythoro-L-gluco-nononic acid. J Chem Soc Perkin Trans 1. 1995; 1173-1180.

(56) References Cited

OTHER PUBLICATIONS

Chang et al., "Expression of Globo H and SSEA3 in breast cancer stem cells and the involvement of fucosyl transferases 1 and 2 in Globo H synthesis," Proc. Natl. Acad. Sci. U.S.A., Aug. 19, 2008, 105(33):11667-11672.
Chang, S. H. et al. Glycan array on aluminum oxide-coated glass slides through phosphonate chemistry. J. Am. Chem. Soc. 132, 13371-13380, (2010).
Chang et al., "Potent immune-modulating and anticancer effects of NKT cell stimulatory glycolipids," Proc. Natl. Acad. Sci. USA, Jun. 19, 2007, 104(25):10299-10304.
Chao, W.; Fang, X.; Nisaraporn, S.; Jian, S.; Qian, W. "Tuning the optical properties of BODIPY dye through Cu(I) catalyzed azide-alkyne cycloaddition (CuAAC) reaction." Sci. China Chemistry 2012, 55, 125-130.
Chari, Ravi et al., Immunoconjuates Containing Novel Maytansinoids: Promising Anticancer Drugs Cancer Research 52: 127-131 (1992).
Chauhan, D. P.; Saha, T.; Lahiri, M.; Talukdar, P. "BODIPY based 'click on' fluorogenic dyes: application in live cell imaging." Tetrahedron Lett. 2014, 55, 244-247.
Chen et al., "Chaperone activity of DsbC," J. Bio. Chem., Jul. 9, 1999, 274(28):19601-19605.
Chen et al., "Selection and analysis of an optimized anti-VEGF antibody: crystal structure of an affinity-matured Fab in complex with antigen," J. Mol. Biol., Nov. 5, 1999, 293(4):865-881.
Chen et al., "Selective killing of transformed cells by cyclin/cyclin-dependent kinase 2 antagonists," Proc. Natl. Acad. Sci. U.S.A., Apr. 13, 1999, 96(8):4325-4329.
Cheng, Peter et al., Oseltamivir- and Amandtadine-resistant Influenza Viruses A (H1N1), Emerg. Infect. Dis., Jun. 2009, 15(6): 966-968.
Cheung et al., Stage-specific embryonic antigen-3 (SSEA-3) and beta3GalT5 are cancer specific and significant markers for breast cancer stem cells, PNAS, Jan. 26, 2016, vol. 113, No. 4, pp. 960-965.
Cheung et al., Meeting Info: 23rd International Symposium on Glycoconjugates, GLYCO 23. Split, Croatia. Sep. 15, 2015-Sep. 20, 2015, vol. 32, No. 5, pp. 323.
Chiang et al., Ethyl caffeate suppresses NF-kappaB activation and its downstream inflammatory mediators, iNOS, COX-2, and PGE2 in vitro or in mouse skin. Br J Pharmacol. Oct. 2005; 146(3):352-63.
Chiari, M. et al., Advanced Polymers for Molecular Recognition and Sensing at the Interface. J Chromatography B, Apr. 15, 2008, 866(1-2):89-103.
Childs et al., Receptor-Binding Specificity of Pandemic Influenza A (H1N1) 2009 Virus Determined by Carbohydrate Microarray. Nat. Biotechnol. 2009, 27(9): 797-799.
Cho, Se-Heon et al., Sialyl-Tn Antigen Expression Occurs Early During Human Mammary Carcinogenesis and Is Associated with High Nuclear Grade and Aneuploidy, Cancer Res. 54, 6302-6305, 1994.
Chong et al., Influenza Virus Sialidase: Effect of Calcium on Steady-State Kinetic Parameters, Biochim. Biophys. Acta, Mar. 8, 1991, 1077(1): 65-71.
Chothia et al., "Canonical structures for the hypervariable regions of immunoglobulins," J. Mol. Biol., Aug. 20, 1987, 196(4):901-917.
Chothia et al., "Domain association in immunoglobulin molecules. The packing of variable domains," J. Mol. Biol., Dec. 5, 1985, 186(3):651-663.
Chu, Kuo-Chinget al., Efficient and Stereoselective Synthesis of [alpha](2→9) Oligosialic Acids: From Monomers to Dodecamers, Angewandte Chemie International Edition, vol. 50, No. 40, Sep. 2011, 9391-9395.
Clackson et al., "Making antibody fragments using phage display libraries," Nature, Aug. 15, 1991, 352(6336):624-628.
Clark EA et al., "Structure, function, and genetics of human B cell-associated surface molecules" Adv Cancer Res. 1989;52:81-149.
Clynes R, et al., "Fc receptors are required in passive and active immunity to melanoma" Proc Natl Acad Sci U S A. Jan. 20, 1998;95(2):652-6.
Codelli, J. A. et al., Second-Generation Difluorinated Cycloctynes for Copper-Free Click Chemistry, J. Am. Chem. Soc. 2008, 130, 11486-11493.
Cohen-Daniel et al., Emergance of Oseltamivir-Resistant Influenza A/H3N2 Virus with Altered Hemagglutination Pattern in Hematopoietic Stem Cell Transplant Recipient, J Clin Virol., Feb. 2009, 44(2):138-140.
Coligan et al., Current Protocols in Immunology, sections 2.5.1-2. 6.7, 1991.
Collins et al., Crystal Structures of Oseltamivir-Resistant Influenza Virus Neuraminidase Mutants, Nature, Jun. 26, 2008, 453(7199):1258-1261.
Connor, Robert et al., Receptor Specifcity in Human, Avian, and Equine H2 and H3 Influenza Virus Isolates, Virology, 205: 17, 1994.
Cox et al., New Options for the Prevention of Influenza, N. Engl. J. Med. Oct. 28, 1999, 341(18): 1387-1388.
Cragg, M.S. et al., Complement-Mediated Lysis by Anti-CD20 mAb Correlates with Segregation into Lipid Rafts, Blood 101 (2003) 1045-1052.
Cragg, M.S. et al., Antibody Specificity Controls in Vivo Effector Mechanism of Anti-CD20 Reagents, Blood, 103 (2004) 2738-2743.
Craigo, J. K., Montelaro, R. C. Lessons in AIDS vaccine development learned from studies of equine infectious, anemia virus infection and immunity. Viruses 5, 2963-76, (2013).
Crispin et al., "Carbohydrate and domain architecture of an immature antibody glycoform exhibiting enhanced effector functions," J. Mol. Biol., Apr. 17, 2009, 387(5):1061-1066.
Cunningham et al., "High-resolution epitope mapping of hGH-receptor interactions by alanine-scanning mutagenesis," Science, Jun. 2, 1989, 244(4908):1081-1085.
Cyranoski, Threat of Pandemic Brings Flu Drug Back to Life, Nat. Med. Sep. 2005, 11(9): 909.
Daëron, "Fc receptor biology," Annu. Rev. Immunol., 1997, 15:203-234.
Davies, JW et al., Streamlining Lead Discovery by Aligning in Silico and High-Throughput Screening, Curr Opin Chem Biol. Aug. 2006; 10(4):343-51.
Davodeau et al., "Close phenotypic and functional similarities between human and murine αβ T cells expressing invariant TCR alpha-chains," J. Immunol., Jun. 15, 1997, 158(12):5603-5611.
de Almeida et al., "Thiacycloalkynes for copper-free click chemistry," Angew. Chem. Int. Ed. Engl., Mar. 5, 2012, 51(10):2443-2447.
Debets, M. F. et al., Bioconjugation with Strained Alkenes and Alkynes, Acc. Chem. Res. 2011, 44, 805-815.
De Haas et al., "Fcγ receptors of phagocytes," J. Lab. Clin. Med., Oct. 1995, 126(4):330-341.
Dejong et al., Fatal outcome of human influenza A (H5N1) is associated with high viral load and hypercytokinemia. Nat Med Oct. 2006;12(10):1203-7. Epub Sep. 10, 2006.
Delente, Jacqubs, Glycosylation Revisited, Trends in Biotechnology 3, letters to editor, No. 9 (1985).
Dellabona et al., "An invariant Vα24-JαQ/Vβ11 T cell receptor is expressed in all individuals by clonally expanded CD4⁻8⁻ T cells," J. Exp. Med., Sep. 1, 1994, 180(3):1171-1176.
Demchenko, A.V., Ed., Hanbook of Chemical Glycosylation: Advances in Stereoselectivity and Therapeutic Relevance (2008) Wiley-VCH. Chapter 1. General Aspects of the Glycosidic Bond Formation, in 28 pages.
Dennis, Carina, Cancer: Off by a whisker, Nature 442: 739-741 (2006).
De Paz, J. L., Horlacher, T. & Seeberger, P.H. Oligosaccharide microarrays to map interactions of carbohydrates in biological systems. Methods Enzymol. 415, 269-292, (2006).
Dhodapkar et al., "α-Galactosyl ceramide-loaded dendritic cells for expansion of natural killer T cells" CAPLUS 145:354715 (2006).
Dhodapkar et al., "A reversible defect in natural killer T cell function characterizes the progression of premalignant to malignant multiple myeloma," J. Exp. Med., Jun. 16, 2003, 197(12):1667-1676.

(56) References Cited

OTHER PUBLICATIONS

Dicker, Martina et al., Using Glyco-Engineering to Produce Therapeutic Proteins, Expert Opinion on Biological Therapy, vol. 15, Jan. 1, 2015, pp. 1501-1516.

Dohi, Taeko et al., Fucosyltransferase-Producing Sialyl Lea and Sialyl Lex Carbohydrate Antigen in Benign and Malignant Gastrointestinal Mucosa, Cancer 73, 1552, 1994.

Dohi, H. et al., Stereoselective Glycal Fluorophosphorlation: Synthesis of ADP-2-Fluoroheptose, an Inhibitor of the LPS Biosynthesis, Chem—Eur J 2008, 14, 9530-9539.

Dommerholt, Jan, Readily Accessible Bicyclononynes for Bioorthogonal Labeling and Three-Dimensional Imaging of Living Cells, Angew. Chem. Int. Ed. 2010, 49, 9422-9425.

Doores KJ, et al. A nonself sugar mimic of the HIV glycan shield shows enhanced antigenicity. Proc. Natl. Acad Sci. US.A. 107(40), 17107-17112, (2010).

Doores, K. J. & Burton, D.R. Variable Loop Glycan Dependency of the Broad and Potent HIV-I-Neutralizing Antibodies PG9 and PG16. J. Virol. 84, 10510-10521, (2010).

Doores, K. J. et al. Envelope glycans of immunodeficiency virions are almost entirely oligomannose antigens. Proc. Natl. Acad. Sci. U. S. A 107, 13800-13805, (2010).

Doronina, Svetlana et al., Development of Potent Monoclonal Antibody Auristatin Conjugates for Cancer Therapy, Nat Biotechnol 21(7): 778-784 (2003).

Dougan, Michael et al., Immune Therapy for Cancer, Annual Review of Immunology, 2009, 27, pp. 83-117.

Drugs of the future 25(7): 686 (2000).

Dubertret. Benoit et al., In Vivo Imaging of Quantum Dots Encapsulated in Phospholipid Micelles, Science 298:759-1762, 2002.

Duncan, AR; Winter, G, The binding Site for Clq on IgG, Nature 322:738-40 (1988).

Dunn et al., Zanamivir: A Review of Its Use in Influenza, Drugs, Oct. 1999, 58(4):761-784.

Durrant et al., "Immunology in the clinic review series; focus on cancer: glycolipids as targets for tumour immunotherapy," Clin. Exp. Immunol., Feb. 2012, 167(2):206-215.

Eberl et al., "Selective bystander proliferation of memory $CD4^+$ and $CD8^+$ T cells upon NK T or T cell activation," J. Immunol., Oct. 15, 2000, 165(8):4305-4311.

Eberl et al., "Selective induction of NK cell proliferation and cytotoxicity by activated NKT cells," Eur. J. Immunol., Apr. 2000, 30(4):985-992.

Eggink, D. et al. Lack of complex N-glycans on HIV-I envelope glycoproteins preserves protein conformation and entry function. Virology 401, 236-247, (2010).

Eisen, Michael et al., Binding of the Influenza A Virus to Cell-Surface Receptors: Structures of Five Hemagglutinin-Sialyloligosaccharide Complexes Determined by X-Ray Crystallography, Virology, 232:19, 1997.

Ellis J., et al., Evaluation of Four Real-Time PCR Assays for Detection of Influenza A9H1N1)v Viruses, Euro Surveill. 2009; 14(22), p. 1-3.

Embleton et al., "In-cell PCR from mRNA: amplifying and linking the rearranged immunoglobulin heavy and light chain V-genes within single cells," Nucl. Acids Res., Aug. 11, 1992, 20(15):3831-3837.

Engels et al., "Gene synthesis [new synthetic methods (77)]," Angew. Chem. Int. Ed. Engl., Jun. 1989, 28(6):716-734.

European Search Report issued in connection with corresponding European Patent Application No. 15181446.4, dated Dec. 7, 2015, 10 pages.

Evans, Michael et al., "Mechanism-based profiling of enzyme families," Chem. Rev., Aug. 2006, 106(8):3279-3301.

Evans, "The rise of azide-alkyne 1,3-dipolar 'click' cycloaddition and its application to polymer science and surface modification," Australian J. Chem., Jun. 2007, 60(6):384-395.

Extended European Search Report dated Jan. 5, 2016 in European Patent Application No. 13830785.5, in 10 pages.

Extended European Search Report, App. No. 15799789.1, dated Nov. 28, 2017, 10 Pages.

Extended European Search Report, App. No. 158001917, dated Nov. 28, 2017, 12 Pages.

Extended European Search Report, App. No. 15799981.4, dated Nov. 29, 2017, 9 Pages.

Falkowska, E. et al. Broadly neutralizing HIV antibodies define a glycan-dependent epitope on the prefusion conformation of gp41 on cleaved envelope trimers. Immunity 40, 657-68, 2014.

Fan, Shu-Quan et al., Remarkable Transglycosylation Activity of Glycosynthase Mutants of Endo-D, an Endo-ß-N-acetylglucosaminidase from Streptococcus pneumoniae, JBC vol. 287, No. 14, pp. 11272-11281, Mar. 30, 2012.

Fazio, F. et al., Synthesis of sugar arrays in microtiter plate. J. Am. Chem. Soc. 124, 14397-14402, (2002).

FDA Guidance for Industry for Container Closure Systems for Packaging Human Drugs and Biologics, May 1999.

Fedson, Confronting the next influenza pandemic with anti-inflammatory and immunomodulatory agents: why they are needed and how they might work. Influenza Other Respi Virusts. Jul. 2009;3(4):129-42.

Fellouse et al., "Synthetic antibodies from a four-amino-acid code: a dominant role for tyrosine in antigen recognition," Proc. Natl. Acad. Sci. U.S.A., Aug. 24, 2004, 101(34):12467-12472.

Fernandez-Tejada, Alberto et al., Designing synthetic vaccines for HIV. Expert Rev. Vaccines 14, 815-31, 2015.

Fernandez-Megia et al., A Click Approach to Unprotected Glycodendrimers. Macromolecules 2006, vol. 39, pp. 2113-2120.

Fessner et al., Enzymes in Organic Synthesis, Short Enzymatic Synthesis of L-Fucose Analogs. Eur. J. Org. Chem 2000, p. 125-132.

Fiehn, Oliver, Combining Genomics, Metabolome Analysis, and Biochemical Modelling to Understand Metabolic Networks, Comparative and Functional Genomics 2:155-168, 2001.

Fishwild et al., "High-avidity human IgGκ monoclonal antibodies from a novel strain of minilocus transgenic mice," Nature Biotechnol., Jul. 1996, 14(7):845-851.

Fraker, PJ et al., Protein and Cell Membrane Iodinations with a Sparingly Soluble Chloroamide, 1,3,4,6-tetrachloro-3a,6a-diphrenylglycoluril, Biochem. Biophys. Res. Commun. 80: 49-57 (1978).

Frank, Natasha et al., The Therapeutic Promise of the Cancer Stem Cell Concept, Journal of Clinical Investigation, 120(1) 41-50, Jan. 2010.

Fredman et al., "Expression of gangliosides GD3 and 3'-isoLM1 in autopsy brains from patients with malignant tumors," J. Neurochem., Jan. 1993, 60(1):99-105.

Fredman et al., "Potential ganglioside antigens associated with human gliomas," Neurol. Res., Jun. 1986, 8(2):123-126.

Fredman et al., "Sialyllactotetraosylceramide, a ganglioside marker for human malignant gliomas," J. Neurochem., Mar. 1988, 50(3):912-919.

Friscourt, F. et al., A Fluorogenic Probe for the Catalyst-Free Detection of Azide-Tagged Molecules, J. Am. Chem. Soc. 2012, 134, 18809-18815.

Friscourt et al., "Polar Dibenzocyclooctynes for Selective Labeling of Extracellular Glycoconjugates of Living Cells," J. Am. Chem. Soc., Mar. 21, 2012, 134(11):5381-5389.

Fujimore, Kenji et al., A Modeling Analysis of Monoclonal Antibody Percolation Through Tumors: A Binding-Site Barrier, J Nuc Med. 31: 1191-1198 (1990).

Fujio, M. et al. "Structure-Based Discovery of Glycolipids for CD1d-Mediated NKT Cell Activation: Turning the Adjuvant versus Immunosuppression Activity." CAPLUS 145:240945 (2006).

Fujio, M. et al. "Structure-Based Discovery of Glycolipids for CD1d-Mediated NKT Cell Activation: Turning the Adjuvant versus Immunosuppression Activity." J. Am. Chem. Soc. (2006), vol. 128, pp. 9022-9023.

Fujita M et al., "A novel disaccharide substrate having 1,2-oxazoline moiety for detection of transglycosylating activity of endoglycosidases" Biochim Biophys Acta. Sep. 3, 2001;1528(1):9-14.

(56) References Cited

OTHER PUBLICATIONS

Fukui, S et al., Oligosaccharide microarrays for high-throughput detection and specificity assignments of carbohydrate-protein interactions. Nat. Biotechnol. 20, 1011-1017, (2002).
Galfrè et al., "Preparation of monoclonal antibodies: strategies and procedures," *Methods Enzymol.*, 1981, 73(Pt B):3-46.
Gamblin, SJ et al., The Structure and Receptor Binding Properties of the 1918 Influenza Hemagglutinin, Science, 303:1838, 2004.
Garces, F. et al. Structural evolution of glycan recognition by a family of potent HIV antibodies. Cell 159, 69-79, (2014).
Gaschen, B. et al. AIDS—Diversity Considerations in HIV-I vaccine selection. Science 296, 2354-2360, (2002).
Gazzano-Santoro et al., "A non-radioactive complement-dependent cytotoxicity assay for anti-CD20 nonclonal antibody," *J. Immunol. Methods*, Mar. 28, 1997, 202(2):163-171.
Geiler et al., Comparison of pro-inflammatory cytokine expression and cellular signal transduction in human macrophages infected with different influenza A viruses. Med Microbiol Immunol. Feb. 2011;200(1):53-60.
GenBank accession No. AAA24922.1, "endoglycosidase F [Elizabethkingia meningoseptica]," May 27, 2008.
GenBank accession No. AAA24923.1, "endoglycosidase, partial [Elizabethkingia meningoseptica]," Jun. 8, 1993.
GenBank accession No. AAA24924.1.1, "endoglycosidase, partial [Elizabethkingia meningoseptica]," Jun. 7, 1993.
GenBank accession No. AAA26738.1, "endo-beta-N-acetylglucosaminidase H [Streptomyces plicates]," Apr. 26, 1993.
GenBank accession No. J05449.1, "F.meningosepticum peptide-N-4-(N-acetyl-beta-D-glucosaminyl) asparagine amidase (PNGase F) mRNA, complete cds," Jan. 16, 1996.
GenBank accession No. YP_212855.1, "Putative exported alpha-L-fucosidase protein [Bacteroides fragilis NCTC 9343]," Mar. 2, 2014.
GenBank accession No. WP_0080769537.1, published May 10, 2013.
GenBank accession No. WP_008767711.1, published May 10, 2013.
Geoghegan, Kieran et al., Site-Directed Conjugation of Nonpeptide Groups to Peptides and Proteins Via Periodate Oxidation of a 2-amino Alcohol. Applications to Modification at N-Terminal Serine, Bioconjugate chem. 3:138-146 (1992).
Gerson et al., "ESR. Spectra and Structures of Radical Anions in the Dibenzo[a, e]cyclooctene Series," *Helvetica Chinica Acta*, Jan. 1, 1976, 59(6): 2038-2048.
Giaccone, Giuseppe et al., "A phase I study of the natural killer T-cell ligand α-galactosylceramide (KRN7000) in patients with solid tumors," *Clin. Cancer Res.*, Dec. 2002, 8(12):3702-3709.
Gill et al., "Direct brain infusion of glial cell line-derived neurotrophic factor in Parkinson disease," *Nature Med.*, May 2003, 9(5):589-595 and Addendum from Apr. 2006, 12(4):479.
Go, E. P. et al. Characterization of glycosylation profiles of HIV-I transmitted/founder envelopes by mass spectrometry. J. Virol. 85, 8270-8284, (2011).
Go, E. P. et al. Comparative Analysis of the Glycosylation Profiles of Membrane-Anchored HIV-I Envelope Glycoprotein Trimers and Soluble gp140. J. Virol. 89, 8245-57, (2015).
Godefroy, S. et al., Effect of Skin Barrier Disruption on Immune Responses to Topically Applied Cross-Reacting Material, CRM197 of Diphtheria Toxin, Infect. Immun. 2005, 73, 4803.
Goding, *Monoclonal Antibodies: Principles and Practice 2nd ed., Chapter 3: Production of Monoclonal Antibodies*, 1986, pp. 59-103, Academic Press, London.
Goldenthal et al., "Safety Evaluation of Vaccine Adjuvants: National Cooperative Vaccine Development Working Group," *AIDS Res. Hum. Retroviruses*, 1993, 9(Supp.1):S47-S51.
Golkowski et al., "Strategy for catch and release of azide-tagged biomolecules utilizing a photolabile strained alkyne construct," *Organic and Biomolecular Chemistry*, Jan. 1, 2012, 10(23):4496.

Goochee CF et al., "The oligosaccharides of glycoproteins: bioprocess factors affecting oligosaccharide structure and their effect on glycoprotein properties", *Biotechnology* (N Y). Dec. 1991;9(12):1347-55.
Gordon et al., "Reactivity of biarylazacyclooctynones in copper-free click chemistry," *J. Am. Chem. Soc.*, Jun. 6, 2012, 134(22): 9199-9208.
Gottschling et al., "Stage-specific embryonic antigen-4 is expressed in basaloid lung cancer and associated with poor prognosis," *Eur. Respir. J.*, Mar. 2013, 41(3):656-663.
Govorkova et al, Combination chemotherapy for influenza. Viruses. Aug. 2010;2(8):1510-29.
Graham et al., "Characteristics of a human cell line transformed by DNA from human adenovirus type 5," *J. Gen. Virol.*, Jul. 1977, 36(1):59-72.
Graham, Duncan et al., Surface-Enhanced Resonance Raman Scattering as a Novel Method of DNA Discrimination, Angew. Chem., 2000, 112(6), 1103-1105.
Gram et al., "In vitro selection and affinity maturation of antibodies from a naive combinatorial immunoglobulin library," *Proc. Natl. Acad. Sci. U.S.A.*, Apr. 15, 1992, 89(8):3576-3580.
Grandjean, C. et al., On the Preparation of Carbohydrate-Protein Conjugates Using the Traceless Staudinger Ligation, J Org Chem 2005, 70, 7123-7132.
Green, "Targeting targeted therapy," *N. Engl. J. Med.*, May 20, 2004, 350(21):2191-2193.
Greenbaum et al., "Chemical approaches for functionally probing the proteome," *Mol. Cell. Proteomics*, 2002, 1:60-68.
Griffiths et al., "Human anti-self antibodies with high specificity from phage display libraries," *EMBO J.*, Feb. 1993, 12(2):725-734.
Gruber et al., "Efficient tumor cell lysis mediated by a bispecific single chain antibody expressed in *Escherichia coli*," *J. Immunol.*, Jun. 1, 1994, 152(11):5368-5374.
Grubisha, D. S. et al., Femtomolar Detection of Prostate-Specific Antigen: An Immunoassay Based on Surface-Enhanced Raman Scattering and Immunogold labels, Anal. Chem. (2003), 75, 5936-5943.
Gulati et al., Deletions of Neuraminidase and Resistance to Oseltamivir May Be a Consequence of Restricted Receptor Specificity in Recent H3N2 Influenza Viruses. Virol. J. 2009, 6(22)L 1-15.
Gulland, Fire Cases of Spread of Oseltamivir Resistant Swine Flu Between Patients are Reported in Wales, BMJ, Nov. 23, 2009:339:b4975.
Guss et al., "Structure of the IgG-binding regions of streptococcal protein G," *EMBO J.*, Jul. 1986, 5(7):1567-1575.
Guyer et al., "Immunoglobulin binding by mouse intestinal epithelial cell receptors," *J. Immunol.*, Aug. 1976, 117(2):587-593.
Ha, Ya et al., X-Ray Structures of H5 Avian and H9 Swine Influenza Virus Hemagglutinins Bound to Avian and Human Receptor Analogs, Proc Natl Acad Sci USA, 98:11181-11186, 2001.
Ha, Ya et al., X-Ray Structure of the Hemagglutinin of a Potential H3 Avian Progenitor of the 1968 Hong Kong Pandemic Influenza Virus, Virology, 309:209-218, 2003.
Hajishengallis, "Mucosal immunization with a bacterial protein antigen genetically coupled to cholera toxin A2/B subunits," *J. Immuol.*, May 1, 1995, 154(9):4322-4332.
Hakomori et al., "Glycosphingolipid antigens and cancer therapy," *Chem. Biol.*, Feb. 1997, 4(2):97-104.
Hakomori, "Glycosylation defining cancer malignancy: new wine in an old bottle," *Proc. Natl. Acad. Sci. U.S.A.*, Aug. 6, 2002, 99(16):10231-10233.
Ham, Richard et al., Media and Growth Requirements, Meth. Enz 58, 44 (1979).
Hammerling et al., in: Monoclonal Antibodies and T-Cell Hybridomas 563-587, 1981.
Han, Junyan et al., 3- and 5-Functionalized BODIPYs via the Liebeskind-Srogl Reaction, Organic & Biomolecular Chemistry (2009), 7(1), 34-36.
Hanski, Christoph et al., Altered Glycosylation of the MUC-1 Protein Core Contributes to the Colon Carcinoma-Associated Increase of Mucin-Bound Sialyl-Lewis Expression, Cancer Res. 53, 4082-4088 (1993).
Hanski, C. et al., Characterization of the Major Sialyl-Lex-Poristive Mucins Present in Colon, Colon Carcinoma, and Sera of Patients with Colorectal Cancer, Cancer Res. 55, 928-933 (1995).

(56) References Cited

OTHER PUBLICATIONS

Hara et al., "Overproduction of penicillin-binding protein 7 suppresses thermosensitive growth defect at low osmolarity due to an spr mutation of *Escherichia coli*," Microbial Drug Resistance, Spring 1996, 2(1):63-72.
Harris, "Production of humanized monoclonal antibodies for in vivo imaging and therapy," Biochem. Soc. Transactions, Nov. 1995, 23(4):1035-1038.
Hasegawa, Akira, et al., Synthesis of Sialyl Lewis X Ganglioside Analogues Containing Modified L-Fucose Residues, Carbohydr. Res. 1995, 274, 165-181.
Hata, K. et al., Limited Inhibitory Effects of Oseltamivir and Zanamivir on Human Sialidases, Antimicrobial Agents and Chemotherapy, vol. 52, No. 10, Oct. 2008, in 8 pages.
Hawkins et al., "Selection of phage antibodies by binding affinity. Mimicking affinity maturation," J. Mol. Biol., 1992, 226(3):889-896.
Healthy Living, "10 Simple and Natural Ways to Boost Your Immune System," Published Jan. 31, 2014, downloaded from online, http://www.everydayhealth.com/columns/white-seeber-grogan-the-remedy-chicks/ten-simple-natural-ways-to-b . . . on Aug. 19, 2016.
Henglein, A. et al., Absorption Spectrum and Some Chemical Reactions of Colloidal Platinum in Aqueous Solution, J. Phys. Chem., 99, 14129 (1995).
Herner, A et al., A new family of bioorthogonally applicable fluorogenic labelst, Org. Biomol. Chem. 2013, 11, 3297-3306.
Hey, Thomas et al., Artificial, non-antibody binding proteins for pharmaceutical and industrial application, Trends in Biotechnology 23(10) 514-522 (2005).
Heyman, "Complement and Fc-receptors in regulation of the antibody response," Immunol. Lett., Dec. 1996, 54(2-3):195-199.
Hinman et al., "Preparation and characterization of monoclonal antibody conjugates of the calicheamicins: a novel and potent family of antitumor antibiotics," Cancer Res., Jul. 15, 1993, 53(14):3336-3342.
Hirabayashi, J. et al., Oligosaccharide Microarrays for Glycomics, Trends in Biotechnology 21 (4): 141-143, 2003.
Hogrefe et al., "A bacteriophage lambda vector for the cloning and expression of immunoglobulin Fab fragments on the surface of filamentous phage," Gene, Jun. 15, 1993, 128(1):119-126.
Holliger et al., "'Diabodies': small bivalent and bispecific antibody fragments," Proc. Natl. Acad. Sci. U.S.A., Jul. 15, 1993, 90(14):6444-6448.
Holmskov, Uffe et al., Collectins: Collagenous C-Type Lectins of the Innate Immune Defense System, 1994, Immunol. Today, 15: 67.
Honda et al., Synthesis and anti-influenza virus activity of 7-0-alkylated derivatives related to zanamivir. Bioorg Med Chem Lett. Aug. 5, 2002;12(15):1925-8.
Honegger et al., "Yet another numbering scheme for immunoglobulin variable domains: an automatic modeling and analysis tool," J. Mol. Biol., Jun. 8, 2001, 309:657-670.
Hoogenboom et al., "By-passing immunisation: Human antibodies from synthetic repertoires of germline $V_H$ gene segments rearranged in vitro," J. Mol. Biol., Sep. 20, 1992, 227(2):381-388.
Hoogenboom et al., "Multi-subunit proteins on the surface of filamentous phage: methodologies for displaying antibody (Fab) heavy and light chains," Nucl. Acids Res., Aug. 11, 1991 19(15):4133-4137.
Hotha, Srinivas et al., "Click Chemistry" Inspired Synthesis of Pseudo-Oligosaccharides and Amino Acid Glycoconjugates, J Org Chem 2006, 71, 364-367.
Horiya, S. et al., Recent strategies targeting HIV glycans in vaccine design. Nat. Chem. Biol. 10, 990-999, (2014).
Horn et al., Investigation into an Efficient Synthesis of 2,3-dehydro-N-acetyl Neuraminic Acid Leads to Three Decarboxylated Sialic Acid Dimers, Carbohdr. Res., Apr. 7, 2008, 343(5):936-940.
Howard et al., "Biological properties of interleukin 10," Immunol. Today, Jun. 1992, 13(6):198-200.
Hsu et al., "Alkynyl sugar analogs for the labeling and visualization of glycoconjugates in cells," Proc. Natl. Acad. Sci. USA, Feb. 20, 2007, 104(8), 2614-2619.
Hsu, Nien-Yeen et al., Desorption Ionization of Biomolecules on Metals, Anal. Chem., 80, 5203-5210, 2008.
Huang et al., "Carbohydrate-based vaccines with a glycolipid adjuvant for breast cancer," Proc. Natl. Acad. Sci. U.S.A., Feb. 12, 2013, 110(7):2517-2522.
Huang, Wei et al., Chemoenzymatic Glycoengineering of Intact lgG Antibodies for Gain of Functions, Journal American Chemical Socirty, vol. 134, No. 9, Jul. 25, 2012, pp. 12308-12318.
Huang, Lijun et al., Iterative One-Pot Syntheses of Chitotetroses, Carbohydr. Res. 2006, 341, 1669-1679.
Huang et al., Recombinant immunotherpaeutics: current state and perspectives regarding the feasibility and market, Appl Microbiol Biotechnol, 87: 401-410. 2010.
Hung et al., "Investigation of SSEA-4 binding protein in breast cancer cells," J. Am. Chem. Soc., Apr. 24, 2013, 135(16):5934-5937.
Hurle et al., "Protein engineering techniques for antibody humanization," Curr. Opin. Biotechnol., Aug. 1994, 5(4):428-433.
Immunogenicity, Wikipedia p. 1-3. Downloaded on Aug. 16, 2016 from https://en.wikipedia.org/wiki/Immunogenicity. (2016).
Inouye et al., "Single-step purification of F(ab')$_{2u}$ fragments of mouse monoclonal antibodies (immunoglobulins M) by hydrophobic interaction high-performance liquid chromatography using TSKgel Ether-5PW," J. Biochem. Biophys. Methods, Feb. 1993, 26(1):27-39.
International Search Report and Written Opinion issued for International application No. PCT/US2015/011748, dated Aug. 21, 2015, 17 pages.
International Search Report and Written Opinion issued for International application No. PCT/US2015/032737, dated Oct. 1, 2015, 13 pages.
International Search Report and Written Opinion issued for International application No. PCT/US2015/032738, dated Oct. 20, 2015, 15 pages.
International Search Report and Written Opinion issued for International application No. PCT/US2015/032740, dated Oct. 26, 2015, 13 pages.
International Search Report and Written Opinion issued for International application No. PCT/US2015/032744, dated Oct. 2, 2015, 12 pages.
International Search Report and Written Opinion issued for International application No. PCT/US2015/032745, dated Oct. 8, 2015, 13 pages.
International Search Report dated Jan. 13, 2012, from corresponding International Patent Application No. PCT/US2011/035982, 17 pages.
International Search Report dated Nov. 13, 2014, from corresponding International Patent Application No. PCT/US2014/054617, 10 pages.
International Search Report issued for International application No. PCT/US2015/049014, dated Dec. 14, 2015, 3 pages.
International Search Report and Written Opinion in International Application No. PCT/US16/15858, dated Jun. 27, 2016, in 8 pages.
International Search Report issued for International application No. PCT/US15/22977, dated Jun. 22, 2015, 3 pages.
International Search Report issued for International application No. PCT/US15/40199, dated Mar. 2, 2016, 6 pages.
International Search Report issued for International application No. PCT/US2009/050754, dated Feb. 24, 2010, 10 pages.
International Search Report and Written Opinion in International Application No. PCT/US2017/021454, dated Jul. 31, 2017, 8 pages.
International Search Report and Written Opinion in International Application No. PCT/US2017/048074, dated Dec. 26, 2017, 17 pages.
Isshiki et al., Cloning, Expression, and Characterization of a Novel UDP-galactose:b-N-Acetylglucosamine b1,3-Galactosyltransferase (b3Gal-T5) Responsible for Synthesis of Type 1 Chain in Colorectal and Pancreatic Epithelia and Tumor Cells Derived Therefrom, The Journal of Biological Chemistry, Apr. 30, 1999, vol. 274, No. 18, pp. 12499-12507.

(56) References Cited

OTHER PUBLICATIONS

Ito, Akihiro et al., A Novel Ganglioside Isolated From Renal Cell Carcinoma, Biol Chem 2001, 276, 16695.
Jackson et al., "In vitro antibody maturation: Improvement of a high affinity, neutralizing antibody against IL-1β," *J. Immunol.*, Apr. 1, 1995, 154(7):3310-3319.
Jacobs et al., "Metabolic labeling of glycoproteins with chemical tags through unnatural sialic acid biosynthesis," *Methods Enzymol.*, 2000, 327:260-275.
Jakobovits et al., "Analysis of homozygous mutant chimeric mice: deletion of the immunoglobulin heavy-chain joining region blocks B-cell development and antibody production," *Proc. Natl. Acad. Sci. U.S.A.*, Mar. 15, 1993, 90(6):2551-2555.
Jakobovits et al., "Germ-line transmission and expression of a human-derived yeast artificial chromosome," *Nature*, Mar. 18, 1993, 362(6417):255-258.
Japanese Office Action dated Apr. 21, 2015, from Related Japanese Patent Application No. 2013-510261, 6 Pages.
Jayasena, Sumedha, Aptamers: An Emerging Class of Molecules That Rival Antibodies in Diagnostics, Clin. Chem. (1999), 45, 1628-1650.
Jenkins N, Curling EM., "Glycosylation of recombinant proteins: problems and prospects", *Enzyme Microb Technol.* May 1994;16(5):354-64.
Jewett, J.C.; Bertozzi, C.R., Cu-Free Click Cycloaddition Reactions in Chemical Biology, Chem. Soc. Rev. 2010, 39, 1272-1279.
Jewett, J.C.; Sletten, E. M.; Bertozzi, C.R., Rapid Cu-Free Click Chemistry with Readily Synthesized Biarylazacyclooctynones, J. Am. Chem. Soc. 2010, 132, 3688-3690.
Jewett et al., "Synthesis of a fluorogenic cyclooctyne activate by Cu-free click chemistry," *Org. Lett.*, Nov. 18, 2011, 13(22):5937-5939.
Jin, R. C. et al., Photoinduced Conversion of Silver Nanospheres to Nanoprisms, Science (2001), 294, 1901-1903.
Jobling, Michael et al., Fusion Proteins Containing the A2 Domain of Cholera Toxin Assemble With B Polypeptides of Cholera Toxin to Form Immunoreactive and Functional Holotoxin-Like Chimeras, Infect Immun., 60: 4915-24, 1992.
John, F. & Hendrickson, T. L. Synthesis of Truncated Analogues for Studying the Process of Glycosyl Phosphatidylinositol Modification. Org. Lett. 12, 2080-2083, (2010).
Jones et al., "Rapid PCR-cloning of full-length mouse immunoglobulin variable regions," *Nature Biotechnol.*, Jan. 1991, 9(1):88-89.
Jones et al., "Replacing the complementarity-determining regions in a human antibody with those from a mouse," *Nature*, May 29-Jun. 4, 1986, 321(6069):522-525.
Jones, "Analysis of polypeptides and proteins," *Adv. Drug Delivery Rev.*, Jan.-Apr. 1993, 10(1):29-90.
Jonges, M. et al., Dynamics of Antiviral-Resistant Influenza Viruses in the Netherlands, 2005-2008, Antiviral Res., Sep. 2009, 83(3): 290-297.
Jorgensen, Trond et al., Up-Regulation of the Oligosaccharide Sialyl Lewisx: A New Prognostic Parameter in Metastatic Prostate Cancer, Cancer Res. 55, 1817-1819, 1995.
Jose, Jiney et al., Energy transfer dyads based on Nile Red, Tetrahedron Letters (2009), 50(47), 6442-6445.
Joshi, Shantaran et al., Cell Surface Properties Associated with Malignancy of Metastatic Large Cell Lymphoma Cells, (1987) Cancer Res. 47, 3551-3557.
Joyce, J. G. et al. An oligosaccharide-based HIV-I 2G12 mimotope vaccine induces carbohydrate-specific antibodies that fail to neutralize HIV-I virions. Proc. Natl. Acad. Sci. U. S. A 105, 15684-15689, (2008).
Kakeji, Y. et al., Correlation Between Sialyl Tn Antigen and Lymphatic Metastasis in Patients with Borrmann Type IV Gastric Carcinoma, Brit. J. Cancer 71, 191-195, 1995.
Kale et al., Detection of intact influenza viruses using biotinylated biantennary S-sialosides. J Am Chem Soc. Jul. 2, 2008;130(26):8169-71.
Kalesh et al., "Peptide-based activity-based probes (ABPs) for target-specific profiling of protein tyrosine phosphatases (PTPs)," *Chem. Commun.*, Jan. 28, 2010, 46(4):589-591.
Kamkaew, A. et al., "BODIPY dyes in photodynamic therapy." Chem. Soc. Rev. 2013, 42, 77-88.
Kam et al., "Carbon nanotubes as multifunctional biological transporters and near-infrared agents for selective cancer cell destruction," *Proc. Natl. Acad. Sci. U.S.A.*, Aug. 16, 2005, 102(33):11600-11605.
Kaneko et al., "Anti-inflammatory activity of immunoglobulin G resulting from Fc sialylation," *Science*, Aug. 4, 2006, 313(5787):670-673.
Kawakami et al., "Critical role of Vα14+ natural killer T cells in the innate phase of host protection against *Streptococcus pneumoniae* infection," *Eur. J. Immunol.*, Dec. 2003, 33(12):3322-3330.
Kawano et al., "CD1d-restricted and TCR-mediated activation of $v_\alpha$14 NKT cells by glycosylceramides," *Science*, Nov. 28, 1997, 278(5343):1626-1629.
Kanie, Osmau et al., Orthogonal glycosylation strategy in synthesis of extended blood group B determinant. Tetrahedron Lett. 37, 4551-4554 (1996).
Kannagi et al., "New globoseries glycosphingolipids in human teratocarcinoma reactive with the monoclonal antibody directed to a developmentally regulated antigen, stage-specific embryonic antigen 3," *J. Biol. Chem.*, Jul. 25, 1983, 258(14):8934-8942.
Kannagi et al., "Stage-specific embryonic antigens (SSEA-3 and -4) are epitopes of a unique globo-series ganglioside isolated from human teratocarcinoma cells," *EMBO J.*, 1983, 2(12):2355-2361.
Kannappan, Ramaswamy et al., "Photoaffinity labeling of sialidase with a biotin-conjugated phenylaminodizairine derivative of 2,3-didehydro-2-deoxy-N-acetylneuraminic acid," *Biol. Pharm. Bull.*, Mar. 2008, 31(3):352-356.
Karlin, Samuel et al., Applications and Statistics for Multiple High-Scoring Segments in Molecular Sequences, Proc. Natl. Acad Sci. USA 90:5873-77, 1993.
Karlin S. et al., "Methods for assessing the statistical significance of molecular sequence features by using general scoring schemes", *Proc Nati Acad Sci USA.* Mar. 1990;87(6):2264-8.
Karmakar, M. et al., Current Trends in Research and Application of Microbial Cellulases, Research Journal of Microbiology, (2001) 6(1): 41-53.
Katagiri, Yohko et al., Laminin Binding Protein, 34/67 Laminin Receptor, Carries Stage-Specific Embryonic Antigen-4 Epitope Defined by Monoclonal Antibody Raft.2, Biochemical and Biophysical Research Communcations, 332, 1004-1011, 2005.
Kato et al., "GMab-1, a high-affinity anti-3'-isoLM1/3'6'-isoLD1 IgG monoclonal antibody, raised in lacto-series ganglioside-defective knockout mice," *Biochem. Biophys. Res. Commun.*, Jan. 1, 2010, 391(1):750-755.
Kermani, Pouneh et al., Production of ScFv Antibody Fragments Following Immunization with a Phage-Displayed Fusion Protein and Analysis of Reactivity to Surface-Exposed Epitopes of the Protein F of Pseudomonas Aeruginosa by Cytofluorometry, Hybridoma, 14(4):323-328 (1995).
Kidd et al., "Profiling serine hydrolase activities in complex proteomes," *Biochemistry*, Apr. 3, 2001, 40(13):4005-4015.
Kiick, K.L. et al., Identification of an Expanded Set of Translationally Active Methionine Analogues in *Escherichia coli*, tetrahedron 56:9487, 2001.
Kim et al., "Localization of the site of the murine IgG1 molecule that is involved in binding to the murine intestinal Fc receptor," *Eur. J. Immunol.*, 1994, 24:2429-2434.
Kim et al., High-Throughput Screening of Glycan-Binding Proteins Using Miniature Pig Kidney N-Glycan-Immobilized Beads, Chemistry & biology 15.3, p. 215-223 (2008).
Kim, Gap-Sue et al., AB Initio Study of Excited Electronic States and Vibronic Spectra of Phenyl Radical, Chem Phys. Lett., 2002, 3 5 2, 421.
Kimura et al., Design and Synthesis of Immobilized Tamiflu Analog on Resin for Affinity Chromatography, Tetrahedron Lett., Jul. 1, 2009, 50(26):3205-3208.
King, M. et al., New Tetramethlthiepinium (TMTI) for Copper-Free Click Chemistry, Chem. Commun. 2012, 48, 9308-9309.

(56) References Cited

OTHER PUBLICATIONS

Kitamura et al., "α-galactosylceramide induces early B-cell activation through IL-4 production by NKT cells," *Cell. Immunol.*, Jan. 10, 2000, 199(1):37-42.
Klein, J. et al., "Isomaltines and their N-acyl derivatives, their preparation, and use of some acyl derivatives as surfactants or for preparation of hydrophilic polymers," CAPLUS 110:95711 (1989).
Köhler et al., "Continuous cultures of fused cells secreting antibody of predefined specificity," *Nature*, Aug. 7, 1975, 256(5517):495-497.
Kolb et al., "Click chemistry: diverse chemical function from a few good reactions," *Angew. Chem. Int. Ed. Engl.*, Jun. 1, 2001, 40(11):2004-2021.
Kolb et al., "The growing impact of click chemistry on drug discovery," *Drug Discov. Today*, Dec. 15, 2003, 8(24):1128-1137.
Komba S, et al. Synthesis and Bioloical Activities of Three Sulfated Sialyl Lex Ganglioside Analogues for Clarifying the Real Carbohydrate Ligand Structure of L-Selectin, Bioorg. Med. Chem. 1996, 4, 1833-1847.
Komori, Tatsuya et al., Study on Systematizing the Synthesis of the A-Series Ganglioside Glycans GT1a, GD1a, and GM1 Using the Newly Developed N-Troc-Protected GM3 and GaIN Intermediates, Carbohydr. Res. 2009, 344, 1453.
Kong, L. et al. Expression-system-dependent modulation of HIV-I envelope glycoprotein antigenicity and immunogenicity. J. Mol. Biol. 403, 131-147, (2010).
Kontermann, "Intrabodies as therapeutic agents," *Methods*, Oct. 2004, 34(2):163-170.
Kos, "Regulation of adaptive immunity by natural killer cells," *Immunol. Res.*, 1998, 17(3):303-312.
Koshihara et al., 1984, Biochmica et biophysica acta, 792(1), pp. 92-97.
Kostelny et al., "Formation of a bispecific antibody by the use of leucine zippers," *J. Immunol.*, Mar. 1, 1992, 148(5):1547-1553.
Kotteas et al., Immunotherapy for pancreatic cancer, J cancer Res Clin Oncol, 142(8): 1795-1805, 2016.
Kozbor, "A human hybrid myeloma for production of human monoclonal antibodies," *J. Immunol.*, Dec. 1984, 133(6):3001-3005.
Kriegler M et al., "A novel form of NF/cachectin is a cell surface cytotoxic transmembrane protein: ramifications for the complex physiology of TNF" *Cell*. Apr. 8, 1988;53(1):45-53.
Krise, Jeffrey et al., Prodrugs of Phosphates, Phosphonates, and Phosphinates, Adv. Drug Deliv. Rev. 1996, 19(2), 287-310.
Kruis et al., Low dose balsalazide (1.5 g twice daily) and mesalazine (0.5 g three times daily) maintained remission of ulcerative colitis but high dose alsalazide (3.0 g twice daily) was superior in preventing relapses. Gut. Dec. 2001;49(6):783-9.
Kubin, R. F. et al., Fluorescence Quantum Yields of Some Rhodamine Dyes, Luminescence 1982, 27, 455-462.
Kubler-Kielb, J. et al., A New Method for Conjugation of Carbohydrates to Proteins Using an Aminooxy-Thiol Heterbifunctional Linker, J Org Chem 2005, 70, 6987-6990.
Kudo et al., "Up-regulation of a set of glycosyltransferase genes in human colorectal cancer," *Lab. Invest.*, Jul. 1998, 78(7):797-811.
Kwong, Peter et al., Rational Design of Vaccines to Elicit Broadly Neutralizing Antibodies to HIV-I. Cold Spring Harb.Perspect. Med. 1, 2011, 1-16.
Lantz et al., "An invariant T cell receptor α chain is used by a unique subset of major histocompatibility complex class I-specific CD4+ and CD4−8− T cells in mice and humans," *J. Exp. Med.*, Sep. 1, 1994, 180(3):1097-1106.
Lau et al., "N-Glycans in cancer progression," *Glycobiology*, Oct. 2008, 18(10):750-760.
Lau, K. et al. Highly efficient chemoenzymatic synthesis of ß1-4-linked galactosides with promiscuous bacterial β1-4-galactosyltransferases. Chem. Commun. 46, 6066-6068, (2010).
Le, Mai et al., Avian flu: Isolation of Drug-Resistant H5N1 Virus, Nature, Oct. 20, 2005, 437(7062):1108.
Lebens et al., Mucosal vaccines based on the use of cholera toxin B as immunogen and antigen carrier, *Dev. Biol. Stand.*, 1994, 82:215-227.
Le Droumaguet, C. et al., Fluorogenic Click Reaction., Chem. Soc. Rev. 2010, 39, 1233-1239.
Lederman et al., A single amino acid substitution in a common African allele of the CD4 molecule ablates binding of the monoclonal antibody, OKT4, Molecular Immunology, 28, 1171-1181 (1991).
Lee et al., Analogs of Cell Surface Carbohydrates. Synthesis of D-Galactose Derivatives Having an Ethynyl, Vinyl or Epoxy Residue at c-5. Carbohydrate Research 1988, vol. 176, pp. 59-72.
Lee et al., "Bivalent antibody phage display mimics natural immunoglobulin," *J. Immunol. Methods*, Jan. 2004, 284(1-2):119-132.
Lee et al., "High-affinity human antibodies from phage-displayed synthetic Fab libraries with a single framework scaffold," *J. Mol. Biol.*, Jul. 23, 2004, 340(5):1073-1093.
Lee et al., A new Solvent System for Efficient Synthesis of 1,2,3-Triazoles, Tetrahedron Lett., Jul. 17, 2006, 47(29):5105-5109.
Lee et al., An Efficient and Practical Method for the Synthesis of Mono-N-Protected α,ω-diaminoalkanes, Tetrahedron Lett., Apr. 2, 2001, 42(14):2709-2711.
Lee, H.K. et al. Reactivity-based one-pot synthesis of oligomannoses: defining antigens recognized by 2G12, a broadly neutralizing anti-HIV-I antibody. Angew. Chem. Int. Ed. 43, 1000-1003, (2004.
Lee et al., Immunogenicity Study of Globo H Analogues with Modification at the Reducing or Nonreducing end of the tumor antigen, J Am Chem Soc, 136: 16844-16853 (2014).
Lefranc et al., "IMGT, the international ImMunoGeneTics database," *Nucleic Acids Res.*, Jan. 1, 1999, 27(1):209-212.
Lehninger, *Biochemistry: The Molecular Basis of Cell Structure and Function*, 2nd ed., 1975, pp. 73-75, Worth Publishers, New York.
Lei, Jianqing et al., Potential antitumor applications of a monoclonal antibody specifically targeting human papilloma virus 16 E749-57 peptide, Microbiology and Immunology, 2012, vol. 56, pp. 456-462.
Lemieux, R. U. et al., Halide ion catalyzed glycosidation reactions. Syntheses of a-linked disaccharides. J Am. Chem. Soc. 97(14), 4056-62, (1975).
Leung et al., "A method for random mutagenesis of a defined DNA segment using a modified polymerase chain reaction," *Technique—A Journal of Methods in Cell and Molecular Biology*, Aug. 1989, 1(1):11-15.
Lew et al., Discovery and Development of GS 4104 (oseltamivir): an Orally Active Influenza Neuraminidase Inhibitor, Curr Med Chem, Jun. 2000, 7(6):663-672.
Li et al., ß-endorphin omission analogs: Dissociation of Immunoreactivity from other biological activities, Proc Natl Avad Sci USA, 77:3211-3214 (1980).
Li, Y. L. et al., Crystallization and Melting Behaviors of PPC-BS/PVA Blends, 19, 1557-1566, 2003.
Li, Henghui et al., MALDI-MS Analysis of Sialylated N-Glycan Linkage Isomers Using Solid-Phase Two Step Derivatization Method, Analytica Chimica Acta 924 (2016) 77-85.
Li et al., "Design of a potent CD1d-binding NKT cell ligand as a vaccine adjuvant," *Proc. Natl. Acad. Sci. USA*, Jul. 20, 2010, 107:13010-13015.
Li, J.; Hu, M.; Yao, S. Q. "Rapid synthesis, screening, and identification of xanthone and xanthene-based fluorophores using click chemistry." Org. Lett. 2009, 11, 3008-3011.
Li, Lingling, et al., "Syntheses and spectral properties of functionalized, water-soluble BODIPY derivatives." J. Org. Chem. 2008, 73, 1963-1970.
Li, L. et al. Efficient chemoenzymatic synthesis of an N-glycan isomer library. Chem. Sci. 6, 5652-5661 (2015).
Liang, Yuh-Jin et al., Switching of the Core Structures of Glycosphingolipids From Blobo- and Lacto- to Ganglio-Series Upon Human Embryonic Stem Cell Differentiation, PNAS, 107(52), Dec. 2010, 22564-22569.
Liang et al., "Quantitative microarray analysis of intact glycolipid-CD1d interaction and correlation with cell-based cytokine production," *J. Am. Chem. Soc.*, Sep. 17, 2008, 130(37):12348-12354.
Liang, P. H., Wang, S. K. & Wong, C.-H. Quantitative analysis of carbohydrate-protein interactions using glycan microarrays: Deter-

(56) References Cited

OTHER PUBLICATIONS mination of surface and solution dissociation constants. J. Am. Chem. Soc. 129, 11177-11184, (2007).
Liang, Chi-Hui et al., Iron Oxide/Gold Core/Shell Nanoparticles for Ultrasensitive Detection of Carbohydrate-Protein Interactions, Anal. Chem. 2009; 81, 7750-7756.
Liao, Shih-Fen et al., Immunization of Fucose-Containing Polysaccharides From Reishi Mushroom Induces Antibodies to Tumor-Associated Globo H-Series Epitopes, Proceedings National Academy of Sciences PNAS, vol. 110, No. 34, Aug. 1, 2013, pp. 13809-13814.
Lin et al., A common glycan structure on immunoglobulin G for enhancement of effector functions, PNAS, Aug. 25, 2015, vol. 112, No. 34, p. 10611-10616.
Lindmark et al., "Binding of immunoglobulins to protein A and immunoglobulin levels in mammalian sera," *J. Immunol. Meth.*, Aug. 12, 1983, 62(1):1-13.
Liu C, et al., "Expansion of spleen myeloid suppressor cells represses NK cell cytotoxicity in tumor-bearing host" *Blood*. May 15, 2007;109(10):4336-42. Epub Jan. 23, 2007.
Liu et al., "Activity-based protein profiling: the serine hydrolases," *Proc. Natl. Acad. Sci. USA*, Dec. 21, 1999, 96(26):14694-14699.
Liu et al., "Eradication of large colon tumor xenografts by targeted delivery of maytansinoids," *Proc. Natl., Acad. Sci. U.S.A.*, Aug. 6, 1996, 93(16):8618-8623.
Liu et al., Enhanced anti-influenza agents conjugated with anti-inflammatory activity. J Med Chem. Oct. 11, 2012;55(19):8493-501.
Liu et al., Intramolecular ion-pair prodrugs of znamivir nad guanidino-oseltamivir. Bioorganic & Medicinal Chemistry. Jun. 2011; 19(16):4796-4802.
Liu et al., Synthesis and anti-influenza activities of carboxyl alkoxyalkyl esters of 4-guanidino-Neu5Ac2en (zanamivir). Bioorg Med Chem Lett. Sep. 1, 2007;17(17):4851-4. Epub Jun. 20, 2007.
LoBuglio et al., "Mouse/human chimeric monoclonal antibody in man: kinetics and immune response," *Proc. Natl. Acad. Sci. U.S.A.*, Jun. 1989, 86(11):4220-4224.
Lode et al., "Targeted therapy with a novel enediyene antibiotic calicheamicin $\Theta^I{}_1$ effectively suppresses growth and dissemination of liver metastases in a syngeneic model of murine neuroblastoma," *Cancer Res.*, Jul. 15, 1998, 58(14):2925-2928.
Lonberg et al., "Antigen-specific human antibodies from mice comprising four distinct genetic modifications," *Nature*, Apr. 28, 1994, 368(6474):856-859.
Lonberg et al., "Human antibodies from transgenic mice," *Int. Rev. Immunol.*, 1995, 13(1):65-93.
Lopes, J.F. et al., Simulataneous Chromatographic Separation of Enantiomers, Anomers and Structural Isomers of Some Biologically Relevant Monsaccharides. J. Chomatogr. A, (2008) 1188:34-42.
Lou, et al., Stage-specific embryonic antigent-4 as a potential therapeutic target in glioblastoma multiforms and other cancers. Proc Natl Acad Sci USA 2014, 111(7):2482-7.
Loudet, A.; Burgess, K. "BODIPY dyes and their derivatives: syntheses and spectroscopic properties." Chem. Rev. 2007, 107, 4891-4932.
Louis et al., "The 2007 WHO classification of tumours of the central nervous system," *Acta. Neuropathol.*, Aug. 2007, 114(2):97-109.
Lu et al., "Design of a mechanism-based probe for neuraminidase to capture influenza viruses," *Angew. Chem. Int. Ed. Engl.*, Oct. 28, 2005, 44(42):6888-6892.
Lu, Guokai et al., Reactivity-Based One-Pot Synthesis of Immunosuppressive Glycolipids From the Caribbean Sponge Plakortis Simplex, J. Chem. 2009, 27, 2217-2222.
Lu et al., "Single chain anti-c-Met antibody conjugated nanoparticles for in vivo tumor-targeted imaging and drug delivery," *Biomaterials*, Apr. 2011, 32(12):3265-3274.
MacBeath, G. and Schreiber, S. L., Printing Proteins as Microarrays for High-Throughput Function Determination, Science, 289, 1760-1763, 2000.

MacFarlane GT, et al., "Formation of glycoprotein degrading enzymes by Bacteroides fragilis" *FEMS Microbiol Lett*. Jan. 15, 1991;61(2-3):289-93.
Makino et al., Predominant expression of invariant $V_{\alpha 14}{}^+$ TCR $\alpha$ chain in NK1.1$^+$ T cell populations, *Int. Immunol.*, Jul. 1995, 7(7):1157-1161.
Mandler et al., "Immunoconjugates of geldanamycin and anti-HER2 monoclonal antibodies: antiproliferative activity on human breast carcinoma cell lines," *J. Nat. Cancer Inst.*, Oct. 4, 2000, 92(19):1573-1581.
Mandler et al., "Modifications in synthesis strategy improve the yield and efficacy of geldanamycin-herceptin immunoconjugates," *Bioconjugate Chem.*, Jul.-Aug. 2002, 13(4):786-791.
Mandler et al., "Synthesis and evaluation of antiproliferative activity of a geldanamycin-Herceptin™ immunoconjugate," *Bioorganic & Med. Chem. Letters*, May 15, 2000, 10(10):1025-1028.
Mandal, M., Dudkin, V. Y., Geng, X. & Danishefsky, S. J. In pursuit of carbohydrate-based HIV vaccines, part I: The total synthesis of hybrid-type gp 120 fragments. Angew. Chem. Int. Ed. 43, 2557-2561, (2004).
Månsson et al., "Characterization of new gangliosides of the lactotetraose series in murine xenografts of a human glioma cell line," *FEBS Lett.*, May 26, 1986, 201(1):109-113.
Marasco et al., "Design, intracellular expression, and activity of a human anti-human immunodeficiency virus type 1 gp120 single-chain antibody," *Proc. Natl. Acad. Sci. U.S.A.*, Aug. 15, 1993, 90(16):7889-7893.
Marasco, "Intrabodies: turning the humoral immune system outside in for intracellular immunization," *Gene Therapy*, Jan. 1997, 4(1):11-15.
Marcato et al., "Chapter 17: The Rocky Road from Cancer Stem Cell Discovery to Diagnostic Applicability," Cancer Stem Cells Theories and Practice, pp. 335-360, Mar. 22, 2011.
Marks et al., "By-passing immunization. Human antibodies from V-gene libraries displayed on phage," *J. Mol. Biol.*, Dec. 5, 1991, 222(3):581-597.
Marks et al., "By-passing immunization: Building high affinity human antibodies by chain shuffling," *Nature Biotechnology*, Jul. 1992, 10(7):779-783.
Massart, R., IEEE Transactions on Magnetics, 17, 1247 (1981).
Masuko, T. et al., Thiolation of Chitosan. Attachment of Proteins Via Thioether Formation, Biomacromolecules 2005, 6, 880-884.
Mather et al., "Culture of testicular cells in hormone-supplemented serum-free medium," *Annals N.Y. Acad. Sci.*, 1982, 383:44-68.
Mather, "Establishment and characterization of two distinct mouse testicular epithelial cell lines," *Biol. Reprod.*, Aug. 1980, 23(1):243-252.
Matrosovich M, et al., The Surface Glycoproteins of H5 Influenza Viruses Isolated From Humans, Chickens, and Wild Aquatic Birds Have Distinguishable Properties, J. Virol. 1999, 73, 1146-1155.
Matsuda et al., "Structure and physical map of 64 variable segments in the 3' 0.8-megabase region of the human immunoglobulin heavy-chain locus," *Nature Genet.*, Jan. 1993, 3(1):88-94.
Matz et al., "Fluorescent proteins from nonbioluminescent *Anthozoa* species," *Nat. Biotechnol.*, Oct. 1999, 17(10):969-973.
McCafferty et al., "Phage antibodies: Filamentous phage displaying antibody variable domains," *Nature*, Dec. 6, 1990, 348:552-554.
McKimm-Breschkin et al., "Tethered neuraminidase inhibitors that bind an influenza virus: a first step towards a diagnostic method for influenza," Angew. Chem. Int. Ed Engl., Jul. 14, 2003, 42(27):3118-3121.
McKimm-Breschkin, "Resistance of influenza viruses to neuraminidase inhibitors—a review," Antiviral Res., Jul. 2000, 47(1): 1-17.
McKimm-Breschkin, J. et al., "Neuraminidase Sequence Analysis and Susceptibilities of Influenza Virus Clinical Isolates to Zanamivir and Oseltamivir," Antimicrobial Agents and Chemotherapy, vol. 47, No. 7, Jul. 2003, in 10 pages.
Meezan et al., "Comparative studies on the carbohydrate-containing membrane components of normal and virus-transformed mouse fibroblasts: II: Separation of glycoproteins and glycopeptides by Sephadex chromatography," *Biochemistry*, Jun. 1969, 8(6):2518-2524.

(56) References Cited

OTHER PUBLICATIONS

Medelson et al., NKp46 O-glycan Sequences that are involved in the interaction with Hemagglutinin Type 1 of Influenza Virus. J. Virol. Feb. 10, 2010, 84(8):3789-3797.
McLellan, J. S. et al. Structure of HIV-I gp120 V1/V2 domain with broadly neutralizing antibody PG9. Nature 480, 336-343, 2011.
Merck, MAB4304, Anti-Stage-Specific Embryonic Antigen-4 Antibody, Clone MC-813-70, 4 Pages, 2017.
Meyer, "Malignant gliomas in adults," *N. Engl. J. Med.*, Oct. 23, 2008, 359(17):1850.
Milstein, C & Cuello, AC, Hybrid Hydridomas and their use in immunohistochemistry, Nature 305, 537-540, Oct. 1993.
Mimura et al., "Role of oligosaccharide residues of IgG1-Fc in FcγRIIb binding," *J. Biol. Chem.*, Dec. 7, 2001, 276(49):45539-45547.
Mishima et al., "Growth suppression of intracranial xenografted glioblastomas overexpressing mutant epidermal growth factor receptors by systemic administration of monoclonal antibody (mAb) 806, a novel monoclonal antibody directed to the receptor," *Cancer Res.*, Jul. 15, 2001, 61(14):5349-5354.
Miyagi et al., "Mammalian sialidases: Physiological and pathological roles in cellular functions," *Glycobiology*, Jul. 2012, 22(7):880-896.
Miyagi et al., "Plasma membrane-associated sialidase as a crucial regulator of transmembrane signalling," *J. Biochem.*, Sep. 2008, 144(3):279-285.
Miyagi et al., "Sialidase and malignancy: a minireview," *Glycoconj. J.*, 2004, 20(3):189-198.
Miyagi, "Aberrant expression of sialidase and cancer progression," *Proc. Jpn. Acad. Ser. B. Phys. Biol. Sci.*, 2008(10), 84:407-418.
Miyaji, E. N. et al., Induction of Neutralizing Antibodies Against Diphtheria Toxin by Priming with Recombinant *Mycobacterium bovis* BCG Expressing CRM197, a Mutant Diphtheria Toxin, Infect. Immun. 2001, 69, 869.
Miyamoto et al., "A synthetic glycolipid prevents autoimmune encephalomyelitis by inducing $T_H2$ bias of natural killer T cells," *Nature*, Oct. 4, 2001, 413(6855):531-534.
Moal, E. Le et al., Enhanced Fluorescence Cell Imaging with Metal-Coated Slides, Biophysical Journal, vol. 92, 2150-2161, Mar. 2007.
Monti et al., "Sialidases in vertebrates: a family of enzymes tailored for several cell functions," *Adv. Carbohydr. Chem. Biochem.*, 2010, 64:403-479.
Moody, M. D. et al., Array-based ELISAs for High-Throughput Analysis of Human Cytokines. Biotechniques (2001), 31, 186-194.
Morelle, W. et al., "The Mass Spectrometric Analysis of Glycoproteins and their Glycan Structures", *Review in Current Analytical Chemistry*, vol. 1, No. 1 (2005), pp. 29-57.
Mori K, et al., "Non-fucosylated therapeutic antibodies: the next generation of therapeutic antibodies" *Cytotechnology*. Dec. 2007;55(2-3):109-14. Epub Oct. 31, 2007.
Morimoto et al., "Single-step purification of F(ab')₂ fragments of mouse monoclonal antibodies (immunoglobulins Gl) by hydrophobic interaction high performance liquid chromatography using TSKgel Phenyl-5PW," *J. Biochem. Biophys. Meth.*, Mar. 1992, 24(1-2):107-117.
Morphy et al., Designed multiple ligands. An emerging drug discovery paradigm. J Med Chem. Oct. 20, 2005;48(21):6523-43.
Morphy et al., From magic bullets to designed multiple ligands. Drug Discov Today. Aug. 1, 2004;9(15):641-51.
Morrison et al., "Chimeric human antibody molecules: mouse antigen-binding domains with human constant region domains," *Proc. Natl. Acad. Sci. U.S.A.*, Nov. 1984, 81(21):6851-6855.
Morrison, "Immunology. Success in specification," *Nature*, Apr. 28, 1994, 368(6474):812-813.
Moscona, "Global transmission of oseltamivir-resistant influenza," N Engl. J Med, Mar. 5, 2009, 360(10):953-956.
Moscona, Oseltamivir Resistance—Disabling Our Influenza Defenses, The New England Journal of Medicine, 2005, vol. 353, pp. 2633-2636.

Mosmann et al., "The expanding universe of T-cell subsets: Th1, Th2 and more," *Immunol. Today*, Mar. 1996, 17(3):138-146.
Mossong et al., "Emergence of oseltamivir-resistant influenza A H1N1 virus during the 2007-2008 winter season in Luxembourg: clinical characteristics and epidemiology," Antiviral Res., Oct. 2009, 84(1):91-94.
Mouquet, H. et al. Complex-type N-glycan recognition by potent broadly neutralizing HIV antibodies. Proc. Natl. Acad. Sci. U. S. A 109, E3268-E3277, (2012).
Munson et al., "Ligand: a versatile computerized approach for characterization of ligand-binding systems," *Anal. Biochem.*, Sep. 1, 1980, 107(1):220-239.
Murphy, C. I. et al. Enhanced expression, secretion, and large-scale purification of recombinant HIV-I gp 120 in insect cell using the baculovirus egt and p67 signal peptides. Protein Expres. Purif. 4, 349-357 (1993).
Muthana, S., Yu, H., Huang, S., and Chen, X. Chemoenzymatic synthesis of size-defined polysaccharides by sialyltransferase-catalyzed block transfer of oligosaccharides. J. Am. Chem. Soc. 129, 11918-11919, (2007).
Natarajan et al, Caffeic acid phenethyl ester is a potent and specific inhibitor of activation of nuclear transcription factor NF-kappa B. Proc Natl Acad Sci USA Aug. 20, 1996;93(17):9090-5.
Neuberger et al., "Recombinant antibodies possessing novel effector functions," *Nature*, Dec. 13-19, 1984, 312(5995):604-608.
Neuberger, "Generating high-avidity human Mabs in mice," *Nature Biotechnol.*, Jul. 1996, 14(7):826.
Ni, Jing et al., Immunoassay Readout Method Using Extrinsic Raman Labels Adsorbed on Immunogold Colloids, Anal. Chem., 1999, 71(21), pp. 4903-4908.
Nicolaou et al., "Calicheamicin $\Theta^I_1$: A rationally designed molecule with extremely potent and selective DNA cleaving properties and apoptosis inducing activity," *Angew. Chem. Intl. Ed. Engl.*, Feb. 1, 1994, 33(2):183-186.
Niculescu-Duvaz et al., "Antibody-directed enzyme prodrug therapy (ADEPT): A review," *Adv. Drg. Del. Rev.*, Jul. 7, 1997, 26(2-3):151-172.
Nieuwenhuis et al., "CD1d-dependent macrophage-mediated clearance of *Pseudomonas aeruginosa* from lung," *Nat. Med.*, Jun. 2002, 8(6):588-593.
Nielsen, U. B. et al., Multiplexed Sandwich Assays in Microarray Format, Journal Immunol. Meth. (2004), 290, 107-120.
Ning, X. et al., Visualizing Metabolically-Labeled Glycoconjugates of Living Cells by Copper-Free and Fast Huisgen Cycloadditions, J. Angew. Chem. Int. Ed. 2008, 47, 2253-2255.
Noto et al., "CD44 and SSEA-4 positive cells in an oral cancer cell line HSC-4 possess cancer stem-like cell characteristics," *Oral Oncol.*, Aug. 2013, 49(8):787-795.
Nowak, MW et al., Nicotinic Receptor Binding Site Probed With Unnatural Amino Acid Incorporation in Intact Cells, Science 268:439, 1995.
Novotný et al., "Structural invariants of antigen binding: comparison of immunoglobulin $V_L$-$V_H$ and $V_L$-$V_L$ domain dimers," *Proc. Natl. Acad. Sci. USA*, Jul. 1985, 82(14):4592-4596.
Oberli, Matthias et al., A Possible Oligosaccharide-Conjugate Vaccine Candidate for Clostridium Difficile is Antigenic and Immunogenic, Chemistry & Biology, vol. 18, No. 5, May 2011, 580-588.
Office Action dated Dec. 3, 2013, from corresponding Chinese Patent Application No. 201180034218.3, 15 total pages.
Office Action dated Oct. 22, 2014, from corresponding Chinese Patent Application No. 201180034218.3, 16 total pages.
O'Garra, "Cytokines induce the development of functionally heterogeneous T helper cell subsets," *Immunity*, Mar. 1998, 8(3):275-283.
Okada, Yoshio et al. Changes in the Expression of Sialyl-Lewisx, a Hepatic Necroinflammation-Associated Carbohydrate Neoantigen, in Human Depatocellular Carcinomas, (1994) Cancer 73, 1811-1816.
Okamura et al., "Interleukin-18: a novel cytokine that augments both innate and acquired immunity," *Adv. Immunol.*, 1998, 70:281-312.

(56) References Cited

OTHER PUBLICATIONS

Olden, Kenneth et al., Carbohydrate Moieties of Glycoproteins: A Re-Evaluation of Their Function, Biochem et Biophys Acta 650:209-232 (1982).
Orlandi et al., "Cloning immunoglobulin variable domains for expression by the polymerase chain reaction," *Proc. Natl. Acad. Sci. U.S.A.*, May 1989, 86(10):3833-3837.
Ørum et al., "Efficient method for constructing comprehensive murine Fab antibody libraries displayed on phage." *Nucleic Acids Res.*, Sep. 25, 1993, 21(19):4491-4498.
Otsubo N, et al., An Efficient and Straightforward Synthesis of Sialyl Lex Glycolipid as a Potent Selectin Blocker[[1]], Carbohydr. Res. 1998, 306, 517-530.
Ottolini et al., Combination anti-inflammatory and antiviral therapy of influenza in a cotton rat model. Pediatr. Pulmonol. 2003:36;290-4.
Oyelaran, 0. & Gildersleeve, J. C. Glycan arrays: recent advances and future challenges. Curr. Opin. Chem. Biol. 13, 406-413, (2009).
Pabst, M. et al., Glycan profiles of the 27 Nglycosylation sites of the HIV envelope protein CN54gp140. Biol. Chem. 393, 719-730, (2012).
Pacino, G. et al., Purification and Characterization of a Breast-Cancer-Associated Glycoprotein Not Expressed in Normal Breast and Identified by Monoclonal Antibody 83D4, Br. J. Cancer, 1991, 63, 390-398.
Pan, Yanbin et al., Synthesis and Immunological Properties of N-Modified GM3 Antigens as Therapeutic Cancer Vaccines, J. Med. Chem., 48(3), 875-883, 2005.
Pancera, M. et al. Crystal structure of PG16 and chimeric dissection with somatically related PG9: structure-function analysis of two quaternary-specific antibodies that effectively neutralize HIV-I. J. Virol. 84, 8098-8110, (2010).
Pancera, M. et al. Structural basis for diverse N-glycan recognition by HIV-I-neutralizing V1-V2-directed antibody PG16. Nat. Struct. Mol. Biol. 20, 804-813, (2013).
Papanastassiou et al., "The potential for efficacy of the modified (ICP 34.5⁻) herpes simplex virus HSV1716 following intratumoural injection into human malignant glioma: a proof of principle study," *Gene Therapy*, Mar. 2002, 9(6):398-406.
Parker, C. A.; Rees, W. T., Correction of Fluorescence Spectra and Measurement of Fluorescence Quantum Efficiency, Analyst 1960, 85, 587-600.
Parrish, M. L. et al., A Microarray Platform Comparison for Neuroscience Applications, J. Neurosci. Methods, 2004, 132, 57-68.
Patricelli et al., "Functional interrogation of the kinome using nucleotide acyl phosphates," *Biochemistry*, Jan. 16, 2007, 46(2):350-358.
Paulson, J. C., Blixt, 0. & Collins, B. E. Sweet spots in functional glycomics. Nat. Chem. Biol. 2, 238-248, (2006).
Pearlman et al., *Peptide and Protein Drug Delivery, Chapter 6: Analysis of Protein Drugs*, Lee, ed., 1991, pp. 247-301, Marcel Dekker Publishing, New York.
Peelle et al., "Characterization and use of green fluorescent proteins from *Renilla mulleri* and *Ptilosarcus guernyi* for the human cell display of functional peptides," *J. Protein Chem.*, Aug. 2001, 20(6):507-519.
Peipp et al., "Antibody fucosylation differentially impacts cytotoxicity mediated by NK and PMN effector cells," *Blood*, 2008, 112(6):2390-2399.
Peiris et al., Re-emergence of fatal human influenza A subtype H5N1disease. Lancet. Feb. 21, 2004 ;363(9409):617-9.
Pejchal, R. et al. A potent and broad neutralizing antibody recognizes and penetrates the HIV glycan shield. Science 334, 1097-1103, (2011).
Pellicci et al., "Differential recognition of CD1d-α-galactosyl ceramide by the Vβ8.2 and Vβ7 semi-invariant NKT T-cell receptors," *Immunity*, Jul. 17, 2009, 31(1):47-59.
Perlmutter, R.M. et al., Subclass Restriction of Murine Anti-Carbohydrate Antibodies, Journal of immunology 1978, 121, 566-572.

Pettit, George et al., Antineoplastic Agents. Part 189. The Absolute Configuration and Synthesis of Natural (−)-Dolastatin 10, J Am Chem Soc. 111:5463-5465 (1989).
Pettit, George et al., Dolastatins 23: Stereospecific Synthesis of Dolaisoleuine, J Chem Soc Perkin Trans. 15:853-858 (1996).
Pettit, George et al., Antineoplastic Agents 365. Dolastatin 10 SAR Probes, Anti-Cancer Drug Design 13:243-277 (1998).
Pettit, Robin et al., Specific Activities of Dolastatin 10 and Peptide Derivatives Against Cryptococcus Neoformans, Antimicrob Agents Chemother. 42:2961-2965 (1998).
Pettit, George et al., The Dolastatins; 18: Stereospecific Synthesis of Dolaproine, Synthesis, 719-725 (1996).
Piizi, G. and Hardinger, S., Stereochemistry: an Introduction, UCLA Chemistry 30A Presentation, Fall 2002, in 40 pages.
Plückthun, "Mono- and bivalent antibody fragments produced in *Escherichia coli*: Engineering, folding and antigen binding," *Immunol. Rev.*, Dec. 1992, 130:151-188.
Plückthun, *Handbook of Experimental Pharmacology, vol. 113: The Pharacology of Monoclonal Antibodies, Chapter 11: Antibodies from Escherichia coli*, Rosenberg et al., eds., 1994, pp. 269-315, Springer-Verlag, Berlin.
Poloukhtine et al., "Selective labeling of living cells by a photo-triggered click reaction," *J. Am. Chem. Soc.*, Nov. 4, 2009, 131(43):15769-15776.
Porcelli, S.A., "Preparation of α-galactosylceramide derivatives as modulators of immunity and autoimmunity," CAPLUS 147:440317 (2007).
Potier et al., "Fluorometric assay of neuraminidase with a sodium ( 4-methylumbelliferyl-alpha-D-N-acetylneuraminate) substrate," Anal. Biochem., Apr. 15, 1979, 94(2):287-296.
Pratt, M. R. & Bertozzi, C. R. Chemoselective ligation applied to the synthesis of a biantennary N-linked glycoform of CD52. J Am. Chem. Soc. 125, 6149-6159, (2003).
Prescher, J. A.; Bertozzi, C.R. "Chemistry in living systems." Nat. Chem. Biol. 2005, 1, 13-21.
Presta et al., "Humanization of an antibody directed against IgE," *J. Immunol.*, Sep. 1, 1993, 151(5):2623-2632.
Presta et al., "Humanization of an anti-vascular endothelial growth factor monoclonal antibody for the therapy of solid tumors and other disorders," *Cancer Res.*, Oct. 15, 1997, 57(20):4593-4599.
Presta, "Antibody engineering," *Curr. Opin. Biotechnol.*, Aug. 1992, 3(4):394-398.
Presta, "Antibody engineering," *Curr. Opin. Struct. Biol.*, Aug. 1992, 2(4):593-596.
Pritchard, L. K. et al. Structural Constraints Determine the Glycosylation of HIV-I Envelope Trimers. Cell Rep. 11, 1604-13, (2015).
Pritchard, Laura et al., Cell- and Protein-Directed Glycosylation of Native Cleaved HIV-I Envelope. J. Virol. 89, 8932-44, (2015).
Proba et al., "Functional antibody single-chain fragments from the cytoplasm of *Escherichia coli*: influence of thioredoxin reductase (TrxB)," *Gene*, Jul. 4, 1995, 159(2):203-207.
Pshezhetsky, M. Potier, J. Biol. Chem. 1996, 271, 28359-28365. Association of N-acetylgalactosamine-6-sulfate sulfatase with the multienzyme lysosomal complex of betagalactosidase, cathepsin A, and neuraminidase. Possible implication for intralysosomal catabolism of keratan sulfate.
Puigbò P, Guzmán E, Romeu A, Garcia-Vallvé S. Optimizer: a web server for optimizing the codon usage of DNA sequences. *Nucleic Acids Res.* Jul. 2007;35(Web Server issue):W126-31. Epub Apr. 16, 2007.
Qi, Jianjun et al., Developing visible fluorogenic 'clickon' dyes for cellular imaging, Bioconjugate Chem. 2011, 22, 1758-1762.
Rabbani, Said et al., Glycosyltransferases: An efficient tool for the enzymatic synthesis of oligosaccharides and derivatives as well as mimetics thereof Chimia 60, 23-27, (2006).
Raju et al., "Synthesis and evaluation of 3"- and 4"-deoxy and -fluoro analogs of the immunostimulatory glycolipid, KRN7000," *Bioorg. Med. Chem. Lett.*, 2009, 19:4122-4125.
Ramm et al., "The periplasmic *Escherichia coli* peptidylprolyl cis, trans-isomerase FkpA. II. Isomerase-independent chaperone activity in vitro," *J. Biol. Chem.*, Jun. 2, 2000, 275(22):17106-17113.

(56) References Cited

OTHER PUBLICATIONS

Rana, G. Kucukayan-Dogu, E. Bengu "Growth of vertically aligned carbon nanotubes over self-ordered nano-porous alumina films and their surface properties" Applied Surface Science, 2012, 258 7112-7117.
Raska, M. et al. Glycosylation patterns of HIV-I gp120 depend on the type of expressing cells and affect antibody recognition. J. Biol. Chem. 285, 20860-20869, (2010).
Ravetch et al., "Divergent roles for Fc receptors and complement in vivo," *Ann. Rev. Immunol.*, 1998, 16:421-432.
Ravetch et al., "Fc receptors," *Annu. Rev. Immunol.*, 1991, 9:457-492.
Reyes et al., "Expression of human β-interferon cDNA under the control of a thymidine kinase promoter from herpes simplex virus," *Nature*, Jun. 17, 1982, 297(5867):598-601.
Riechmann et al., "Reshaping human antibodies for therapy," *Nature*, Mar. 24, 1988, 332(6162):323-327.
Rillahan, C. D. & Paulson, J. C. Glycan microarrays for decoding the glycome. Annu. Rev. Biochem. 80, 797-823, (2011).
Ritamo, Ilja al., Comparison of the Glycosylation of in Vitro Generated Polyclonal Human lgG and Therapeutic Immunoglins, Mol Immunol. Feb. 2014; 57(2): 255-62.
Rogers, GN et al., Single Amino Acid Substitutions in Influenza Haemagglutinin Change Receptor Binding Specificity. Nature, 304:76, 1983.
Rogers, GN et al., Receptor Determinants of Human and Animal Influenza Virus Isolates: Differences in Receptor Specificity of the H3 Hemagglutinin Based on Species of Origin. Virology, 127:361, 1983.
Roguska et al., "Humanization of murine monoclonal antibodies through variable domain resurfacing," *Proc. Natl. Acad. Sci. U.S.A.*, Feb. 1, 1994, 91(3):969-973.
Romagnani, "Induction of $T_H1$ and $T_H2$ responses: a key role for the 'natural' immune response?" *Immunol. Today*, Oct. 1992, 13(10):379-381.
Roos et al., "Specific inhibition of the classical complement pathway by C1q-binding peptides," *J. Immunol.*, Dec. 15, 2001, 167(12):7052-7059.
Rosenstein, N.E. et al, Meningococcal Disease, N Engl J Med 2001, 344, 1378-1388.
Rostovtsev et al., "A stepwise Huisgen cycloaddition process catalyzed by copper(I) regioselective ligation of azides and terminal alkynes," *Angew. Chem. Int. Ed. Engl.*, Jul. 15, 2002, 41(41):2596-2599.
Roth, Jurgen et al., Reexpression of Poly(sialic Acid) Units of the Neural Cell Adhesion Molecule in Wilms Tumor, Proc. Natl. Acad. Sci. 85, 2999-3000, 1988.
Rowland et al, "Drug localisation and growth inhibition studies of vindesine-monoclonal anti-CEA conjugates in a human tumour xenograft," *Cancer Immunol. Immunother.*, 1986, 21(3):183-187.
Rudnick et al., Affinity and Avidity in Antibody-Based Tumor Targeting, Can Biotherp & Radoipharm, 24, 155-162 (2009).
Ruiz et al., "IMGT, the international ImMunoGeneTics database," *Nucl. Acids Res.*, Jan. 1, 2000, 28(1):219-221.
Russell et al., "The structure of H5N1 avian influenza neuraminidase suggests new opportunities for drug design," Nature, Sep. 7, 2006, 443(7107):45-49.
Saito, Seiichi et al., Haptoglobin-ß Chain Defined by Monoclonal Antibody RM2 as a Novel Serum Marker for Prostate Cancer, Int. J Cancer, 2008, 123(3), 633-640.
Saito et al., "Expression of globo-series gangliosides in human renal cell carcinoma," *Jpn. J. Cancer Res.*, Jul. 1997, 88(7):652-659.
Saito et al., "Human α2,3-sialyltransferase (ST3Gal II) is a stage-specific embryonic antigen-4 synthase," *J. Biol. Chem.*, Jul. 18, 2003, 278(29):26474-26479.
Saitoh, Osamu et al., Differential Glycosylation and Cell Surface Expression of Lysosomal Membrane Glycoproteins in Sublines of a Human Colon Cancer Exhibiting Distinct Metastatic Potentials, J. Biol. Chem. 267, 5700-5711, 1992.

Sakurama, Haruko et al., Differences in the Substrate Specificities and Active-Site Structures of Two α-L-Fucosidases (Glycoside Hydrolase Family 29) From Bacteroides Thetaiotaomicron, Bioscience Biotechnology Biochemistry, vol. 76, No. 5, May 23, 2012, pp. 1022-1024.
Salisbury et al., "Activity-based probes for proteomic profiling of histone deacetylase complexes," *Proc. Natl. Acad. Sci. USA*, Jan. 23, 2007, 104(4):1171-1176.
Salomon et al., Inhibition of the cytokine response does not protect against lethal H5N1 nfluenza infection. Proc Natl Acad Sci U S A Jul. 24, 2007;104(30): 12479-81.
Sanna, Peitro et al., Directed Selection of Recombinant Human Monoclonal Antibodies to Herpes Simplex Virus Glycoproteins From Phage Display Libraries, Proc. Natl. Acad. Sci., 92:6439 (1995).
Sarkar et al., "Disaccharide uptake and priming in animal cells: inhibition of sialyl Lewis X by acetylated Galβ1→4GlcNAcβ-O-naphthalenemethanol," *Proc. Natl. Acad. Sci. USA*, Apr. 11, 1995, 92(8):3323-3327.
Sastry et al., "Cloning of the immunological repertoire in *Escherichia coli* for generation of monoclonal catalytic antibodies: construction of a heavy chain variable region-specific cDNA library," *Proc. Natl. Acad. Sci. U.S.A.*, Aug. 1989, 86(15):5728-5732.
Sauter, NK et al., Binding of Influenza Virus Hemagglutinin to Analogs of Its Cell-Surface Receptor, Sialic Acid: Analysis by Proton Nuclear Magnetic Resonance Spectroscopy and X-Ray Crystallography. Biochemistry, 31 :9609, 1992.
Sawa, M.; Hsu, T.-L.; Itoh,T.; Sugiyama, M. ; Hanson, S. R. ; Vogt, P. K.; Wong, C.-H. "Glycoproteomic probes for fluorescent imaging of fucosylated glycans in vivo." Proc. Nat. Acad. Sci. US.A., 2006, 103, 12371-12376.
Sawada, Tetsuji et al., E-Selectin Binding by Pancreatic Tumor Cells is Inhibited by Cancer Sera, Int. J. Cancer 57, 901-907, 1994.
Sawada, Ritsuko et al., Differential E-Selectin-Dependent Adhesion Efficiency in Sublines of a Human Colon Cancer Exhibiting Distinct Metastatic Potentials, J. Biol. Chem. 269, 1425-1431, 1994.
Scanlan, C. N. et al., Exploiting the defensive sugars of HIV-I for drug and vaccine design. Nature 446, 1038-1045, (2007).
Schena, M. et al., Quantitative Monitoring of Gene Expression Patterns with a Complementary DNA Microarray, Science, 1995, 270:467-70.
Schengrund et al., "Localization of sialidase in the plasma membrane of rat liver cells," *J. Biol. Chem.*, May 10, 1972, 247(9):2742-2746.
Schenkel-Brunner, Human Blood Groups, Chapter 8: P System, 1995, pp. 211-234, Springer-Verlag, Vienna.
Schier et al., "Identification of functional and structural amino-acid residues by parsimonious mutagenesis," *Gene*, Mar. 9, 1996, 169(2):147-155.
Schmitz, U. et al., Phage Display: A Molecular Tool for the Generation of Antibodies—A Review, Placenta, 21 Suppl. A:S 106 (2000).
Schneider, M.C. et al., Interactions Between Neisseria Meningitidis and the Complement System, Trends Microbial 2007, 15, 233-240.
Schroder et al., The Peptides, vol. 1, p. 76-136, 1965.
Schug, Kevin et al., "Noncovalent binding between guanidinium and anionic groups: focus on biological- and synthetic-based arginine/guanidinium interactions with phosph[on]ate and sulf[on]ate residues," Chem. Rev., Jan. 2005, 105(1):67-113.
Schweitzer, Barry et al., Multiplexed Protein Profiling on Microarrays by Rolling-Circle Amplification, Nat. Biotechnol. (2002), 20, 359-365.
Scurr, D. J. et al. Surface characterization of carbohydrate microarrays. Langmuir 26, 17143-17155, (2010).
Sell, "Cancer-associated carbohydrates identified by monoclonal antibodies," *Hum. Pathol.*, Oct. 1990, 21(10):1003-1019.
Serna, S. et al., Construction of N-Glycan Microarrays by Using Modular Synthesis and On-Chip Nanoscale Enzymatic Glycosylation. Chem. Eur. J 16, 13163-13175, (2010).
Severi et al., "Sialic acid utilization by bacterial pathogens," *Microbiology*, Sep. 2007, 153(Pt 9):2817-2822.

(56) References Cited

OTHER PUBLICATIONS

Seyrantepe et al., "Neu4, a novel human lysosomal lumen sialidase, confers normal phenotype to sialidosis and galactosialidosis cells," *J. Biol. Chem.*, Aug. 27, 2004, 279(35):37021-37029.
Shalaby et al., "Development of humanized bispecific antibodies reactive with cytotoxic lymphocytes and tumor cells overexpressing the HER2 protooncogene," *J. Exp. Med.*, Jan. 1, 1992, 175(1):217-225.
Sheu et al., "Surveillance for neuraminidase inhibitor resistance among human influenza A and B viruses circulating worldwide from 2004 to 2008," *Antimicrob. Agents Chemother.*, Sep. 2008, 52(9):3284-3292.
Shevinsky, LH et al., Monoclonal Antibody to Murine Embryos Defines a Stage-Specific Embryonic Antigen Expressed on Mouse Embryos and Human Teratocarinoma Cells., Cell vol. 30, Issue 3, Oct. 1982, pp. 697-705.
Shie, Jiun-Jie et al., "A concise and flexible synthesis of the potent anti-influenza agents tamiflu and tamiphosphor," Angew. Chem. Int. Ed Engl., 2008, 47(31):5788-5791.
Shie, Jiun-Jie et al., An Azido-BODIPY Probe for Glycosylation: Initiation of Strong Fluorescence Upon Triazole Formation, J. Am. Chem. Soc. 2014, 136, 9953-9961.
Shieh, Peyton et al., Fluorogenic Azidofluoresceins for Biological Imaging, J. Am. Chem. Soc. 2012, 134, 17428-17431.
Shields et al., "High resolution mapping of the binding site on human IgG1 for FcγRI, FcγRII, FcγRIII, and FcRn and design of IgG1 variants with improved binding to the FcγR," *J. Biol. Chem.*, Mar. 2, 2001, 276(9):6591-6604.
Shields et al., "Lack of fucose on human IgG1 N-linked oligosaccharide improves binding to human FcγRIII antibody-dependent cellular toxicity," *J. Biol. Chem.*, Jul. 26, 2002, 277(30):26733-26740.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," *J. Biol. Chem.*, Jan. 31, 2003, 278(5):3466-3473.
Shivatare, S. S. et al. Efficient convergent synthesis of bi-, tri-, and tetra-antennary complex type N-glycans and their HIV-1 antigenicity. J. Am. Chem. Soc. 135, 15382-15391, (2013).
Shivatare, S. S. et al., Modular Synthesis of N-Glycans and Arrays for the Hetero-Ligand Binding Analysis of HIV Antibodies, Nature Chemistry, Mar. 7, 2016, vol. 8(4), p. 338-346.
Shriver, Zachary et al., Glycomics: a Pathway to a Class of New and Improved Therapeutics, Nat Rev Drug Disc, 2004, 3, 863-873.
Sidhu et al., "Phage-displayed antibody libraries of synthetic heavy chain complementarity determining regions," *J. Mol. Biol.*, Apr. 23, 2004, 338(2):299-310.
Siebenlist et al., "*E. coli* RNA polymerase interacts homologously with two different promoters," *Cell*, Jun. 1980, 20(2):269-281.
Sieber et al., "Proteomic profiling of metalloprotease activities with cocktails of active-site probes," *Nat. Chem. Biol.*, May 2006, 2(5):274-281.
Simmons et al., "Expression of full-length immunoglobulins in *Escherichia coli*: Rapid and efficient production of aglycosylated antibodies," *J. Immunol. Methods*, May 1, 2002, 263(1-2):133-147.
Sims et al., "A humanized CD18 antibody can block function without cell destruction," *J. Immunol.*, Aug. 15, 1993, 151(4):2296-2308.
Sivakumar, Krishnamoorthy et al., "A fluorogenic 1,3-dipolar cycloaddition reaction of 3-azidocoumarins and acetylenes." Org. Lett. 2004,24, 4603-4606.
Skehel, John et al., Receptor Binding and Membrane Fusion in Virus Entry: The Influenza Hemagglutinin, Ann. Rev Biochem, 69:531, 2000.
Skerra, "Bacterial expression of immunoglobulin fragments," *Curr. Opinion in Immunol.*, Apr. 1993, 5(2):256-262.
Slamon DJ, et al., Human breast cancer: correlation of relapse and survival with amplification of the HER-2/neu oncogene, Science. Jan. 9, 1987; 235(4785):177-82.
Sletten et al., "Bioorthogonal Chemistry: Fishing for Selectivity in a Sea of Functionality," *Angew. Che. Int. Ed. Engl.*, Aug. 27, 2009, 48(38):6974-6998.
Smith RA et al., "The active form of tumor necrosis factor is a trimer" *J Biol Chem.* May 25, 1987;262(15):6951-4.
Smyth MJ, et al., "CD4+CD25+ T regulatory cells suppress NK cell-mediated immunotherapy of cancer" *J Immunol.* Feb. 1, 2006;176(3):1582-7.
Sok, Devin et al., SnapShot: Broadly Neutralizing Antibodies. Cell 155, 728-728, (2013).
Solomons, G. and Fryhle, C., Chapter 5 Titled, Stereochemistry: Chiral Molecules, p. 184-228, in "Organic Chemistry," 7th Edition, Wiley, Jun. 18, 2001.
Soriano del Amo, David et al. Chemoenzymatic synthesis of the sialyl Lewis X glycan and its derivatives. Carbohydr. Res. 345, 1107-13, (2010).
Spinosa, Maria Rita et al., The Neisseria Meningitidis Capsule is Important for Intracellular Survival in Huamn Cells, Infect Immun 2001, 75, 3594-3603.
Srinivasan, Quantitative et al., Biochemical Rationale for Differences in Transmissibility of 1918 Pandemic Influenza A Viruses, Proc. Natl. Acad. Sci., 105, 2800-2805, 2008.
Stein, K.E. et al., The Immune Response to an Isomaltohexosyl-Protein Conjugate, a Thymus-Dependent Analogue of Alpha(1 Replaced by 6) Dextran., J Immunol 1982, 128, 1350-1354.
Stein, K.E., Thymus-Independent and Thymus-Dependent Responses to Polysaccharide Antigens, J Infect Dis 1992, 165 Suppl 1, S49-52.
Stephens, David, Conquering the Meningococcus, FEALS Microbial Rev 2007, 31, 3-14.
Stephens, D.S. et al., Epidemic Meningitis, Meningococcaemia, and Neisseria Meningitidis, Lancet 2007, 369, 2196-2210.
Stephenson et al., "Neuraminidase inhibitor resistance after oseltamivir treatment of acute influenza A and B in children," Clin. Infect. Dis., Feb. 15, 2009, 48(4):389-396.
Stevanovic, Stefan, Identification of Tumour-Associated T-Cell Epitopes for Vaccine Development, Nat. Rev. Cancer, 2002, 2, 514-520.
Stevens, James et al., Structure of the Uncleaved Human H1 Hemagglutinin From the Extinct 1918 Influenza Virus, Science, 303:1866, 2004.
Stevens, James et al., Structure and Receptor Specificity of the Hemagglutinin From an H5N1 Influenza Virus, Science, 312:404, 2006.
Stevens et al., Glycan Microarry Analysis of the Hemagglutinins From Modern and Pandemic Influenza Viruses Reveals Different Receptor Specificities. Journal of Molecular Biology 355.5 (2006): 1143-1155.
Stickings, Paul et al., Transcutaneous Immunization with Cross-Reacting Material CRM197 of Diphtheria Toxin Boosts Functional Antibody Levels in Mice Primed Parenterally with Adsorbed Diphtheria Toxoid Vaccine, Infection and Immunity, 2008, 76, 1766-1773.
Stockmann, H. et al., Development and Evaluation of New Cyclootynes for Cell Surface Glycan Imaging in Cancer Cells, J. Chem. Sci. 2011, 2, 932-936.
Streicher et al., "Building a successful structural motif into sialylmimetics-cyclohexenephosphonate monoesters as pseudo-sialosides with promising inhibitory properties," Bioorg. Med Chem., Feb. 15, 2006, 14(4):1047-1057.
Stubbs et al., "Synthesis and use of mechanism-based protein-profiling probes for retaining β-D-glucosaminidases facilitate identification of *Pseudomonas aeruginosa* NagZ," *J. Am. Chem. Soc.*, Jan. 9, 2008, 130(1):327-335.
Su, G. Hahner, W. Zhou "Investigation of the pore formation in anodic aluminum oxide" J Mater. Chem. 2008, 18 5787-5795.
Sun, B., Srinibasan, B., Huang, X., Pre-activation-based one-pot synthesis of an alpha-(2,3)-sialylated core-fucosylated complex type bi-antennary N-glycan dodecasaccharide. Chem. Eur. J 14 (23), 7072-81, (2008).
Supplementary European Search Report in European Application No. EP 13775664.9, dated Oct. 27, 2015, in 7 pages.
Suresh et al., "Bispecific monoclonal antibodies from hybrid hybridomas," *Methods in Enzymology*, 1986, 121:210-228.

(56) References Cited

OTHER PUBLICATIONS

Sutton, VR et al., Bcl-2 Prevents Apoptosis Induced by Perforin and Granzyme B, But Not That Mediated by Whole Cytotoxic Lymphocytes, J of Immunology 1997, 158(12), 5783.
Suzuki E, et al., "A nonfucosylated anti-HER2 antibody augments antibody-dependent cellular cytotoxicity in breast cancer patients" *Clin Cancer Res.* Mar. 15, 2007;13(6):1875-82.
Svennerholm et al., "Human brain gangliosides: Developmental changes from early fetal stage to advanced age," *Biochim. Biophys. Acta*, Sep. 25, 1989, 1005(2):109-117.
Syrigos et al., "Antibody directed enzyme prodrug therapy (ADEPT): a review of the experimental and clinical considerations," *Anticancer Research*, Jan.-Feb. 1999, 19(1A):605-614.
Tahir et al., "Loss of IFN-γ production by invariant NK T cells in advanced cancer," *J. Immunol.*, Oct. 1, 2001, 167(7):4046-4050.
Takakura, Yoshimitsu et al., Molecular cloning, expression and properties of an alpha/beta-Galactoside alpha 2,3-sialyltransferase from *Vibrio* sp. JT-FAJ-16. J. Biochem. 142, 403-412, (2007).
Takano, Ryo et al., Sialylation and Malignant Potential in Tumour Cell Glycosylation Mutants, Glycobiology 4, 665-674 (1994).
Takeda et al., "Construction of chimaeric processed immunoglobulin genes containing mouse variable and human constant region sequences," *Nature*, Apr. 4-10, 1985, 314(6010):452-454.
Taki, Takao et al., Glycolipids of Metastatic Tissue in Liver From Colon Cancer: Appearance of Sialylated Lex and Lex Lipids, J. Biochem. 103, 998-1003, 1998.
Talmadge et al., Murine models to evaluate novel and conventional therapeutic strategies for cancer, Am. J. Pathol, 170(3): 793-804 (2007).
Tanaka, Hiroshi et al., An Efficient Convergent Synthesis of GP1c Ganglioside Epitope, J Am Chem Soc. 2008, 130, 17244.
Tanaka, Katsunori et al., Synthesis of a Sialic Acid Containing Complex-Type N-Glycan on a Solid Support, Chemistry—an Asian Journal, 2009, vol. 4 (4), p. 574-580.
Taton, T. Andrew et al., Scanometric DNA Array Detection with Nanoparticle Probes, Science 289 (2000) 1757-1760.
Taton, T. Andrew et al., Two-Color Labeling of Oligonucleotide Arrays Via Size-Selective Scattering of Nanoparticle Probes, J. Am. Chem. Soc. (2001), 123, 5164-5165.
Taylor-Papadimitriou et al., "Exploiting altered glycosylation patterns in cancer: Progress and challenges in diagnosis and therapy," *Trends Biotechnol.*, Jun. 1994, 12(6):227-233.
Telford et al., "The Aspergillus Fumigatus Sialidase is a 3'-Deoxy-D-galacto-2-nonulosonic Acid Hydrolase (KDNase)," The Journal of Biological Chemistry, 286(12), 10783-10792 (Mar. 25, 2011).
"The Human Protein Atlas", B3GALT5 URL:http://www.proteinatlas.org/ENSG00000183778-B3GALT5/cancer, Sep. 9, 2015.
Thorpe, (1985) "Antibody Carriers of Cytotoxic Agents in Cancer Therapy: A Review," in *Monoclonal Antibodies '84: Biological and Clinical Applications*, A. Pinchera et al. (ed.s), pp. 475-506.
Thurber, Greg et al., Antibody Tumor Penetration: Transport Opposed by Systemic and Antigen-Mediated Clearance, Adv Drug Deliv Rev, 60: 1421-1434, 2008.
Toba, et al., "Synthesis and biological evaluation of truncated α-glaactosylceramide derivatives focusing on cytokine induction profile," Bioorganic & Medicinal Chemistry 20(2012): 2850-2859.
Tomlinson et al., "The repertoire of human germline $V_H$ sequences reveals about fifty groups of $V_H$ segments with different hypervariable loops," *J. Mol. Biol.*, Oct. 5, 1992, 227(3):776-798.
Torres-Sanchez et al., "Synthesis and Biological Evaluation of Phophono Analogues of Capsular Polysaccharide Fragments From Neisseria Meningtitidis A" Chem Eur J (2007) vol. 13, pp. 6623-6635.
Toshima, K. Glycosyl fluorides in glycosidations. Carbohydr. Res. 327, 15-26 (2000).
Traunecker et al., "Bispecific single chain molecules (Janusins) target cytotoxic lymphocytes on HIV infected cells," *EMBO J.*, Dec. 1991, 10(12):3655-3659.
Traylor et al., "Gangliosides of human cerebral astrocytomas," *J. Neurochem.*, Jan. 1980, 34(1):126-131.
Trinchieri, "Interleukin-12: a proinflammatory cytokine with immunoregulatory functions that bridge innate resistance and antigen-specific adaptive immunity," *Annu. Rev. Immunol.*, 1995, 13:251-276.
Tsai et al., "Design and synthesis of activity probes for glycosidases," *Org. Lett.*, Oct. 17, 2002, 4(21):3607-3610.
Tsai, Charng-sheng et al., Development of Trifunctional Probes for Glycoproteomic Analysis, Chem. Commun. 2010, 46, 5575-5577.
Tsai TI, et al., "Effective sugar nucleotide regeneration for the large-scale enzymatic synthesis of Globo H and SSEA4" *J Am Chem Soc.* Oct. 2, 2013;135(39):14831-9, Epub Sep. 17, 2013.
Tsai, Charng-Sheng et al., Cell-Permeable Probe for Identification and Imaging of Sialidases, PNAS, vol. 110, No. 7, 2013, 2466-2471.
Tsai, Tsung-I et al., An Effective Bacterial Ducosidase for Glycoprotein Remodeling, ACS Chemical Biology, vol. 12, No. 1, Jan. 20, 2017, pp. 63-72.
Tseng, Susan Y. et al., Glycan Arrays on Aluminum Coated Glass Slides. Chem. Asian J, 2008, 3, 1395-1405.
Tsuji, et al., "Preparation of glycolipids and analogs as antigens for NKT cells for use in vaccines and immunotherapy," CAPLUS 149:492050 (2008).
Tsukamoto, Hiroshi et al., *Photobacterium* sp. JT-ISH-224 produces two sialyltransferases, alpha-/beta-galactoside alpha2,3-sialyltransferase and betagalactoside alpha2,6-sialyltransferase. J. Biochem. 143, 187-197, 2008.
Tumpey, Terrence et al., Characterization of the Reconstructed 1918 Spanish Influenza Pandemic Virus, Science, 310:77, 2005.
Tutt et al., "Trispecific F(ab')₃ derivatives that use cooperative signaling via the TCR/CD3 complex and CD2 to activate and redirect resting cytotoxic T cells," *J. Immunol.*, Jul. 1, 1991, 147(1):60-69.
Tyagarajan K et al., "Exoglycosidase purity and linkage specificity: assessment using oligosaccharide substrates and high-pH anion-exchange chromatography with pulsed amperometric detection" *Glycobiology.* Jan. 1996;6(1):83-93.
Tzeng, Y. L. et al, Epidemiology and Pathogenesis of Neisseria Meningitidis, Microbes Infect 2000, 2, 687-700.
Uchida, Tsuyoshi et al., Diphtheria Toxin and Related Proteins, J Biol. Chem. 218; 3838-3844 (1973).
Udommaneethanakit et al., "Dynamic behavior of avain influenza A virus neuraminidase subtype H5N1 in complex with oseltamivir, zanamivir, peramivir, and their phosphonate analogues," J Chem. Inf Model, Oct. 2009, 49(10):2323-2332.
Ulevitch, RJ et al., Receptor-Dependent Mechanisms of Cell Stimulation by Bacterial Endotoxin, 1995, Annu. Rev. Immunol., 13: 437.
Ulrich, G.; Ziessel, R.; Harriman, A. "The chemistry of fluorescent bodipy dyes: Versatility unsurpassed." Angew. Chem. Int. Ed. 2008, 47, 1184-1201.
Urlaub et al., "Isolation of Chinese hamster cell mutants deficient in dihydrofolate reductase activity." *Proc. Natl. Acad. Sci. U.S.A.*, Jul. 1980, 77(7):4216-4220.
Valentine MA, et al., "Phosphorylation of the CD20 phosphoprotein in resting B lymphocytes. Regulation by protein kinase C" *J Biol Chem.* Jul. 5, 1989;264(19):11282-7.
van Beek et al., "Increased sialic acid density in surface glycoprotein of transformed and malignant cells—a general phenomenon?" *Cancer Res.*, Nov. 1973, 33(11):2913-2922.
van der Horst et al., "Photoaffinity labeling of a bacterial sialidase with an aryl azide derivative of sialic acid," *J. Biol. Chem.*, Jul. 5, 1990, 265(19), 10801-10804.
Van Hest, Jan C.M. et al., Efficient Introduction of Alkene Functionality Into Proteins in Vivo (1998) FEBS Lett. 428:68.
Vaki, Ajit et al., Symbols Nomenclatures for Glycan Representation, Proteomics. Dec. 2009, 9(24): 5398-5399.
Van Meir et al., "Exciting new advances in neuro-oncology: the avenue to a cure for malignant glioma," *CA Cancer J. Clin.*, May-Jun. 2010, 60(3):166-193.
Van Slambrouck et al., "Clustering of monosialyl-Gb5 initiates downstream signalling events leading to invasion of MCF-7 breast cancer cells," *Biochem. J.*, Feb. 1, 2007, 401(3):689-699.
Varghese et al., Three-dimensional structure of the complex of 4-guanidino-Neu5Ac2en and nfluenza virus neuraminidase. Protein Sci. Jun. 1995;4(6):1081-7.

(56) References Cited

OTHER PUBLICATIONS

Varki, "Glycan-based interactions involving vertebrate sialic-acid-recognizing proteins," Nature, Apr. 26, 2007, 446(7139):1023-1029.
Vasella et al., "Synthesis of a phosphonic acid analogue of N-Acetyl-2,3-didehydro-2-deoxyneuraminic acid, an inhibitor of Vibrio cholerae sialidase," Helv. Chim. Acta, Mar. 13, 1991, 74(2):451-463.
Vaswani et al., "Humanized antibodies as potential therapeutic drugs," Ann. Allergy, Asthma Immunol., Aug. 1998, 81(2):105-116, 119.
Vavricka, Christopher et al., Influenza Neuraminidase Operates Via a Nucleophilic Mechanism and Can Be Targeted by Covalent Inhibitors, Nature Communcations, 4:1491 (2013).
Verhoeyen et al., "Reshaping human antibodies: grafting an antilysozyme activity," Science, Mar. 25, 1988, 239(4847):1534-1536.
Vermeer AW et al., "The thermal stability of immunoglobulin: unfolding and aggregation of a multi-domain protein" Biophys J. Jan. 2000;78(1):394-404.
Vinogradova et al., "Molecular mechanism of lysosomal sialidase deficiency in galactosialidosis involves its rapid degradation," Biochem. J., Mar. 1, 1998, 330(Pt 2.):641-650.
Vippagunta, Sudha et al., Crystalline Solids, Advanced Drug Delivery Reviews 48, 3-26 (2001).
Virji, Mumtaz et al., Pathogenic Neisseriae: Surface Modulation, Pathogenesis and Infection Control, Nat Rev, Microbiol 2009, 7, 274-286.
Vitetta, ES et al., Redesigning Nature's Poisons to Create Anti-Tumor Reagents, Science 23(8): 1098 (1987).
Vocadlo et al., "A strategy for functional proteomic analysis of glycosidase activity from cell lysates," Angew. Chem. Int. Ed. Engl., Oct. 11, 2004, 43(40):5338-5342.
Von Itzstein et al., "Rational design of potent sialidase-based inhibitors of influenza virus replication," Nature, Jun. 3, 1993, 363(6428):418-423.
Voskoglou-Nomikos, Clinical predictive value of the in vitro cell line, human xenograft, and mouse allograft preclinical cancer models, Clin Can Res, 9: 4227-4239 (2003).
Wada et al., "A crucial role of plasma membrane-associated sialidase in the survival of human cancer cells," Oncogene, Apr. 12, 2007, 26(17):2483-2490.
Wagner, R et al., "Functional balance between haemagglutinin and neuraminidase in influenza virus infections," Rev. Med Viral., May-Jun. 2002, 12(3): 159-166.
Walls et al., "Activity-based protein profiling of protein tyrosine phosphatases," Methods Mol. Biol., 2009, 519:417-429.
Walker, L. M. et al. Broad neutralization coverage of HIV by multiple highly potent antibodies. Nature 477, 466-470, (2011).
Wang, Chao et al., Tuning the Optical Properties of BODIPY Dye Through Cu(I) Catalyzed Azide-Alkyne Cycloaddition (CuAAC) Reaction, Sci. China Chemistry 2012, 55, 125-130.
Wang, Zhen et al., Multi-Component One-Pot Synthesis of the Tumor-Associated Carbohydrate Antigen Globo-H Based on Preactivation of Thioglycosyl Donors, J Org. Chem. 2007, 72, 6409.
Wang et al., "Glycan microarray of Globo H and related structures for quantitative analysis of breast cancer," Proc. Natl. Acad. Sci. U.S.A., Aug. 19, 2008, 105(33):11661-11666.
Wang et al., "A continuous colorimetric assay for rhinovirus-14 3C protease using peptide p-nitroanilides as substrates," Anal. Biochem., Oct. 15, 1997, 252(2):238-245.
Wang et al., "Synthesis of Neisseria Meningitidis Serogroup W135 Capsular Oligosaccharides for Immunogenicity Comparison and Vaccine Development" Angew Chem Int Ed (2013) vol. 52, pp. 9157-9161.
Wang, Michael et al., "Mechanism by which mutations at his274 alter sensitivity of influenza A virus NI neuraminidase to oseltamivir carboxylate and zanamivir," Antimicrob. Agents Chemother., Dec. 2002, 46(12):3809-3816.
Wang, D., Liu, S., Trummer, B. J., Deng, C. & Wang, A. Carbohydrate microarrays for the recognition of cross-reactive molecular markers of microbes and host cells. Nat. Biotechnol . 20, 275-281, (2002).
Wang et al., Computational Studies of H5N1 Influenza Virus Resistance to Oseltamivir. Protein Sci. 2009, 18(4): 707-715; p. 713.
Wang, C. C. et al. Glycans on Influenza Hemagglutinin Affect Receptor Binding and Immune Response, Proc. Natl. Acad. Sci. 2009, 106, 18137-18142.
Wang, L. X. Carbohydrate-based vaccines against HIV/AIDS. Acs Sym. Ser. 932, 133-160 (2006).
Wang, L. X. Synthetic carbohydrate antigens for HIV vaccine design. Curr. Opin. Chem. Biol. 17, 997-1005, (2013).
Wang, W. et al. A systematic study of the N-glycosylation sites of HIV-I envelope protein on infectivity and antibody-mediated neutralization. Retrovirology, 10, 14, (2014).
Wang, Zhen et al. A general strategy for the chemoenzymatic synthesis of asymmetrically branched N-glycans. Science 341, 379-383, (2013).
Ward et al., "Binding activities of a repertoire of single immunoglobulin variable domains secreted from Escherichia coli," Nature, Oct. 12, 1989, 341(6242):544-546.
Waterhouse et al., "Combinatorial infection and in vivo recombination: a strategy for making large phage antibody repertoires," Nuc. Acids Res., May 11, 1993, 21(9):2265-2266.
Watts et al., "The Synthesis of Some Mechanistic Probes for Sialic Acid Processing Enzymes and the Labeling of a Sialidase from Trypanosoma Rangeli," Canadian Journal of Chemistry, 82(11), 1581-1588 (2004).
Watts et al., "Trypanosoma cruzi trans-sialidase operates through a covalent sialyl-enzyme intermediate: tyrosine is the catalytic nucleophile," J. Am. Chem. Soc., Jun. 25, 2003, 125(25):7532-7533.
Weibel, Robert et al., Tumor-Associated Membrane Sialoglycoprotein on Human Small Cell Lung Carcinoma Identified by the IgG2a Monoclonal Antibody SWA20, (1988) Cancer Res. 48, 4318-4323.
Wen, Wen Hsien et al., "Synergistic effect of zanamivir-porphyrin conjugates on inhibition of neuraminidase and inactivation of influenza virus," J Med Chem., Aug. 13, 2009, 52(15):4903-4910.
White, Clinton et al., "A sialic acid-derived phosphonate analog inhibits different strains of influenza virus neuraminidase with different efficiencies," J Mol. Biol., Feb. 3, 1995, 245(5):623-634.
Wikstrand et al., "Monoclonal antibody therapy of human gliomas: Current status and future approaches," Cancer Metastasis Rev., 1999, 18(4):451-464.
Wilen et al., "Strategies in optical resolutions," Tetrahedron, 1977, 33(21):2725-2736.
Williams et al., "Cloning and sequencing of human immunoglobulin V lambda gene segments." Eur. J. Immunol., Jul. 1993, 23(7):1456-1461.
Wiltshire, S. et al. Proc. Natl. Acad. Sci. (2000) 97, 10113-10119.
Winter et al., "Making antibodies by phage display technology," Annu. Rev. Immunol., 1994, 12:433-455.
Wiseman, GA et al., Phase I/II 90Y-Zevalin (yttrium-90 Ibritumomab Tiuxetan, IDEC-Y2B8) Radioimmunotherapy Dosimetry Results in Relapsed or Refractory Non-Hodgkin's Lymphoma, Eur Jour Nucl Med 27(7): 766-77 (2000).
Wiseman, Gregory et al., Ibritumomab Tiuxetan Radioimmunotherapy for Patients with Relapsed or Refractory Non-Hodgkin Lymphoma and Mild Thrombocytopenia: a Phase II Multicenter Trial, Blood 99(12): 4336-42 (2002).
Witte et al., "Ultrasensitive in situ visualization of active glucocerebrosidase molecules," Nat. Chem. Biol., Dec. 2010, 6(12):907-913.
Witzig, Thomas et al., Randomized Controlled Trial of Yttrium-90-Labeled Ibritumomab Tiuxetan Radioimmunotherpay Versus Rituximab Immunotherapy for Patients with Relapsed or Refractory Low-Grade, Follicular, or Transformed B-Cell Non-Hodgkin's Lymphoma, J Clin Oncol 20(10):2453-63 (2002).
Witzig, Thomas et al., Treatment with Ibritumomab Tiuxetan Radioimmunotherapy in Patients with Rituximab-Refractory Follicular Non-Hodgkin's Lymphoma, J Clin Oncol 20(15):3262-69 (2002).
Wong et al., α-Galactosyl Ceramide Analogs and Their use as Therapeutic, 2010:50988, 2 Pages.

(56) References Cited

OTHER PUBLICATIONS

Woo et al. Cytokine profiles induced by the novel swine-origin influenza A/HINI virus: mplications for treatment strategies. J Infect Dis. Feb. 1, 2010;201(3):346-53.
Woof et al., "Human antibody-Fc receptor interactions illuminated by crystal structures," *Nat. Rev. Immunol.*, Feb. 2004, 4(2):89-99.
Woyke, Tanja et al., Effect of Auristatin PHE on Microtubule Integrity and Nuclear Localization in Cryptococcus Neoformans, Antimicrob. Agents and Chemother. 45(12):3580-3584 (2001).
Wright et al. Antibody variable region glycosylation: biochemical and clinical effects, Springer Semin Immunopathology, 15:259-273 (1993).
Wu et al., "Avidity of CD1d-ligand-receptor ternary complex contributes to T-helper 1 (Th1) polarization and anticancer efficacy," *Proc. Natl. Acad. Sci. USA*, Oct. 18, 2011, 108(42):17275-17280.
Wu, Xueling et al. Rational design of envelope identifies broadly neutralizing human monoclonal antibodies to HIV-I. Science 329, 856-861, (2010).
Wu, Liangxing et al., Fluorescent Cassettes for Monitoring Three-Component Interactions in Vitro and in Living Cells, Journal of the American Chemical Society (2009), 131(26), 9156-9157.
Wu et al., "Catalytic azide-alkyne cycloaddition: reactivity and applications," Aldrichimica Acta, 2007, 40(1):7-17.
Xie, F.; Sivakumar, K.; Zeng, Q. B.; Bruckman, M. A.; Hodges, B.; Wang, Q. "A fluorogenic 'click' reaction of azidoanthracene derivatives." Tetrahedron 2008, 64, 2906-2914.
Yamaguchi, Kazunori et al., "Evidence for mitochondrial localization of a novel human sialidase (NEU4)," *Biochem. J.*, Aug. 15, 2005, 390(Pt 1):85-93.
Yamane-Ohnuki, Naoko et al., Production of Therapeutic Antibodies with Controlled Fucosylation, mAbs 2009, 1;3:230-236.
Yamashita et al., CS-8958, a prodrug of the new neuraminidase inhibitor R-125489, shows ong-acting anti-influenza virus activity. Antimicrob Agents Chemother. Jan. 2009;53(1): 186-92.
Yamashita, Yoshito et al., Alterations in Gastric Mucin with Malignant Transformation: Novel Pathway for Mucin Synthesis, (1995) J. Natl. Cancer Inst. 87, 441-446.
Yang, JM et al., Alterations of )-Glycan Biosynthesis in Human Colon Cancer Tissues, (1994) Glycobiology 4, 873-884.
Yaniv, Nature 297: 17-18, 1982.
Yansura et al., "Nucleotide sequence selection for increased expression of heterologous genes in *Escherichia coli,*" *Methods: A Companion to Methods in Enzymol.*, Aug. 1992, 4(2):151-158.
Yates AJ et al., Brain Tumors in Childhood. Childs Brain 5(1), 31-39 (1979).
Ye et al., "Stage-specific embryonic antigen 4 expression in epithelial ovarian carcinoma," *Int. J. Gynecol. Cancer*, Aug. 2010, 20(6):958-964.
Yelton et al., "Affinity maturation of the BR96 anti-carcinoma antibody by codon-based mutagenesis." *J. Immunol.*, Aug. 15, 1995, 155(4):1994-2004.
Yguerabide, Juan et al., Light-Scattering Submicroscopic Particles as Highly Fluorescent Analogs and Their Use as Tracer Labels in Clinical and Biological Applications: II. Experimental Characterization, Anal. Biochem. (1998), 262, 157-176.
Ying et al., One-bead-one-inhibitor-one-substrate screening of neuraminidase activity. Chembiochem. Oct. 2005;6(10):1857-65.
Yoshida M, et al. Glycoconjugate J. 1993, 10, 324.
Yoshimoto et al., "$CD4^{pos}$, $NK1.1^{pos}$ T cells promptly produce interleukin 4 in response to in vivo challenge with anti-CD3," *J. Exp. Med.*, Apr. 1, 1994, 179(4):1285-1295.
Yu et al., "Anti-GD2 antibody with GM-CSF, interleukin-2, and isotretinoin for neuroblastoma," *N. Engl. J. Med.*, Sep. 30, 2010, 363(14):1324-1334.
Yuen et al., Human infection by avian influenza A H5N1. Hong Kong Med J. Jun. 2005;1 1(3):189-99.
Zapata et al., "Engineering linear F(ab')$_2$ fragments for efficient production in *Escherichia coli* and enhanced antiproliferative activity," *Protein Eng.*, Oct. 1995, 8(10):1057-1062.
Zarei et al., "Separation and identification of GM1b pathway Neu5Ac- and Neu5Gc gangliosides by on-line nanoHPLC-QToF MS and tandem MS: toward glycolipidomics screening of animal cell lines," *Glycobiology*, Jan. 2010, 20(1):118-126.
Zhang et al., "New cerebrosides from Acanthopanax gracilistylus," CAPLUS 156:225776 (2011).
Zhang, Hai-Long et al., A Novel Combined Conjugate Vaccine: Enhanced Immunogenicity of bFGF with CRM197 as a Carrier Protein, Molecular Medicine Reports, 4, 857-863, 2011.
Zhang et al., "Selection of tumor antigens as targets for immune attack using immunohistochemistry: I. Focus on gangliosides," *Int. J. Cancer*, Sep. 26, 1997, 73(1):42-49.
Zheng et al., Delayed antiviral plus immunomodular treatment still reduces mortality in mice infected by high inoculum of influenza A/H5N1 virus. Proc Natl Acad Sci U S A. Jun. 10, 2008;105(23):8091-6.
Zhou et al., A fluorogenic probe for the copper(I)-catalyzed azide-alkyne ligation reaction: modulation of the fluorescence emission via $^3(n,\pi)$-$^1(\pi,\pi^*)$ inversion, *J. Am. Chem. Soc.*, Jul. 28, 2004, 126(29):8862-8863.
Zhu, X et al., Mass spectrometric characterization of the glycosylation pattern of HIV-gp120 expressed in CHO cells. Biochemistry 39, 11194-11204 (2000).
Zou, et al., Chemoenzymatic synthesis and Fc gamma receptor binding of homogenous glycoforms of antibody Fc to FcIIIa receptor. J Am Chem Soc. 2011, 133(46):18975-91.
Zimmermann et al., Multi-target therapeutics: when the whole is greater than the sum of the parts. Drug Discov Today. Jan. 2007;12(1-2):34-42. Epub Nov. 28, 2006.
Greene, Theodora et al., Protective Groups in Organic Synthesis, pp. 42-51 and 96-100, 1991.
Schelhaas, Michael et al., Protecting Group Strategies in Organic Synthesis, Angew. Chem. Int. Ed. Engl. 1996, 35, 2056-2083.
Unverzagt, Carlo et al., A Double Regio- and Stereoselective Glycosylation Strategy for the Synthesis of N-Glycans, Chem. Eur. J., 2008, 14, 1304-1311.
European Application 14817316.4, Communication pursuant to Article 94(3), dated Apr. 16, 2018, 5 pages.

* cited by examiner

CELL-PERMEABLE PROBES FOR IDENTIFICATION AND IMAGING OF SIALIDASES

CROSS-REFERENCES TO RELATED APPLICATIONS

The present application is a Divisional application of U.S. patent application Ser. No. 14/422,310, filed Feb. 18, 2015, the National Stage Entry of PCT/US2013/055472, filed Aug. 16, 2013, and claims priority to U.S. Provisional Application No. 61/684,751 filed Aug. 18, 2012, both of which are herein incorporated by reference in their entirety.

TECHNICAL FIELD OF THE INVENTION

The invention relates to the field of sialidase diagnosis and imaging. Specifically, the invention relates to target-specific compounds that irreversibly bind viral, bacterial, and mammalian sialidases. More specifically, the invention relates to compounds that covalently bind to active sites of sialidases and are useful for diagnostic and therapeutic functions.

BACKGROUND OF THE INVENTION

Sialidase, also called neuraminidase (NA), is an exoglycosidase that catalyzes the hydrolysis of terminal sialic acid residues from the oligosaccharides of glycoconjugates. Sialidases are widely expressed for various functions. (R. K. Y. M. Saito, *Biochemistry and function of sialidases*, Plenum Press: New York, 1995.) Many pathogens, such as viruses, bacteria, and protozoa, produce sialidases for invasion, nutrition, detachment, and immunological escape. (E. Severi, et al. *Microbiology* 2007, 153, 2817)

Mammalian sialidases also have been implicated in many biological processes, including regulation of cell proliferation/differentiation, modulation of cell adhesion, metabolism, and immunological functions. (T. Angata and A. Varki, *Chem. Rev.* 2002, 102, 439. A. Varki, *Nature* 2007, 446, 1023.) Four types of sialidases have been identified and characterized in mammalians. These sialidases are encoded by different genes and expressed at different intracellular locations as lysosomal (Neu1), cytosolic (Neu2), plasma-membrane (Neu3), and mitochondrial/lysosomal (Neu4) enzymes. Although these enzymes share a common mechanism of actions, they have little overlapped functions, probably due to differences in subcellular distribution, pH optimum, kinetic properties, and substrate specificities. (T. Miyagi and K. Yamaguchi, *Glycobiology* 2012, 22, 880.) The regulation and detailed functions of these enzymes are largely undefined. (E. Monti, et al. *Adv. Carbohydr. Chem. Biochem.* 2010, 64, 403.)

Alterations in sialidase activities have been implicated in different diseases. For example, elevated sialidase activities have been reported in BHK-transformed cells and in human breast/colon cancer tissues. (C. L. Schengrund, et al. *J. Biol. Chem.* 1972, 247, 2742. H. B. Bosmann and T. C. Hall, *Proc. Natl. Acad. Sci. USA* 1974, 71, 1833.) Animal studies also suggest the roles of sialidases in tumorigenic transformation and tumor invasion. Biochemical characterizations of mammalian sialidases suggest that increases in Neu3 are involved in colon, renal, and prostate cancers. Transfection of the Neu3 gene into cancer cells leads to protection against apoptosis by increased Bcl-2 expression and decreased activity of caspase-3/-9. (T. Miyagi, *Proc. Jpn. Acad. Ser. B Phys Biol. Sci.* 2008, 84, 407.)

Furthermore, Neu3 overexpression increases cell motility and invasion by modulation of EGF receptor phosphorylation and Ras activation. (T. Wada, et al. *Oncogene* 2007, 26, 2483. T. Miyagi, et al. *J. Biochem.* 2008, 144, 279.) In contrast to the apparent Neu3 promotion in cancer progressions, other sialidases play roles in cancer reduction through accelerated cell apoptosis, differentiation, and suppression of cell invasion. (T. Miyagi, et al. *Glycoconj. J.* 2004, 20, 189.)

In other aspects, deficiency of the lysosomal sialidase (Neu1) is considered as a major cause for sialidosis, which is an inherited lysosomal storage disease resulting in excessive accumulation of sialylglycoconjugates and development of progressive neurosomatic manifestations. (G. H. Thomas, *Disorders of Glycoprotein Degradation: α-Mannosidosis, β-Mannosidosis, Fucosidosis, and Sialidosis*, 8 ed., McGraw-Hill: New York, 2001.)

Activity-based protein profiling (ABPP) is a functional proteomic technology that uses chemical probes for specific enzymes. (M. J. Evans and B. F. Cravatt, *Chem. Rev.* 2006, 106, 3279.) An ABPP probe is typically composed of two elements: a reactive group and a tag. The reactive group is designed based on the catalytic mechanism of the target enzyme, and it usually contains an electrophile that can covalently link to nucleophilic residues in the enzyme active site. The tag may be either a reporter such as a fluorophore or an affinity label such as biotin. The tag can incorporate an alkyne or azide moiety for subsequent modification by the Cu(I)-catalyzed azide-alkyne [3+2] cycloaddition (CuAAC) to introduce a reporter. (V. V. Rostovtsev, et al. *Angew. Chem. Int. Ed.* 2002, 41, 2596. H. C. Kolb and K. B. Sharpless, *Drug Discov Today* 2003, 8, 1128.)

ABPP probes can be useful tools to monitor specific enzyme changes in association with certain biological states, such as cancerous status, and responses to stimulants. ABPP probes have been developed for many enzyme classes, including serine hydrolases (Y. Liu, et al. *Proc. Natl. Acad. Sci. USA* 1999, 96, 14694. D. Kidd, et al. *Biochemistry* 2001, 40, 4005), cysteine proteases (D. Greenbaum, et al. *Mol. Cell. Proteomics* 2002, 1, 60), protein phosphatases (C. Walls, et al. *Methods Mol. Biol.* 2009, 519, 417. K. A. Kalesh, et al. *Chem. Commun.* 2010, 46, 589), oxidoreductases (G. C. Adam, et al. *Nat. Biotechnol.* 2002, 20, 805), histone deacetylases (C. M. Salisbury and B. F. Cravatt, *Proc. Natl. Acad. Sci. USA* 2007, 104, 1171), kinases (M. P. Patricelli, et al. *Biochemistry* 2007, 46, 350), metalloproteases (S. A. Sieber, et al. *Nat. Chem. Biol.* 2006, 2, 274), and glycosidases. (C. S. Tsai, et al. *Org. Lett.* 2002, 4, 3607. D. J. Vocadlo and C. R. Bertozzi, *Angew. Chem. Int. Ed.* 2004, 43, 5338. K. A. Stubbs, et al. *J. Am. Chem. Soc.* 2008, 130, 327. M. D. Witte, et al. *Nat. Chem. Biol.* 2010, 6, 907.)

Two types of sialidase ABPP probes, the quinone methide and the photoaffinity labeling probes have been reported. (G. T. van der Horst, et al. *J. Biol. Chem.* 1990, 265, 10801. C. P. Lu, et al. *Angew. Chem. Int. Ed.* 2005, 44, 6888. R. Kannappan, et al. *Biol. Pharm. Bull.* 2008, 31, 352.) These probes often have problems in non-specific labeling when used in complex protein samples, such as cell lysates. In addition, these probes cannot be applied to in situ labeling experiments because they are impermeable to cell membranes.

For sialidase profiling under physiological conditions, target-specific and cell-permeable ABPP probes are needed to study sialidase changes in living cells. Recently, Withers and coworkers have used 3-fluorosialyl fluoride as an effective inhibitor against *Trypanosoma cruzi* trans-sialidase (TcTs). (A. G. Watts, et al. *J. Am. Chem. Soc.* 2003, 125, 7532. S. Buchini, et al. *Angew. Chem. Int. Ed.* 2008, 47, 2700.)

SUMMARY OF THE INVENTION

Disclosed herein are mechanism-based irreversible sialidase inhibitors (alkyne-hinged 3-fluorosialyl fluoride compounds such as DFSA) which function by trapping a 3-fluorosialylenzyme intermediate (reporter-inhibitor-enzyme conjugate). These sialidase inhibitors can be conjugated with a detectable tagging moiety for isolation and identification of sialidases. Also provided are ester-protected versions of sialidase inhibitors (such as PDFSA) useful as the cell permeable precursor of sialidase inhibitors to allow cell uptake, identification and imaging in situ of sialidase activities under physiological conditions.

In one aspect, the present disclosure provides novel irreversible sialidase inhibitors of formula (I):

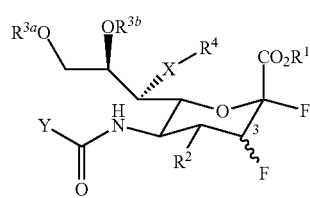

(I)

or a salt thereof,
wherein
F atom at the C3-position is axial or equatorial;
$R^1$ is H or optionally substituted $C_{1-6}$ alkyl;
$R^2$ is $OR^{2O}$, $N_3$, $N(R^{2N})_2$, or guanidine;
each instance of $R^{2O}$ is independently hydrogen, optionally substituted $C_{1-6}$ alkyl, optionally substituted acyl, or an oxygen protecting group;
each instance of $R^{2N}$ is independently hydrogen, optionally substituted $C_{1-6}$ alkyl, optionally substituted acyl, or a nitrogen protecting group;
each instance of $R^{3a}$ and $R^{3b}$ is independently hydrogen, —C(=O)—$R^{3r}$, or an oxygen protecting group;
each instance of $R^{3r}$ is optionally substituted $C_{1-6}$ alkyl, optionally substituted aryl, optionally substituted heteroaryl, or optionally substituted heterocycle, optionally substituted alkylaryl, optionally substituted alkylheteroaryl, or optionally substituted alkylheterocycle;
X is selected from the group consisting of —O—, —O(C=O)—, —NH—, —NH(C=O)—, —(C=O)NH—, —O(C=O)NH—, —O(C=S)NH—, —NH(C=O)NH—, and —NH(C=S)NH—;
$R^4$ is H, optionally substituted $C_{1-6}$ alkyl, or -L-Z;
Y is optionally substituted $C_{1-6}$ alkyl or -L-Z;
each instance of L is independently selected from the group consisting of —(CH$_2$)$_n$—, —(CH$_2$)$_n$C=O—, —(CH$_2$)$_n$NH—, —(C=O)(CH$_2$)$_n$—, —(CH$_2$)$_n$NH(C=O)—, —(C=O)(CH$_2$)$_n$NH(C=O)—, —(CH$_2$)$_n$SCH$_2$(C=O)—, and —(CH$_2$CH$_2$O)$_n$—;
each instance of n is an integer from 1 to 8, inclusive;
each instance of Z is a functional group for further ligation; and provided that the compound is not of the formula

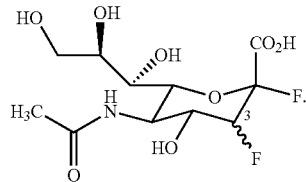 [SMILES: CC(=O)NC1C(O)C(F)C(F)(C(=O)O)OC1[C@H](O)[C@H](O)CO]

In some embodiments of formula (I), Z is optionally substituted alkyne, optionally substituted alkene, halogen, —N$_3$, N(R$^N$)$_2$, OR$^O$, SR$^S$, or CO$_2$R$^O$; wherein each instance of R$^N$ is independently hydrogen, optionally substituted $C_{1-6}$ alkyl, or a nitrogen protecting group; each instance of R$^O$ is independently hydrogen, optionally substituted $C_{1-6}$ alkyl, optionally substituted acyl, or an oxygen protecting group; and each instance of R$^S$ is independently hydrogen, optionally substituted $C_{1-6}$ alkyl, or a sulfur protecting group.

In some embodiments, the compounds of formula (I) are of formula (II-a):

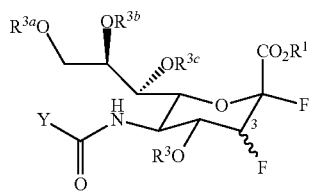

(II-a)

or a salt thereof,
wherein $R^{3c}$ is independently hydrogen, optionally substituted $C_{1-6}$ alkyl, optionally substituted acyl, or an oxygen protecting group.

In some embodiments, the compound of formula (I) of formula (II-b):

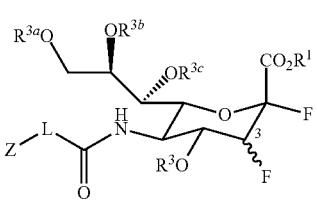

(II-b)

or a salt thereof.

In some embodiments, the compound of formula (I) of formula (II-b1):

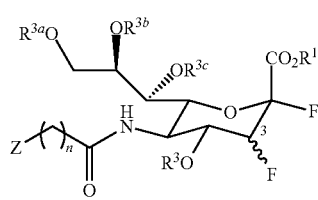

(II-b1)

or a salt thereof.

In some embodiments, the compound of formula (I) of formula (II-b2):

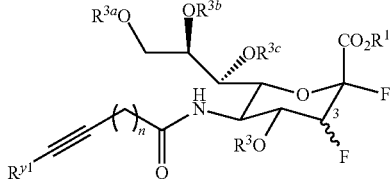
(II-b2)

or a salt thereof, wherein $R^{y1}$ is hydrogen or optionally substituted $C_{1-6}$ alkyl.

In some embodiments, the compound of formula (I) of formula (II-b3):

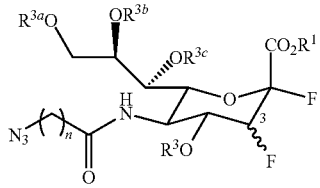
(II-b3)

or a salt thereof.

In some embodiments, the compound of formula (I) of formula (II-c):

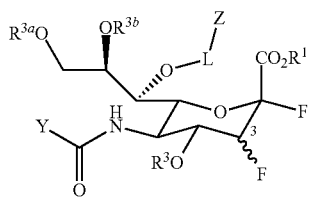
(II-c)

or a salt thereof.

In some embodiments, the compound of formula (I) of formula (II-c1):

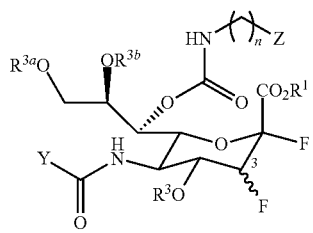
(II-c1)

or a salt thereof.

In some embodiments, the compound of formula (I) of formula (II-c2):

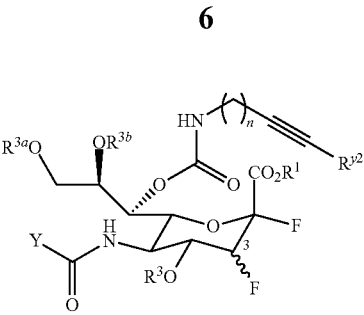
(II-c2)

or a salt thereof, wherein $R^{y2}$ is hydrogen or optionally substituted $C_{1-6}$ alkyl.

In some embodiments, the compound of formula (I) of formula (II-c3):

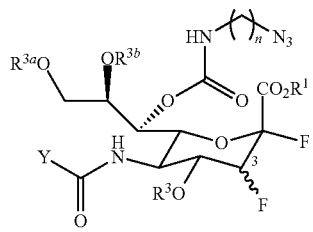
(II-c3)

or a salt thereof.

In some embodiments, the compounds of formula (I) are of formula (II):

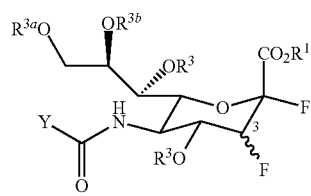
(II)

wherein F atom at the C3-position can locate on either axial or equatorial directions; $R^1$ comprises straight-chain or branched alkyl (C1-C6); each instance of $R^3$ is selected from the group consisting of H and acyl group comprising acetyl ($CH_3CO$), propanoyl ($C_2H_5CO$), butanoyl ($C_3H_7CO$), pivaloyl (t-BuCO), trifluoroacetyl ($CF_3CO$), phenylacetyl ($PhCH_2CO$), benzoyl ($C_6H_5CO$), and (substituted)benzoyl; Y is selected from the group consisting of $CH_3$, $CF_3$, and a moiety L-Z wherein L is a linker and Z is a terminal functional group for further ligation; L is a linking group comprising 1-12 carbon atoms and/or 0-5 heteroatoms selected from N, O and S, selected from the group consisting of —$(CH_2)_n$—, —$(CH_2)_nC$=O, —$(CH_2)_n$NH, —(C=O)$(CH_2)_n$—, —$(CH_2)_n$NH(C=O), —(C=O)$(CH_2)_n$NH(C=O), —$(CH_2)_n$SCH$_2$(C=O), or —$(CH_2CH_2O)_n$—; and n is an integer from 1 to 8; and Z represents any functional group for further ligation. In certain embodiments, Z is selected from the group consisting of alkyne (HC≡C), alkene ($H_2C$=CH), halo (Cl, Br, I), azide ($N_3$), amine ($NH_2$), hydroxyl (OH), thiol (SH), carbonyl (C=O), and carboxyl ($CO_2H$) groups; provided wherein: H at $R^1$, H at $R^3$, and $CH_3$ at Y are not simultaneously present in a compound of formula (II).

In another embodiment, the compound of formula (I) is a compound of formula (V):

(V)

wherein F atom at the C3-position can locate on either axial or equatorial directions; $R^1$ comprises straight-chain or branched alkyl ($C_1$-$C_6$); $R^3$ is selected from the group consisting of H and acyl group comprising acetyl ($CH_3CO$), propanoyl ($C_2H_5CO$), butanoyl ($C_3H_7CO$), pivaloyl (t-BuCO), trifluoroacetyl ($CF_3CO$), phenylacetyl ($PhCH_2CO$), benzoyl ($C_6H_5CO$), and (substituted)benzoyl; X is selected from the group consisting of —O—, —O(C=O), —NH, —NH(C=O), —O(C=O)NH, —O(C=S)NH, —NH(C=O)NH, and —NH(C=S)NH; $R^4$ is selected from the group consisting of H, alkyl (C1-C6), and a moiety L-Z wherein L is a linker and Z is a terminal functional group for further ligation; L is a linking group comprising 1-12 carbon atoms and/or 0-5 heteroatoms selected from N, O and S, selected from the group consisting of —$(CH_2)_n$—, —$(CH_2)_nC$=O, —$(CH_2)_nNH$, —(C=O)$(CH_2)_n$, —$(CH_2)_nNH$(C=O), —(C=O)$(CH_2)_nNH$(C=O), —$(CH_2)_nSCH_2$(C=O), or —$(CH_2CH_2O)_n$—; and n is an integer from 1 to 8; and Z represents any functional group for further ligation. In certain embodiments, Z is selected from the group consisting of alkyne (HC≡C), alkene ($H_2C$=CH), halo (Cl, Br, I), azide ($N_3$), amine ($NH_2$), hydroxyl (OH), thiol (SH), carbonyl (C=O), and carboxyl ($CO_2H$) groups; provided wherein: H at $R^1$, H at $R^3$, O at X, and H at $R^4$ are not simultaneously present in a compound of formula (V).

Exemplary sialidase inhibitors are of the following formulae:

(III)

DFSA-5-yne (VI)

DFSA-7-yne (VIII)

DFSA-5-azide (IV)

PDFSA-5-yne (VII)

PDFSA-7-yne (IX)

PDFSA-5-azide

The invention relates to detectable conjugates comprising a compound of formula (I), (II-a), (II-b), (II-b1), (II-b2), (II-b3), (II-c), (II-c1), (II-c2), (II-c3), or (II)-(IX), with the compound covalently conjugated to a detectable tagging moiety. In certain embodiments, the detectable tagging moiety comprises a reporter group or a label. In certain embodiments, the label is azido-annexed biotin (azido-biotin).

The present disclosure relates to sialidase protein adducts comprising a compound of formula (I), (II-a), (II-b), (II-b1), (II-b2), (II-b3), (II-c), (II-c1), (II-c2), (II-c3), or (II)-(IX), or a detectable conjugate. In certain embodiments of the provided sialidase protein adducts, the sialidase protein is covalently conjugated to the compound or the detectable conjugate.

The present disclosure relates to synthetic sialidase inhibitors that form covalent adducts with virus, bacteria and human sialidases.

The invention relates to detection and imaging of the fluorosialyl-enzyme adducts. As an example, DFSA-5-yne bearing a terminal alkyne group is conjugated with an azido-biotin via a Cu(I)-catalyzed [3+2] cycloaddition (Click reaction) and detected by the streptavidin specific reporting signals.

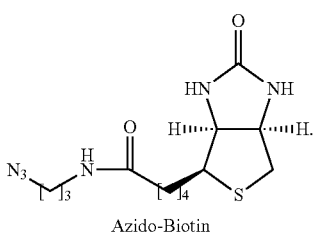
Azido-Biotin
In some embodiments, DFSA-5-yne or DFSA-7-yne is used to diagnose oseltamivir susceptibility in influenza infections by competitively binding the influenza neuraminidase.

In some embodiments, PDFSA-5-yne or PDFSA-7-yne is used for imaging in situ of the changes of sialidase activity within live cells.

These and other aspects will become apparent from the following description of the preferred embodiment taken in conjunction with the following drawings, although variations and modifications therein may be affected without departing from the spirit and scope of the novel concepts of the disclosure.

DEFINITIONS

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry,* 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic," as used herein, refers to alkyl, alkenyl, alkynyl, and carbocyclic groups. Likewise, the term "heteroaliphatic" as used herein, refers to heteroalkyl, heteroalkenyl, heteroalkynyl, and heterocyclic groups.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., $—CH_3$). In certain embodiments, the alkyl group is a substituted $C_{1-10}$ alkyl.

As used herein, "heteroalkyl" refers to an alkyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

As used herein, "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl.

As used herein, "heteroalkenyl" refers to an alkenyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

As used herein, "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

As used herein, "heteroalkynyl" refers to an alkynyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

As used herein, "carbocyclyl" or "carbocyclic" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-10}$ carbocyclyl. In certain embodiments, the carbocyclyl group is a substituted C$_{3-10}$ carbocyclyl.

As used herein, "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("C$_{6-14}$ aryl"). In some embodiments, an aryl group has 6 ring carbon atoms ("C$_6$ aryl"; e.g., phenyl). In some embodiments, an aryl group has 10 ring carbon atoms ("C$_{10}$ aryl"; e.g., naphthyl such as 1-naphthyl and 2-naphthyl). In some embodiments, an aryl group has 14 ring carbon atoms ("C$_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted C$_{6-14}$ aryl. In certain embodiments, the aryl group is a substituted C$_{6-14}$ aryl.

As used herein, "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

As understood from the above, alkyl, alkenyl, alkynyl, heteroalkyl, heteroalkenyl, heteroalkynyl, carbocyclyl, heterocyclyl, aryl, and heteroaryl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$heteroalkynyl, C$_{3-14}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$heteroalkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$ heteroalkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$ heteroalkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{1-6}$ heteroalkyl, C$_{2-6}$ heteroalkenyl, C$_{2-6}$heteroalkynyl, C$_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{1-6}$ heteroalkyl, $C_{2-6}$ heteroalkenyl, $C_{2-6}$ heteroalkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{1-6}$ heteroalkyl, $C_{2-6}$ heteroalkenyl, $C_{2-6}$ heteroalkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$—C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, $C_{1-6}$ heteroalkyl, $C_{2-6}$ heteroalkenyl, $C_{2-6}$ heteroalkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X$^-$ is a counterion.

As used herein, the term "halo" or "halogen" refers to fluorine (fluoro, —F), chlorine (chloro, —Cl), bromine (bromo, —Br), or iodine (iodo, —I).

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl (e.g., aralkyl, heteroaralkyl), $C_{2-10}$ alkenyl, $C_{2-10}$ alkynyl, $C_{1-10}$ heteroalkyl, $C_{2-10}$ heteroalkenyl, $C_{2-10}$ heteroalkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

As used herein, the term "salt" refers to any and all salts, including pharmaceutically acceptable salt which refers to those salts within the scope of sound medical judgment, suitable for use in contact with the tissues of humans and lower animals without undue toxicity, irritation, allergic response and the like, and are commensurate with a reasonable benefit/risk ratio (see Berge et al. describes pharmaceutically acceptable salts in detail in *J. Pharmaceutical Sciences* (1977) 66:1-19). Examples of pharmaceutically acceptable, nontoxic acid salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, "derivative" of a compound refers to solvates, hydrates, polymorphs, co-crystals, tautomers, stereoisomers, isotopically labeled derivatives, prodrugs of the compound.

The term "polymorphs" means crystal structures in which a compound (or a salt, hydrate, or solvate thereof) can crystallize in different crystal packing arrangements, all of which have the same elemental composition. Different crystal forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Crystalline polymorphs of a compound can be prepared by crystallization under different conditions.

The term "co-crystal" refers to a crystalline structure composed of at least two components, where the components may be atoms, ions, or molecules. Typically, the components interact with one another to form the crystalline structure through ionic or, more commonly, non-ionic interactions. For a specific co-crystal form, all its components can be found within a single crystal lattice (unit cell) and are usually in a definite stoichiometric ratio. A component of a co-crystal may be a solid or liquid when the component is in its pure form. Crystalline salts, crystalline hydrates, and crystalline solvates are also within the meaning of co-crystals.

"Solvate" refers to forms of the compound that are associated with a solvent or water (also referred to as a "hydrate"), usually by a solvolysis reaction. This physical association includes hydrogen bonding. Conventional solvents include water, methanol, ethanol, acetic acid, DMSO, THF, diethyl ether, and the like. The compounds of the invention may be prepared, e.g., in crystalline form, and may be solvated or hydrated. Suitable solvates include pharmaceutically acceptable solvates, such as hydrates, and further include both stoichiometric solvates and non-stoichiometric solvates. In certain instances, the solvate will be capable of isolation, for example, when one or more solvent molecules are incorporated in the crystal lattice of the crystalline solid. "Solvate" encompasses both solution-phase and isolable solvates. Representative solvates include hydrates, ethanolates, and methanolates.

"Tautomers" refer to compounds that are interchangeable forms of a particular compound structure, and that vary in the displacement of hydrogen atoms and electrons. Thus, two structures may be in equilibrium through the movement of it electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

As used herein, "isotopically labeled derivatives" of a compound refer to derivatives of the compound wherein at least one atom of the compound is enriched for an isotope that is higher or lower in molecular weight than the most abundant isotope of the atom found in nature.

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offers advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. Particularly the $C_1$ to $C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of the invention.

As used herein, when two entities are "conjugated" or "ligated" to one another they are linked by a direct or indirect covalent or non-covalent interaction. In certain embodiments, the association is covalent. In other embodiments, the association is non-covalent. Non-covalent interactions include hydrogen bonding, van der Waals interactions, hydrophobic interactions, magnetic interactions, electrostatic interactions, etc. An indirect covalent interaction is when two entities are covalently connected, optionally through a linker group.

As used herein, a "label" refers to a moiety that has at least one element, isotope, or functional group incorporated into the moiety which enables detection of the entity to which the label is attached. Labels can be directly attached (ie, via a bond) or can be attached by a linker (e.g., such as, for example, a cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene, or any combination thereof, which can make up a linker). It will be appreciated that the label may be attached to the inventive entity at any position that does not interfere with the biological activity or characteristic of the entity that is being detected.

In general, a label can fall into any one (or more) of five classes: a) a label which contains isotopic moieties, which may be radioactive or heavy isotopes, including, but not limited to, $^2H$, $^3H$, $^{13}C$, $^{14}C$, $^{15}N$, $^{31}P$, $^{32}P$, $^{35}S$, $^{67}Ga$, $^{99m}Tc$ (Tc-99m), $^{111}In$, $^{123}I$, $^{125}I$, $^{169}Yb$, and $^{186}Re$; b) a label which contains an immune moiety, which may be antibodies or antigens, which may be bound to enzymes (e.g., such as horseradish peroxidase); c) a label which is a colored, luminescent, phosphorescent, or fluorescent moieties (e.g., such as the fluorescent label FITC); d) a label which has one or more photoaffinity moieties; and e) a label which has a ligand moiety with one or more known binding partners (such as biotin-streptavidin, FK506-FKBP, etc.).

In certain embodiments, such as in the identification of a biological target, label comprises a radioactive isotope, preferably an isotope which emits detectable particles, such as β particles. In certain embodiments, the label comprises one or more photoaffinity moieties for the direct elucidation of intermolecular interactions in biological systems. A variety of known photophores can be employed, most relying on photoconversion of diazo compounds, azides, or diazirines to nitrenes or carbenes (see, Bayley, H., Photogenerated Reagents in Biochemistry and Molecular Biology (1983), Elsevier, Amsterdam, the entire contents of which are incorporated herein by reference). In certain embodiments of the invention, the photoaffinity labels employed are o-, m- and p-azidobenzoyls, substituted with one or more halogen moieties, including, but not limited to 4-azido-2,3,5,6-tetrafluorobenzoic acid.

In certain embodiments, the label comprises one or more fluorescent moieties. In certain embodiments, the label is the fluorescent label FITC. In certain embodiments, the label comprises a ligand moiety with one or more known binding partners. In certain embodiments, the label comprises the ligand moiety biotin.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal.

A "fluorophore" (or fluorochrome, similarly to a chromophore) is a fluorescent chemical compound that can re-emit light upon light excitation. Fluorophores typically contain several combined aromatic groups, or plane or cyclic molecules with several n bonds.

As used herein the term "sample," "test sample," "biological sample," are used interchangeable. The term sample includes, without limitation, cell cultures or extracts thereof; biopsied material obtained from an animal (e.g., mammal) or extracts thereof; and blood, saliva, urine, feces, semen, tears, or other body fluids or extracts thereof. For example, the term "sample" refers to any solid or fluid sample obtained from, excreted by or secreted by any living organism, including single-celled microorganisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). The sample can be in any form, including a solid material such as a tissue, cells, a cell pellet, a cell extract, cell homogenates, or cell fractions; or a biopsy, or a biological fluid. The biological fluid may be obtained from any site (e.g. blood, saliva (or a mouth wash containing buccal cells), tears, plasma, serum, urine, bile, cerebrospinal fluid, amniotic fluid, peritoneal fluid, and pleural fluid, or cells therefrom, aqueous or vitreous humor, or any bodily secretion), a transudate, an exudate (e.g. fluid obtained from an abscess or any other site of infection or inflammation), or fluid obtained from a joint (e.g. a normal joint or a joint affected by disease such as rheumatoid arthritis, osteoarthritis, gout or septic arthritis). The sample can be obtained from any organ or tissue (including a biopsy or autopsy specimen) or may comprise cells (whether primary cells or cultured cells) or medium conditioned by any cell, tissue or organ. Biological samples may also include sections of tissues such as frozen sections taken for histological purposes. Biological samples also include mixtures of biological molecules including proteins, lipids, carbohydrates and nucleic acids generated by partial or complete fractionation of cell or tissue homogenates. Although the sample is preferably taken from a human subject, biological samples may be from any animal, plant, bacteria, virus, yeast, etc. The term animal, as used herein, refers to humans as well as non-human animals, at any stage of development, including, for example, mammals, birds, reptiles, amphibians, fish, worms and single cells. Cell cultures and live tissue samples are considered to be pluralities of animals. In certain exemplary embodiments, the non-human animal is a mammal (e.g., a rodent, a mouse, a rat, a rabbit, a monkey, a dog, a cat, a sheep, cattle, a primate, or a pig). An animal may be a transgenic animal or a human clone. If desired, the biological sample may be subjected to preliminary processing, including preliminary separation techniques.

As used herein "inhibition", "inhibiting", "inhibit" and "inhibitor", and the like, refer to the ability of a compound to reduce, slow, halt, or prevent the activity of a particular biological process involving Ras in a cell relative to vehicle.

As used herein, the term "cell" in the context of the in vivo applications of the invention is meant to encompass eukaryotic and prokaryotic cells of any genus or species, with mammalian cells being of particular interest. "Cell" is also meant to encompass both normal cells and diseased cells, e.g., cancerous cells. In many embodiments, the cells are living cells.

DETAILED DESCRIPTION OF THE INVENTION

Figure 1:
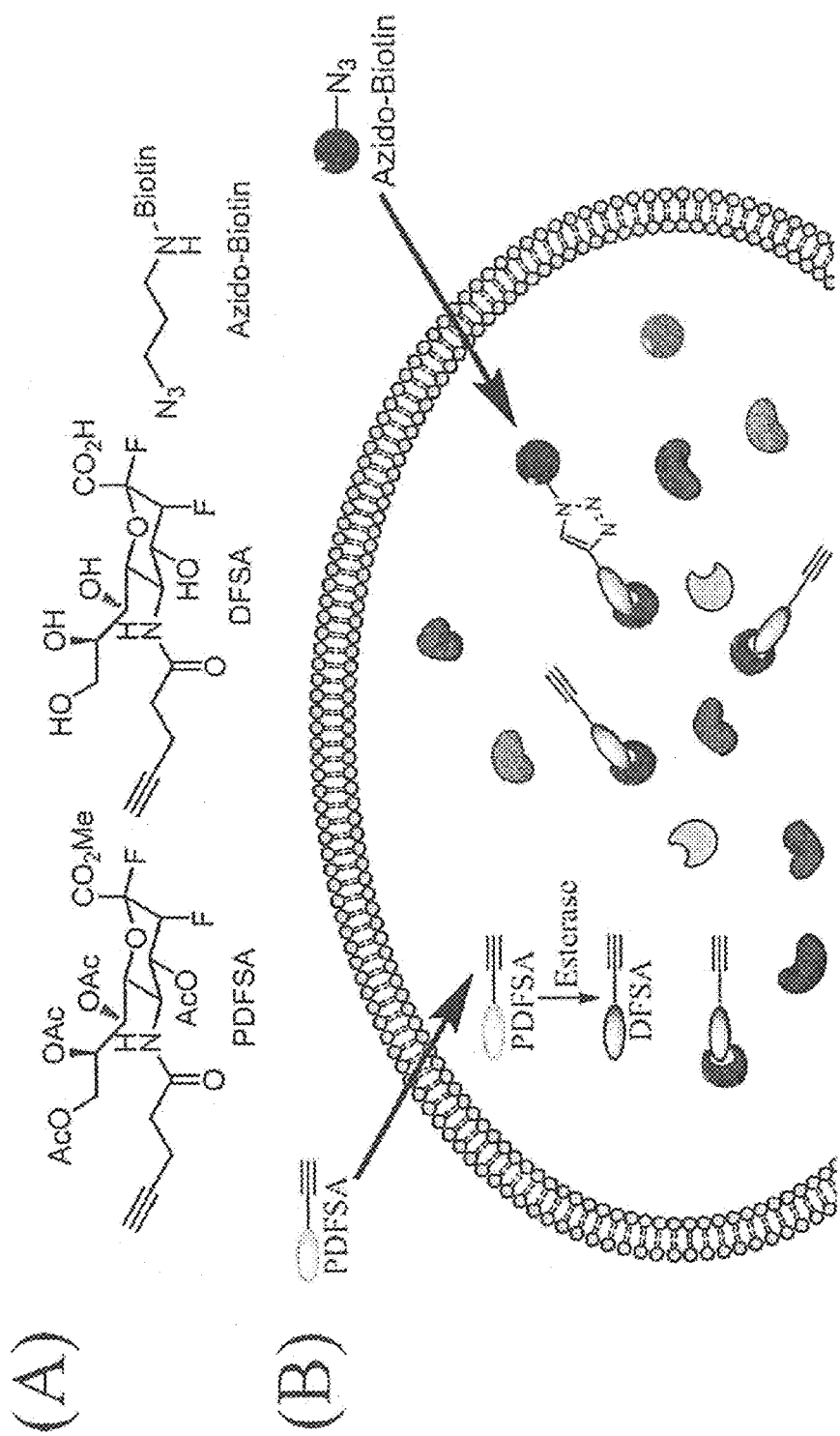
FIG. 1. Identification and imaging of sialidase activity changes using activity-based sialidase probes. (1A) Structures of DFSA, PDFSA, and Azido-Biotin. (1B) Identification and imaging of sialidase with activity changes using these activity-based sialidase probes.

This invention relates to irreversible inhibitors for sialidases. The provided irreversible inhibitors form a covalent bond with sialidases and trap the 3-fluorosialyl-enzyme intermediate. The fluorosialyl-enzyme adduct can be ligated with a detectable tagging moiety such as azide-annexed biotin (azido-biotin) via CuAAC for isolation and identification of the sialidase.

The invention further provides ester-protected sialidases inhibitors as the membrane permeable precursor to improve cell uptake. (A. K. Sarkar, et al. *Proc. Natl. Acad. Sci. USA* 1995, 92, 3323. C. L. Jacobs, et al. *Methods Enzymol.* 2000, 327, 260.) The cell-permeable sialidase inhibitors have allowed, for the first time, identification and in situ imaging of the changes of sialidase activity under physiological conditions.

In one aspect, the present disclosure provides novel irreversible sialidase inhibitors of formula (I):

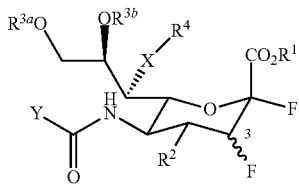

(I)

or a salt thereof,
wherein
F atom at the C3-position is axial or equatorial;
$R^1$ is H or optionally substituted $C_{1-6}$ alkyl;
$R^2$ is $OR^{2O}$, $N_3$, $N(R^{2N})_2$, or guanidine;
each instance of $R^{2O}$ is independently hydrogen, optionally substituted $C_{1-6}$ alkyl, optionally substituted acyl, or an oxygen protecting group;
each instance of $R^{2N}$ is independently hydrogen, optionally substituted $C_{1-6}$ alkyl, optionally substituted acyl, or a nitrogen protecting group;
each instance of $R^{3a}$ and $R^{3b}$ is independently hydrogen, —C(=O)—$R^{3r}$, or an oxygen protecting group;
each instance of $R^{3r}$ is optionally substituted $C_{1-6}$ alkyl, optionally substituted aryl, optionally substituted heteroaryl, or optionally substituted heterocycle, optionally substituted alkylaryl, optionally substituted alkylheteroaryl, or optionally substituted alkylheterocycle;
X is selected from the group consisting of —O—, —O(C=O)—, —NH—, —NH(C=O)—, —(C=O)NH—, —O(C=O)NH—, —O(C=S)NH—, —NH(C=O)NH—, and —NH(C=S)NH—;
$R^4$ is H, optionally substituted $C_{1-6}$ alkyl, or -L-Z;
Y is optionally substituted $C_{1-6}$ alkyl or -L-Z;
each instance of L is independently selected from the group consisting of —$(CH_2)_n$—, —$(CH_2)_n$C=O—, —$(CH_2)_n$NH—, —(C=O)$(CH_2)_n$—, —$(CH_2)_n$NH(C=O)—, —(C=O)$(CH_2)_n$NH(C=O)—, —$(CH_2)_n$SCH$_2$(C=O)—, and —$(CH_2CH_2O)_n$—;
each instance of n is an integer from 1 to 8, inclusive;
each instance of Z is a functional group for further ligation; and
provided that the compound is not of the formula

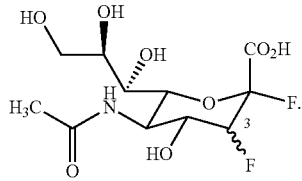 [SMILES: CC(=O)NC1C(O)C(F)C(F)(C(=O)O)OC1[C@H](O)[C@H](O)CO]

As generally defined herein, $R^1$ is H or optionally substituted $C_{1-6}$ alkyl. In certain embodiments, $R^1$ is H. In certain embodiments, $R^1$ is optionally substituted $C_{1-6}$ alkyl. In certain embodiments, $R^1$ is methyl, ethyl, or n-propyl.

As generally defined herein, $R^2$ is $OR^{2O}$, $N_3$, $N(R^{2N})_2$, or guanidine. In certain embodiments, $R^2$ is $OR^{2O}$, wherein $R^{2O}$ is independently hydrogen, optionally substituted $C_{1-6}$ alkyl, optionally substituted acyl, or an oxygen protecting group. In certain embodiments, $R^2$ is OH. In certain embodiments, $R^2$ is $OR^{2O}$, wherein $R^{2O}$ is optionally substituted $C_{1-6}$ alkyl. In certain embodiments, $R^2$ is $OCH_3$ or $OC_2H_5$. In certain embodiments, $R^2$ is OH. In certain embodiments, $R^2$ is $OR^{2O}$, wherein $R^{2O}$ is optionally substituted acyl. In certain embodiments, $R^2$ is $OR^{2O}$, wherein $R^{2O}$ is acetyl. In certain embodiments, $R^2$ is OH. In certain embodiments, $R^2$ is $OR^{2O}$, wherein $R^{2O}$ is an oxygen protecting group. In certain embodiments, $R^2$ is $N_3$. In certain embodiments, $R^2$ is $N(R^{2N})_2$, wherein each instance of $R^{2N}$ is independently hydrogen, optionally substituted $C_{1-6}$ alkyl, optionally substituted acyl, or a nitrogen protecting group. In certain embodiments, $R^2$ is $NH(R^{2N})$, wherein $R^{2N}$ is independently hydrogen, optionally substituted $C_{1-6}$ alkyl, optionally substituted acyl, or a nitrogen protecting group. In certain embodiments, $R^2$ is $NH_2$.

As generally defined herein, $R^{3a}$ is independently hydrogen, —C(=O)—$R^{3r}$, or an oxygen protecting group. In certain embodiments, $R^{3a}$ is hydrogen. In certain embodiments, $R^{3a}$ is —C(=O)—$R^{3r}$, wherein $R^{3r}$ is optionally substituted $C_{1-6}$ alkyl, optionally substituted aryl, optionally substituted heteroaryl, optionally substituted heterocycle, optionally substituted alkylaryl, optionally substituted alkylheteroaryl, or optionally substituted alkylheterocycle. In certain embodiments, $R^{3a}$ is —C(=O)—$R^{3r}$, wherein $R^{3r}$ is optionally substituted $C_{1-6}$ alkyl. In certain embodiments, $R^{3a}$ is —C(=O)—$R^{3r}$, wherein $R^{3r}$ is methyl or ethyl. In certain embodiments, $R^{3a}$ is —C(=O)—$R^{3r}$, wherein $R^{3r}$ is optionally substituted aryl. In certain embodiments, $R^{3a}$ is —C(=O)—$R^{3r}$, wherein $R^{3r}$ is phenyl. In certain embodiments, $R^{3a}$ is —C(=O)—$R^{3r}$, wherein $R^{3r}$ is optionally substituted alkylaryl. In certain embodiments, $R^{3a}$ is —C(=O)—$R^{3r}$, wherein $R^{3r}$ is optionally substituted benzoyl. In certain embodiments, $R^{3a}$ is $CH_3CO$—, $C_2H_5CO$—, $C_3H_7CO$—, t-BuCO—, $CF_3CO$—, $PhCH_2CO$—, or $C_6H_5CO$—.

As generally defined herein, $R^{3b}$ is independently hydrogen, —C(=O)—$R^{3r}$, or an oxygen protecting group. In certain embodiments, $R^{3b}$ is hydrogen. In certain embodiments, $R^{3b}$ is —C(=O)—$R^{3r}$, wherein $R^{3r}$ is optionally substituted $C_{1-6}$ alkyl, optionally substituted aryl, optionally substituted heteroaryl, optionally substituted heterocycle, optionally substituted alkylaryl, optionally substituted alkylheteroaryl, or optionally substituted alkylheterocycle. In certain embodiments, $R^{3b}$ is —C(=O)—$R^{3r}$, wherein $R^{3r}$ is optionally substituted $C_{1-6}$ alkyl. In certain embodiments, $R^{3b}$ is —C(=O)—$R^{3r}$, wherein $R^{3r}$ is methyl or ethyl. In certain embodiments, $R^{3b}$ is —C(=O)—$R^{3r}$, wherein $R^{3r}$ is optionally substituted aryl. In certain embodiments, $R^{3b}$ is —C(=O)—$R^{3r}$, wherein $R^{3r}$ is phenyl. In certain embodiments, $R^{3b}$ is —C(=O)—$R^{3r}$, wherein $R^{3r}$ is optionally substituted alkylaryl. In certain embodiments, $R^{3b}$ is —C(=O)—$R^{3r}$, wherein $R^{3r}$ is optionally substituted benzoyl. In certain embodiments, $R^{3b}$ is $CH_3CO$—, $C_2H_5CO$—, $C_3H_7CO$—, t-BuCO—, $CF_3CO$—, $PhCH_2CO$—, or $C_6H_5CO$—.

As generally defined herein, linker X is selected from the group consisting of —O—, —O(C=O)—, —NH—, —(C=O)NH—, —NH(C=O)—, —O(C=O)NH—, —O(C=S)NH—, —NH(C=O)NH—, and —NH(C=S)NH—. In certain embodiments, X is —O—. In certain embodiments, X is —O(C=O)—. In certain embodiments, X is —NH(C=O)—. In certain embodiments, X is —(C=O)NH—. In certain embodiments, X is —O(C=O)NH—.

As generally defined herein, $R^4$ is H, optionally substituted $C_{1-6}$ alkyl, or -L-Z. In certain embodiments, $R^4$ is H. In certain embodiments, $R^4$ is -L-Z, wherein L is independently selected from the group consisting of —$(CH_2)_n$—, —$(CH_2)_n$C=O—, —$(CH_2)_n$NH—, —(C=O)$(CH_2)_n$—, —$(CH_2)_n$NH(C=O)—, —(C=O)$(CH_2)_n$NH(C=O)—, —$(CH_2)_n$SCH$_2$(C=O)—, and —$(CH_2CH_2O)_n$—; each instance of n is an integer from 1 to 8, inclusive; and Z is a functional group for further ligation. In certain embodiments, $R^4$ is —$(CH_2)_n$—Z, wherein n is an integer from 1 to 8, inclusive; and Z is a functional group for further ligation. In certain embodiments, $R^4$ is —$(CH_2)_n$—Z, wherein n is an integer from 1 to 8, inclusive; and Z is is optionally substituted alkyne, optionally substituted alkene, halogen, —$N_3$, $N(R^N)_2$, $OR^O$, $SR^S$, or $CO_2R^O$; wherein each instance of $R^N$ is independently hydrogen, optionally substituted $C_{1-6}$ alkyl, or a nitrogen protecting group; each instance of $R^O$ is independently hydrogen, optionally substituted $C_{1-6}$ alkyl, optionally substituted acyl, or an oxygen protecting group; and each instance of $R^S$ is independently hydrogen, optionally substituted $C_{1-6}$ alkyl, or a sulfur protecting group.

As generally defined herein, Y is optionally substituted $C_{1-6}$ alkyl or -L-Z. In certain embodiments, Y is optionally substituted $C_{1-6}$ alkyl. In certain embodiments, Y is substituted $C_{1-6}$ alkyl. In certain embodiments, Y is $CF_3$. In certain embodiments, Y is unsubstituted $C_{1-6}$ alkyl. In certain embodiments, Y is methyl, ethyl, or n-propyl. In certain embodiments, Y is -L-Z, wherein L is independently selected from the group consisting of —$(CH_2)_n$—, —$(CH_2)_nC$=O—, —$(CH_2)_nNH$—, —$(C$=$O)(CH_2)_n$—, —$(CH_2)_nNH(C$=$O)$—, —$(C$=$O)(CH_2)_nNH(C$=$O)$—, —$(CH_2)_nSCH_2(C$=$O)$—, and —$(CH_2CH_2O)_n$—; each instance of n is an integer from 1 to 8, inclusive; and Z is a functional group for further ligation. In certain embodiments, Y is —$(CH_2)_n$—Z, wherein n is an integer from 1 to 8, inclusive; and Z is a functional group for further ligation. In certain embodiments, Y is —$(CH_2)_n$—Z, wherein n is an integer from 1 to 8, inclusive; and Z is is optionally substituted alkyne, optionally substituted alkene, halogen, —$N_3$, $N(R^N)_2$, $OR^O$, $SR^S$, or $CO_2R^O$; wherein each instance of $R^N$ is independently hydrogen, optionally substituted $C_{1-6}$ alkyl, or a nitrogen protecting group; each instance of $R^O$ is independently hydrogen, optionally substituted $C_{1-6}$ alkyl, optionally substituted acyl, or an oxygen protecting group; and each instance of $R^S$ is independently hydrogen, optionally substituted $C_{1-6}$ alkyl, or a sulfur protecting group.

In one embodiments for the compound of formula (I), Z is optionally substituted alkyne, optionally substituted alkene, halogen, —$N_3$, $N(R^N)_2$, $OR^O$, $SR^S$, or $CO_2R^O$; wherein each instance of $R^N$ is independently hydrogen, optionally substituted $C_{1-6}$ alkyl, or a nitrogen protecting group; each instance of $R^O$ is independently hydrogen, optionally substituted $C_{1-6}$ alkyl, optionally substituted acyl, or an oxygen protecting group; and each instance of $R^S$ is independently hydrogen, optionally substituted $C_{1-6}$ alkyl, or a sulfur protecting group.

In some embodiments, the compound of formula (I) of formula (II-a):

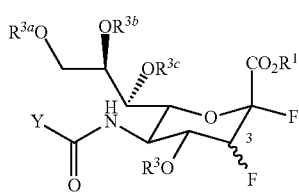

(II-a)

or a salt thereof,
wherein $R^{3c}$ is independently hydrogen, optionally substituted $C_{1-6}$ alkyl, optionally substituted acyl, or an oxygen protecting group.

In certain embodiments, $R^{3c}$ is hydrogen. In certain embodiments, $R^{3c}$ is optionally substituted $C_{1-6}$ alkyl. In certain embodiments, $R^{3c}$ is methyl or ethyl. In certain embodiments, $R^{3c}$ is optionally substituted acyl. In certain embodiments, $R^{3c}$ is acetyl. In certain embodiments, $R^{3c}$ is an oxygen protecting group.

In some embodiments, the compound of formula (I) of formula (II-b):

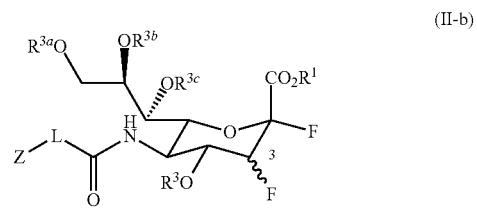

(II-b)

or a salt thereof.

In some embodiments, the compound of formula (I) of formula (II-b1):

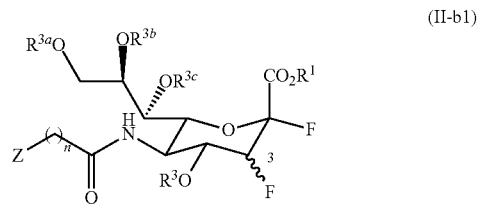

(II-b1)

or a salt thereof.

In some embodiments, the compound of formula (I) of formula (II-b2):

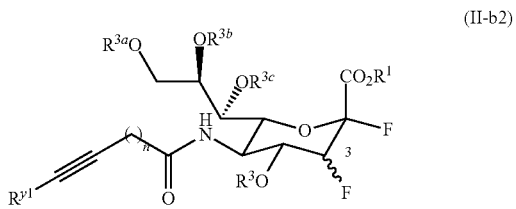

(II-b2)

or a salt thereof,
wherein $R^{y1}$ is hydrogen, halogen, or optionally substituted $C_{1-6}$ alkyl.

As defined herein, $R^{y1}$ is hydrogen, halogen, or optionally substituted $C_{1-6}$ alkyl. In certain embodiments, $R^{y1}$ is hydrogen. In certain embodiments, $R^{y1}$ is halogen. In certain embodiments, $R^{y1}$ is optionally substituted $C_{1-6}$ alkyl. In certain embodiments, $R^{y1}$ is methyl or ethyl.

In some embodiments, the compound of formula (I) of formula (II-b3):

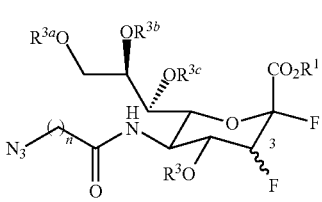 (II-b3)

or a salt thereof.

In some embodiments, the compound of formula (I) of formula (II-c):

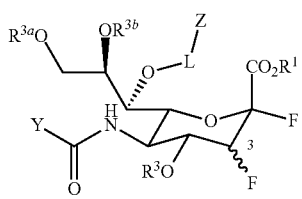 (II-c)

or a salt thereof.

In some embodiments, the compound of formula (I) of formula (II-c1):

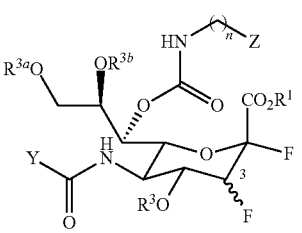 (II-c1)

or a salt thereof.

In some embodiments, the compound of formula (I) of formula (II-c2):

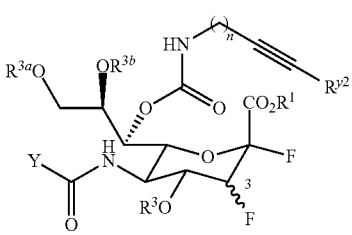 (II-c2)

or a salt thereof, wherein $R^{y2}$ is hydrogen, halogen, or optionally substituted $C_{1-6}$ alkyl.

As defined herein, $R^{y2}$ is hydrogen, halogen, or optionally substituted $C_{1-6}$ alkyl. In certain embodiments, $R^{y2}$ is hydrogen. In certain embodiments, $R^{y2}$ is optionally substituted $C_{1-6}$ alkyl. In certain embodiments, $R^{y2}$ is methyl or ethyl.

In some embodiments, the compound of formula (I) of formula (II-c3):

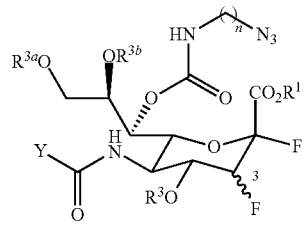 (II-c3)

or a salt thereof.

In some embodiments, the provided compounds have the F atom at the C3 axial position. In some embodiments, the provided compounds have the F atom at the C3 equatorial position.

In another aspect, the invention provides a sialidase protein adduct comprising a compound provided herein. In certain embodiments, the sialidase protein is covalently conjugated to the compound. In certain embodiments, the protein adduct is of the formula

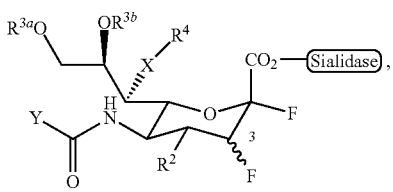

wherein Y, X, $R^2$, $R^{3a}$, $R^{3b}$, $R^4$ are as defined herein. In certain embodiments, the compound is DFSA-5-yne or DFSA-7-yne. In certain embodiments, the compound is covalently linked to one or more tyrosine (Y) residues within any peptide of SEQ ID NOS: 1-6, wherein the peptide is a fragment of nanA, nanB, nanC, nanJ, nanI or nanH.

In another aspect, the invention provides a detectable conjugate comprising a compound as described herein, wherein the compound is covalently conjugated to a detectable tagging moiety.

In another aspect, the invention provides a detectable sialidase conjugate comprising a sialidase protein adduct as described herein, wherein the sialidase protein adduct is covalently conjugated to a detectable tagging moiety.

The detectable tagging moiety is a functional group that enables detection of the entity to which it is conjugated to. The provided detectable conjugates have a detectable tagging moiety covalently conjugated to the compound or sialidase conjugate as described herein. The provided detectable conjugates can be ascertained for their existence and presence by detection of the signals generated from the detectable tagging moiety. The detection of the signals can be conducted by any of the chemical or physical means such as imaging or recordation of signals. In certain embodiments, the signals are detected by the streptavidin-specific reporting signals.

Exemplary detectable tagging moieties include, but are not necessarily limited to, fluorescent molecules (e.g., auto-fluorescent molecules, molecules that fluoresce upon contact with a reagent, etc.), radioactive labels (e.g., $^{111}$In, $^{125}$I, $^{131}$I, $^{212}$B, $^{90}$Y, $^{186}$Rh, and the like); biotin (e.g., to be detected through reaction of biotin and avidin); fluorescent tags; imaging reagents (e.g., those described in U.S. Pat. No. 4,741,900 and U.S. Pat. No. 5,326,856), and the like.

Detectable labels also include peptides or polypeptides that can be detected by antibody binding, e.g., by binding of a detectably labeled antibody or by detection of bound antibody through a sandwich-type assay. Also suitable for use are quantum dots (e.g., detectably labeled semiconductor nanocrystals, such as fluorescently labeled quantum dots, antibody-conjugated quantum dots, and the like). See, e.g., Dubertret et al. 2002 *Science* 298:759-1762; Chan et al. (1998) Science 281:2016-2018; U.S. Pat. No. 6,855,551; Bruchez et al. (1998) Science 281:2013-2016.

Suitable fluorescent molecules (fluorophores) include, but are not limited to, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoylcarbocyanine iodide), tetrabromorhodamine 123, rhodamine 6G, TMRM (tetramethylrhodamine-, methyl ester), TMRE (tetramethylrhodamine, ethyl ester), tetramethylrosamine, rhodamine B and 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphth-alimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120), 7-amino-4-trifluoromethylcoumarin (Coumarin 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM),5-(4,6-dichlorotriazin-2-yl)aminofluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl hodamine isothiocyanate (TRITC); riboflavin; 5-(2'-aminoethyl) aminonaphthalene-1-sulfonic acid (EDANS), 4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, and fluorescent europium and terbium complexes; and the like. Fluorophores of interest are farther described in WO 01/42505 and WO 01/86001.

Suitable fluorescent proteins and chromogenic proteins include, but are not limited to, a green fluorescent protein (GFP), including, but not limited to, a GFP derived from *Aequoria victoria* or a derivative thereof, e.g., a "humanized" derivative such as Enhanced GFP, which is available commercially, e.g., from Clontech, Inc.; a GFP from another species such as *Renilla reniformis, Renilla mulleri,* or *Ptilosarcus guernyi,* as described in, e.g., WO 99/49019 and Peelle et al. (2001) *J. Protein Chem.* 20:507-519; "humanized" recombinant GFP (hrGFP) (Stratagene); any of a variety of fluorescent and colored proteins from Anthozoan species, as described in, e.g., Matz et al. (1999) *Nature Biotechnol.* 17:969-973; and the like.

Suitable epitope tags include, but are not limited to, hemagglutinin; FLAG; FLAG-C; a metal ion affinity tag such as a polyhistidine tag (e.g., $His_6$), and the like.

Suitable imaging agents include positive contrast agents and negative contrast agents. Suitable positive contrast agents include, but are not limited to, gadolinium tetraazacyclododecanetetraacetic acid (Gd-DOTA); Gadolinium-diethylenetriaminepentaacetic acid (Gd-DTPA); Gadolinium-1,4,7-tris(carbonylmethyl)-10-(2'-hydroxypropyl)-1,4,7,10-tetraazacyclododecane (Gd—HP-DO3A); Manganese(II)-dipyridoxal diphosphate (Mn-DPDP); Gd-diethylenetriaminepentaacetate-bis(methylamide) (Gd-DTPA-BMA); and the like. Suitable negative contrast agents include, but are not limited to, a superparamagnetic iron oxide (SPIO) imaging agent; and a perfluorocarbon, where suitable perfluorocarbons include, but are not limited to, fluoroheptanes, fluorocycloheptanes, fluoromethylcycloheptanes, fluorohexanes, fluorocyclohexanes, fluoropentanes, fluorocyclopentanes, fluoromethylcyclopentanes, fluorodimethylcyclopentanes, fluoromethylcyclobutanes, fluorodimethylcyclobutanes, fluorotrimethylcyclobutanes, fluorobutanes, fluorocyclobutanse, fluoropropanes, fluoroethers, fluoropolyethers, fluorotriethylamines, perfluorohexanes, perfluoropentanes, perfluorobutanes, perfluoropropanes, sulfur hexafluoride, and the like.

In certain embodiments, the detectable tagging moiety comprises a label. In certain embodiments, the label is a fluorophore. In certain embodiments, the label is of the formula

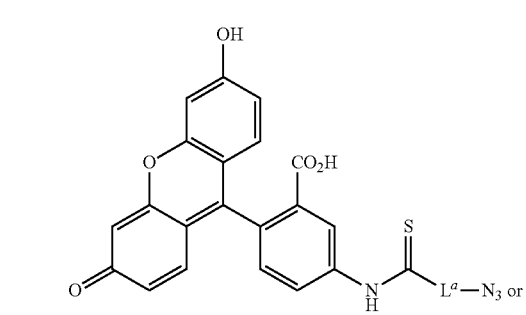

-continued

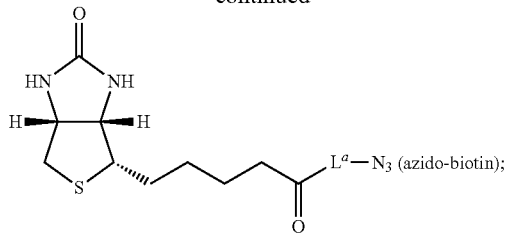

wherein $L^a$ is optionally substituted alkylene; optionally substituted alkenylene; optionally substituted alkynylene; optionally substituted heteroalkylene; optionally substituted heteroalkenylene; optionally substituted heteroalkynylene; optionally substituted arylene; optionally substituted heteroarylene; or optionally substituted acylene.

In certain embodiments, the label is of the formula

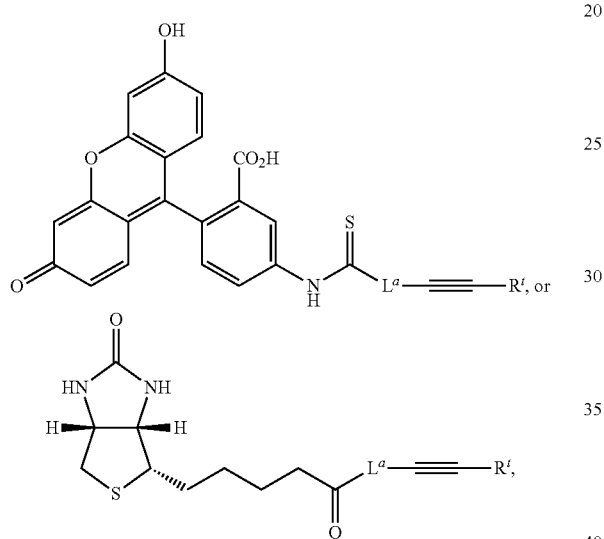

wherein $L^a$ is defined herein; and each instance of $R^t$ is hydrogen, halogen, optionally substituted $C^{1-6}$ alkyl, optionally substituted $C_{1-6}$ alkyl, optionally substituted aryl, optionally substituted heteroaryl, or optionally substituted heterocycle.

As generally defined herein, $L^a$ is optionally substituted alkylene; optionally substituted alkenylene; optionally substituted alkynylene; optionally substituted heteroalkylene; optionally substituted heteroalkenylene; optionally substituted heteroalkynylene; optionally substituted arylene; optionally substituted heteroarylene; or optionally substituted acylene. In certain embodiments, $L^a$ is an optionally substituted alkylene. In certain embodiments, $L^a$ is an unsubstituted alkylene. In certain embodiments, $L^a$ is $-CH_2-$. In certain embodiments, $L^a$ is $-(CH_2)_2-$. In certain embodiments, $L^a$ is $-(CH_2)_3-$. In certain embodiments, $L^a$ is $-(CH_2)_4-$. In certain embodiments, $L^a$ is $-(CH_2)_5-$.

As generally defined herein, $R^t$ is hydrogen, halogen, optionally substituted $C_{1-6}$ alkyl, optionally substituted $C_{1-6}$ alkyl, optionally substituted aryl, optionally substituted heteroaryl, or optionally substituted heterocycle. In certain embodiments, $R^t$ is hydrogen. In certain embodiments, $R^s$ is halogen. In certain embodiments, $R^t$ is optionally substituted $C_{1-6}$ alkyl. In certain embodiments, $R^t$ is methyl or ethyl.

In certain embodiments, the provided detectable conjugates are of formula (X-a), (X-b), (XI-a) or (XI-b):

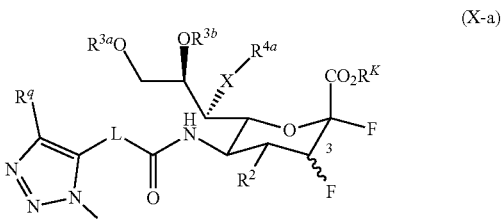

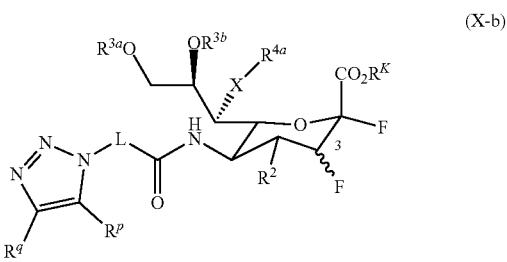

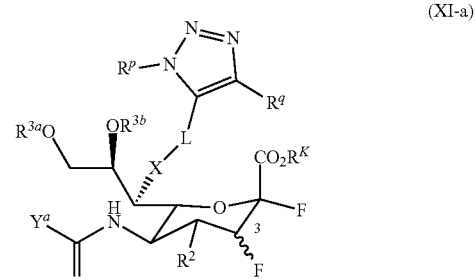

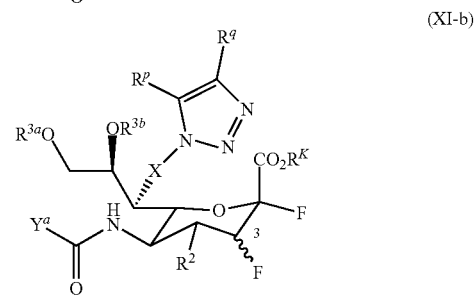

or a salt thereof,
wherein
F atom at the C3-position is axial or equatorial;
$R^K$ is H, optionally substituted $C_{1-6}$ alkyl, or a sialidase protein;
$R^2$, $R^{3a}$, $R^{3b}$, and X are as defined herein;
$R^{4a}$ is H, optionally substituted $C_{1-6}$ alkyl, or an optionally substituted acyl;
$Y^a$ is H or optionally substituted $C_{1-6}$ alkyl;
each instance of $R^p$ and $R^q$ is independently hydrogen, optionally substituted aliphatic; optionally substituted heteroaliphatic; substituted or unsubstituted aryl; optionally substituted heteroaryl; optionally substituted acyl; a resin; a protein; a reporter; a label optionally joined by a linker $L^a$, wherein the linker $L^a$ is optionally substituted alkylene; optionally substituted alkenylene; optionally substituted alkynylene; optionally substituted heteroalkylene; optionally substituted heteroalkenylene; optionally substituted heteroalkynylene; optionally substituted arylene; optionally substituted heteroarylene; or optionally substituted acylene.

As generally defined herein, $R^K$ is H, optionally substituted $C_{1-6}$ alkyl, or a sialidase protein. In certain embodiments, $R^K$ is H. In certain embodiments, $R^K$ is optionally substituted $C_{1-6}$ alkyl. In certain embodiments, $R^K$ is methyl or ethyl. In certain embodiments, $R^K$ is a sialidase protein.

As generally defined herein, $R^{4a}$ is H, optionally substituted $C_{1-6}$ alkyl, or an optionally substituted acyl. In certain embodiments, $R^{4a}$ is H. In certain embodiments, $R^{4a}$ is optionally substituted $C_{1-6}$ alkyl. In certain embodiments, $R^{4a}$ is methyl, ethyl, or n-propyl. In certain embodiments, $R^{4a}$ is an optionally substituted acyl. In certain embodiments, $R^{4a}$ is an optionally substituted acetyl.

In certain embodiments of formula (X-a), (X-b), (XI-a) or (XI-b), X is O and $R^{4a}$ is H, optionally substituted $C_{1-6}$ alkyl, or an optionally substituted acyl acyl. In certain embodiments of formula (X-a), (X-b), (XI-a) or (XI-b), X is O and $R^{4a}$ is H. In certain embodiments of formula (X-a), (X-b), (XI-a) or (XI-b), X is O and $R^{4a}$ is optionally substituted $C_{1-6}$ alkyl. In certain embodiments of formula (X-a), (X-b), (XI-a) or (XI-b), X is O and $R^{4a}$ is methyl or ethyl. In certain embodiments of formula (X-a), (X-b), (XI-a) or (XI-b), X is O and $R^{4a}$ is optionally substituted acyl. In certain embodiments of formula (X-a), (X-b), (XI-a) or (XI-b), X is O and $R^{4a}$ is acetyl.

As generally defined herein, $Y^a$ is H or optionally substituted $C_{1-6}$ alkyl. In certain embodiments, $Y^a$ is H. In certain embodiments, $Y^a$ is optionally substituted $C_{1-6}$ alkyl. In certain embodiments, $Y^a$ is methyl, ethyl, or n-propyl.

As generally defined herein, $R^p$ is independently hydrogen, optionally substituted aliphatic; optionally substituted heteroaliphatic; substituted or unsubstituted aryl; optionally substituted heteroaryl; optionally substituted acyl; a resin; a protein; a reporter; a label optionally joined by a linker $L^a$, wherein the linker $L^a$ is optionally substituted alkylene; optionally substituted alkenylene; optionally substituted alkynylene; optionally substituted heteroalkylene; optionally substituted heteroalkenylene; optionally substituted heteroalkynylene; optionally substituted arylene; optionally substituted heteroarylene; or optionally substituted acylene. In certain embodiments, $R^p$ is hydrogen. In certain embodiments, $R^p$ is a reporter. In certain embodiments, $R^p$ is a reporter joined by linker $L^a$, wherein $L^a$ is defined herein. In certain embodiments, $R^p$ is a label. In certain embodiments, $R^p$ is a label joined by linker $L^a$, wherein $L^a$ is defined herein.

As generally defined herein, $R^q$ is independently hydrogen, optionally substituted aliphatic; optionally substituted heteroaliphatic; substituted or unsubstituted aryl; optionally substituted heteroaryl; optionally substituted acyl; a resin; a protein; a reporter; a label optionally joined by a linker $L^a$, wherein the linker $L^a$ is optionally substituted alkylene; optionally substituted alkenylene; optionally substituted alkynylene; optionally substituted heteroalkylene; optionally substituted heteroalkenylene; optionally substituted heteroalkynylene; optionally substituted arylene; optionally substituted heteroarylene; or optionally substituted acylene. In certain embodiments, $R^q$ is hydrogen. In certain embodiments, $R^q$ is a reporter. In certain embodiments, $R^q$ is a reporter joined by linker $L^a$, wherein $L^a$ is defined herein. In certain embodiments, $R^q$ is a label. In certain embodiments, $R^q$ is a label joined by linker $L^a$, wherein $L^a$ is defined herein.

In certain embodiments, $R^p$ is hydrogen and $R^q$ is a reporter or a label optionally joined by a linker $L^a$. In certain embodiments, $R^q$ is hydrogen and $R^p$ is a reporter or a label optionally joined by a linker $L^a$.

In certain embodiments, the provided detectable conjugates are of one of the formulae:

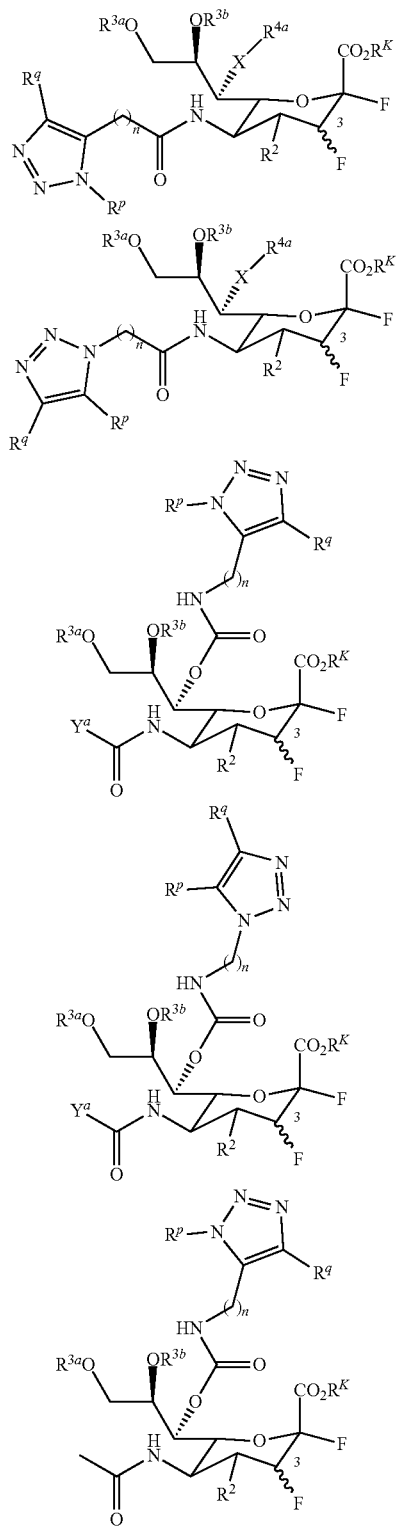

-continued

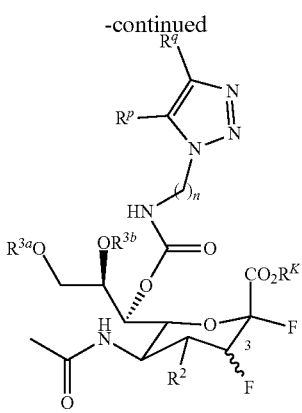

In another aspect, the invention provides a method for detecting presence of a sialidase, the method comprising:
(a) contacting a sample suspected of comprising a sialidase with a compound as described herein;
(c) adding a reporter; and
(c) detecting a signal,
wherein presence of a signal indicates the presence of the sialidase in the sample.

In another aspect, the invention provides a method for detecting presence of a sialidase, the method comprising:
(a) contacting a sample suspected of comprising a sialidase with a detectable conjugate;
(c) adding a reporter; and
(c) detecting a signal,
wherein presence of a signal indicates the presence of the sialidase in the sample.

In certain embodiments, the sialidase is intracellular. In certain embodiments, the detectable conjugate comprises PDFSA-5-yne (IV) or PDFSA-7-yne (VII):

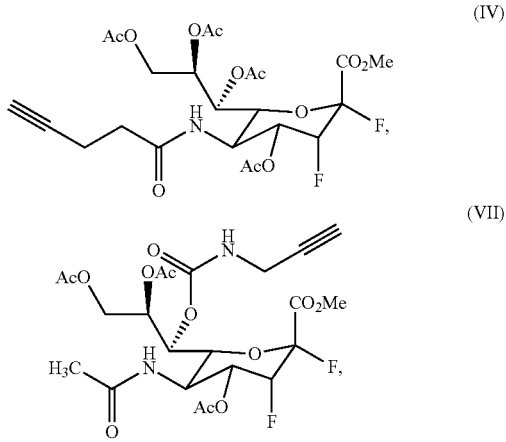

a derivative, conjugate or ester thereof. In certain embodiments, the sample is from a mammal, fowl, or fish. In certain embodiments, the sample is from a human. In certain embodiments, the sample is suspected of containing a pathogen. In certain embodiments, the sample contains a bacterium, virus, protozo, or a fungus.

As generally used herein, the sialidase is a human, viral or bacterial sialidase. In certain embodiments, the sialidase is a human sialidase. In certain embodiments, the sialidase is an influenza virus neuraminidase (NA). In certain embodiments, the sialidase is a human sialidase selected from the group consisting of Neu1, Neu2, Neu3 and Neu4. In certain embodiments, the sialidase is a bacterial sialidase selected from the group consisting of nanA, nanB, nanC, nanJ, nanI, and nanH.

In certain embodiments, the method further comprises imaging the intracellular locations of sialidases in a cell.

As generally used herein, the reporter refers to a chemical entity capable of forming a detectable tagging moiety with a target molecule, adduct, or conjugate. In some embodiments, the target molecule can be any compound as described herein or any a sialidase-compound conjugate. In certain embodiments, the reporter reacts with the compound or sialidase-compound conjugate via click reaction to introduce a detectable tagging moiety to the compound or sialidase-compound conjugate.

Click chemistry is a chemical approach introduced by Sharpless in 2001 and describes chemistry tailored to generate substances quickly and reliably by joining small units together. See, e.g., Kolb, Finn and Sharpless Angewandte Chemie International Edition (2001) 40: 2004-2021; Evans, Australian Journal of Chemistry (2007) 60: 384-395). Exemplary coupling reactions (some of which may be classified as "Click chemistry") include, but are not limited to, formation of esters, thioesters, amides (e.g., such as peptide coupling) from activated acids or acyl halides; nucleophilic displacement reactions (e.g., such as nucleophilic displacement of a halide or ring opening of strained ring systems); azide-alkyne Huisgon cycloaddition; thiol-yne addition; imine formation; and Michael additions (e.g., maleimide addition). In certain embodiments, the click reaction is carried out in the presence of copper (Kolb, et al., Angew Chem. Int. Ed., 2001, 40, 2004; Rostovtsev et al., Angew Chem. Int. Ed., 2002, 41, 2596; Wu et al, Aldrichimica Acta, 2007, 40, 7).

In certain embodiments, the reporter comprises an azido group. In certain embodiments, the reporter comprises a terminal alkyne. In certain embodiments, the reporter is an azido-biotin.

In certain embodiments, the method further comprises:
(d) contacting a cell with a compound of PDFSA-5-yne (IV), PDFSA-7-yne (VII), or a derivative, or ester thereof;
(e) allowing intracellular esterase to convert the compound to DFSA-5-yne (III) or DFSA-7-yne (VI) respectively;
(f) allowing DFSA-5-yne (III) or DFSA-7-yne (VI) to covalently conjugate to one or more sialidases at an intracellular location in the cell;
(g) adding a reporter;
(h) obtaining an image of intracellular sialidase distribution.

In another aspect, the invention provides a method for diagnosis of sialidosis, the method comprising:
(a) contacting a test sample from a subject suspected of sialidosis with a compound as described herein;
(b) adding a reporter;
(c) detecting a signal, and
(d) comparing the signal with that from a healthy subject, wherein a relative reduction of signal in the test sample indicates sialidosis.

In another aspect, the invention provides a method for diagnosis of sialidosis, the method comprising:
(a) contacting a test sample from a subject suspected of sialidosis with a detectable conjugate as described herein;
(b) detecting a signal, and
(d) comparing the signal with that from a healthy subject, wherein a relative reduction of signal in the test sample indicates sialidosis.

In some embodiments of the diagnosis method, the test sample contains fibroblast. In some embodiments of the diagnosis method, the detectable conjugate comprises PDFSA-5-yne (IV), PDFSA-7-yne (VII), or a derivative, conjugate or ester thereof.

In another aspect, the invention provides a method for diagnosing infection by influenza virus, the method comprising:

(a) contacting a test sample from a subject suspected of influenza virus infection with the compound of any one of claims 1-23;

(b) adding a reporter;

(c) detecting a signal;

wherein the presence of a signal indicates a possibility of infection by influenza virus.

In another aspect, the invention provides a method for diagnosing infection by influenza virus, the method comprising:

(a) contacting a test sample from a subject suspected of influenza virus infection with the detectable conjugate of claim 32;

(b) detecting a signal;

wherein the presence of a signal indicates a possibility of infection by influenza virus.

In certain embodiments of the diagnostic methods, the influenza virus is extracellular. In certain embodiments of the diagnostic methods, the influenza virus is intracellular. In certain embodiments of the diagnostic methods, the detectable conjugate comprises DFSA-5-yne (II) or DFSA-7-yne (VI) or a derivative, conjugate or ester thereof. In certain embodiments of the diagnostic method, the the influenza virus is not resistant to oseltamivir (OS). In certain embodiments of the diagnostic method, the the influenza virus is sensitive to oseltamivir (OS). In certain embodiments of the diagnostic methods, the the influenza virus is resistant to oseltamivir (OS). In certain embodiments, the oseltamivir-resistant influenza virus is H1N1, H1N9, H3N1, H3N2, H5N1, H7N9. In certain embodiments, the oseltamivir-resistant influenza virus is H1N1. In certain embodiments of the diagnostic method, the influenza virus is present at a titer of $10^4$ or higher.

In another aspect, the invention provides a method for imaging sialidase in a live cell, comprising:

incubating a live cell containing sialidase with any compound as described herein under conditions allowing conjugation of the compound to the sialidase, contacting the sialidase-compound conjugate with a reporter under conditions allowing conjugation of the reporter to the compound, and detecting a signal released from the reporter that is conjugated to the compound.

In certain embodiments of any of the provided methods, the detectable signal is generated by the label of the detectable conjugate. In certain embodiments of the provided methods, the detectable signal is released from the reporter conjugated with the compound. In certain embodiments, the detectable signal is released from the reporter conjugated with the compound-sialidase adduct. In certain embodiments, the reporter comprises a label. In certain embodiments, the reporter comprises an azido moity and a label. In certain embodiments, the reporter comprises an alkyne moiety and a label. In certain embodiments, the reporter comprises a biotin moiety and an alkyne moiety. In certain embodiments, the reporter comprises a biotin moiety and an azido moiety. In certain embodiments, the reporter is of the formula

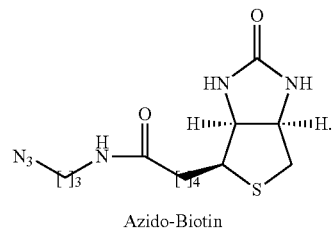

Azido-Biotin

In another aspect, the exemplary syntheses of the provided compounds such as DFSA-5-yne and PDFSA-5-yne comprise the steps of:

(a) reaction of N-(pent-4-ynoyl)-mannosamine (1) (T. L. Hsu, et al. *Proc. Natl. Acad. Sci. USA* 2007, 104, 2614.) with 3-fluoropyruvic acid (as the sodium salt) by catalysis of N-acetylneuraminic acid aldolase (Neu5Ac aldolase, EC 4.1.3.3) to yield an adduct 2;

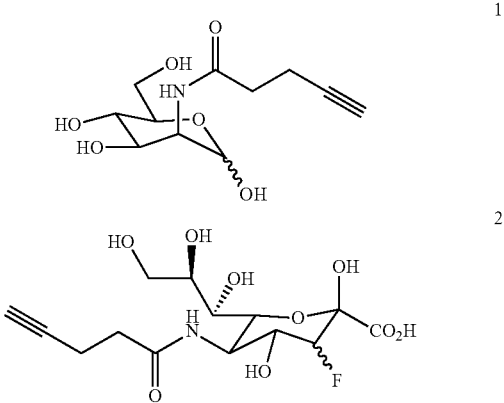

(b) esterification of adduct 2 in methanol in the presence of IR-120 resin (acid form) to give compound 3;

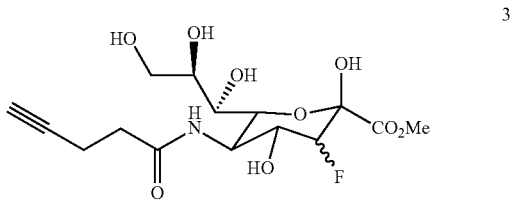 [SMILES: C#CCCC(=O)NC1C(O)C(F)C(O)(C(=O)OC)OC1[C@H](O)[C@H](O)CO]

(c) acetylation of compound 3, followed by chromatographic isolation, to give peracetylated ester 4;

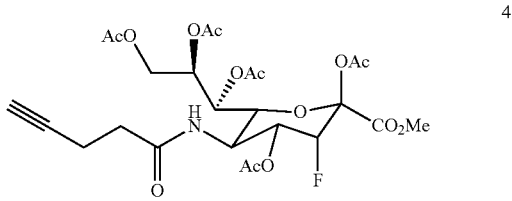 [SMILES: C#CCCC(=O)NC1C(OC(C)=O)C(F)C(O)(C(=O)OC)OC1[C@H](OC(C)=O)[C@@H](COC(C)=O)OC(C)=O]

(d) selective deacetylation at the anomeric position of compound 4 by using hydrazine acetate to give compound 5;

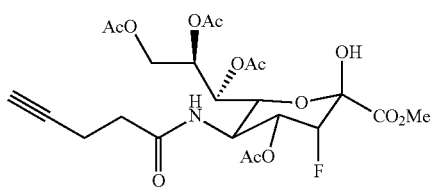

5

(e) treatment of compound 5 with diethylaminosulfurtrifluoride (DAST) to give PDFSA-5-yne (α-anomer, 60%) and its β-anomer (30%);

and (f) deprotection of PDFSA-5-yne under alkaline conditions, followed by purification on a reversed-phase column, to give DFSA-5-yne.

In another aspect, the exemplary synthesis of the provided compounds such as DFSA-7-yne and PDFSA-7-yne further comprise steps:

(g) reaction of D-mannosamine with 3-fluoropyruvic acid (as the sodium salt) by catalysis of N-acetylneuraminic acid aldolase (Neu5Ac aldolase, EC 4.1.3.3) to yield an adduct 6;

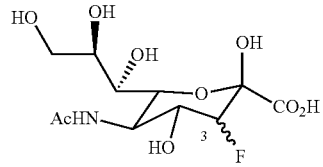

6

(h) esterification of adduct 6 in methanol in the presence of IR-120 resin (acid form) to give compound 7;

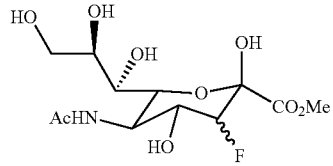

7

(i) acetylation of compound 7, followed by chromatographic isolation, to give peracetylated ester 8;

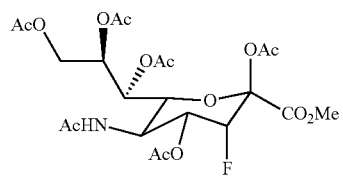

8

(j) selective deacetylation at the anomeric position of compound 8 by using hydrazine acetate to give compound 9;

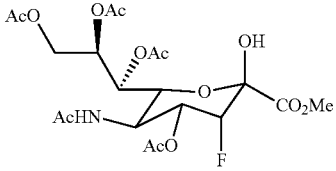

9

(k) treatment of compound 9 with diethylaminosulfurtrifluoride (DAST) to give compound 10;

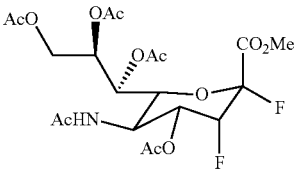

10

(l) treatment of compound 10 with methanesulfonic acid in methanol to give compound 11;

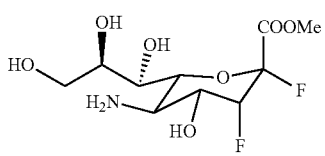

11

(m) treatment of compound 11 with 4-nitrophenylchloroformate in the presence of sodium bicarbonate to give compound 12;

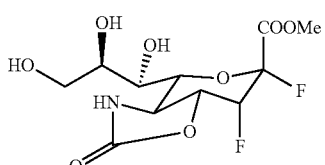

12

(n) treatment of compound 12 with 2,2'-dimethoxypropane by acid catalysis, followed by treatment with 4-nitrophenylchloroformate in pyridine to give compound 13;

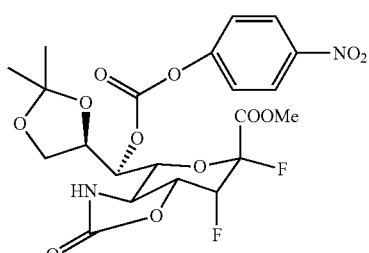

13

(o) treatment of compound 13 with propargyl amine in pyridine to give compound 14;

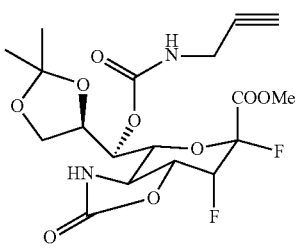

14

(p) treatment of compound 14 with trifluoroacetic acid to give compound 15;

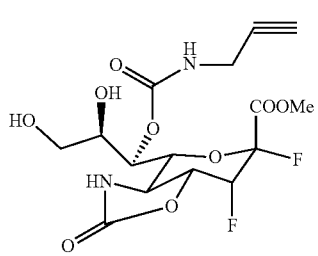

15

(q) treatment of compound 15 with acetic anhydride in pyridine to give compound 16;

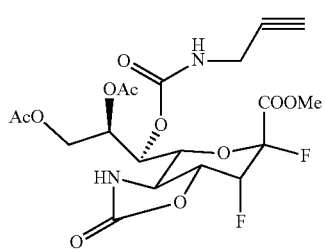

16

(r) treatment of compound 16 with acetyl chloride in diisopropylethylamine to give PDFSA-7-yne; and (s) saponification of PDFSA-7-yne to give DFSA-7-yne.

To examine the feasibility of DFSA-5-yne as an activity-based probe, the inhibition of various sialidases by DFSA-5-yne were evaluated using 2-(4-methylumbelliferyl)-α-D-N-acetylneuraminic acid (MUNANA) as the substrate. The sialidases used in this study are derived from a variety of species, including influenza virus (NA), bacteria (nanA, nanB, nanC, nanJ, nanI and nanH) and human (Neu1, Neu2, Neu3 and Neu4) sialidases.

All tested sialidases were sensitive to DFSA-5-yne with micro- to submicromolar half maximal inhibitory concentrations (Table 1), indicating that DFSA could be a potent activity-based probe for these enzymes. In contrast to the sensitive inhibition by DFSA, the ester-protected analog PDFSA-5-yne did not inhibit these sialidases (data not shown), suggesting that esterification of the hydroxy and carboxy groups in PDFSA prevents bindings to the sialidase active sites.

TABLE 1

$IC_{50}$ values (μM) of sialidase inhibition by DFSA-5-yne, DANA, Zanamivir, and Oseltamivir.[a]

| Sialidase[b] | DFSA-5-yne | DANA[c] | Zanamivir | Oseltamivir |
|---|---|---|---|---|
| NA | 51 ± 24 | 5.4 ± 1.6 | 0.005 | 0.003 |
| Neu1 | 10.4 ± 2.3 | >100 | >100 | >100 |
| Neu2 | 26.1 ± 12.8 | 24 ± 2.8 | 17 | >100 |
| Neu3 | 5.3 ± 3.2 | 2.4 ± 0.6 | 3 | >100 |
| Neu4 | 59.8 ± 1.3 | 4.3 ± 1.4 | 30.8 | >100 |
| nanA | 0.3 ± 0.1 | 9.3 | >100 | 3.8 ± 2.6 |
| nanB | 82 ± 22 | 25.4 | >100 | 14.2 ± 6.2 |
| nanC | 42.8 ± 17.5 | >100 | >100 | >100 |
| nanJ | 34.9 ± 4.2 | 4.5 | >100 | >100 |
| nanI | 25.5 ± 0.6 | 1.9 | 77 | >100 |
| nanH | 354 ± 146 | 15.7 | 83 | >100 |

[a]A fluorescent substrate, 2'-(4-methylumbelliferyl)-α-D-N-acetylneuraminic acid (MU-NANA), was used to determine the $IC_{50}$ values that are concentrations causing 50% inhibition of different sialidases.
[b]The sialidases used in this study are NA (influenza neuraminidase from A/WSN/1933/H1N1), Neu1-Neu4 (recombinant sialidases from human), nanA-nanC (recombinant sialidases of S. pneumoniae), and nanJ-nanH (recombinant sialidases from C. perfringens).
[c]DANA represents 2,3-didehydro-2-deoxy-N-acetylneuraminic acid.

To validate the sialidase labeling by DFSA-5-yne, formation of the fluorosialosyl-enzyme adducts by SDS-PAGE analyses were examined. All the bacterial sialidases formed DFSA adducts that were captured by azido-biotin and detected by the streptavidin specific reporting signals (FIG. 2A).

Figure 2:
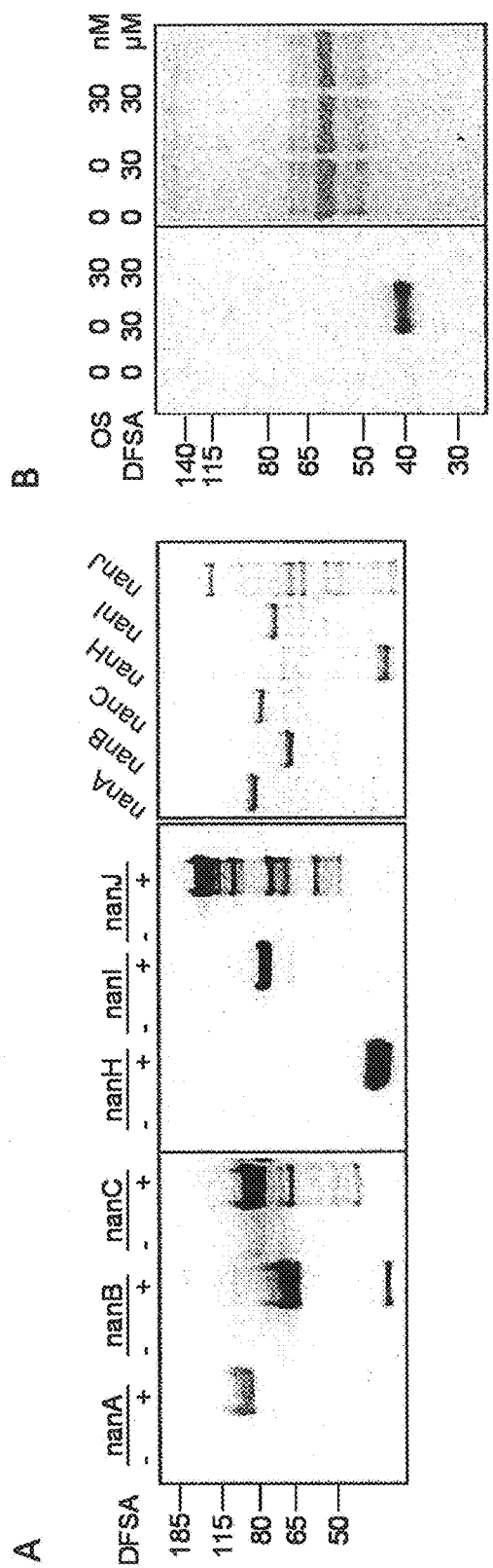
FIG. 2. Identification of sialidases by DFSA-5-yne adduct formation. Identification of sialidases by DFSA adduct formation. (2A) Recombinant sialidases produced in E. coli were briefly treated with DFSA, separated in SDS-PAGE, and transferred to PVDF membranes (left and middle panels) that were reacted with the click reaction reagent azido-biotin to ligate the biotin moiety to the alkyne group of the enzyme conjugate. The biotin modified sialidases present in the washed membrane were detected through the streptavidin conjugated HRP reporting system. These sialidase adducts were also shown by Coomassie blue staining (right panel). (2B) Detection of influenza NA was conducted after incubating influenza virus (A/WSN/1933/H1N1) samples with DFSA with or without addition of the specific inhibitor oseltamivir acid (OS) to compete with DFSA for binding to the active site (left panel). These total lysates were also shown by Coomassie blue staining (right panel). (2C) Human sialidase samples present in the lysates of 293T transfected or un-transfected cells (Mock) were treated with or without DFSA prior to SDS-PAGE analyses. The sialidases were also detected by immunoblot analyses of the flag epitope presented in Neu1, Neu2, Neu3 and Neu4. (2D) Labeling of human sialidases was also conducted by incubating PDFSA with sialidase-expressing 293T cells and processed for adduct detection similarly. The sialidases were also detected by immunoblot analyses of the flag epitope presented in Neu1, Neu2, Neu3 and Neu4. (2E) The DFSA-nanH adduct formation was shown to be proportional to the nanH used.
Figure 2:
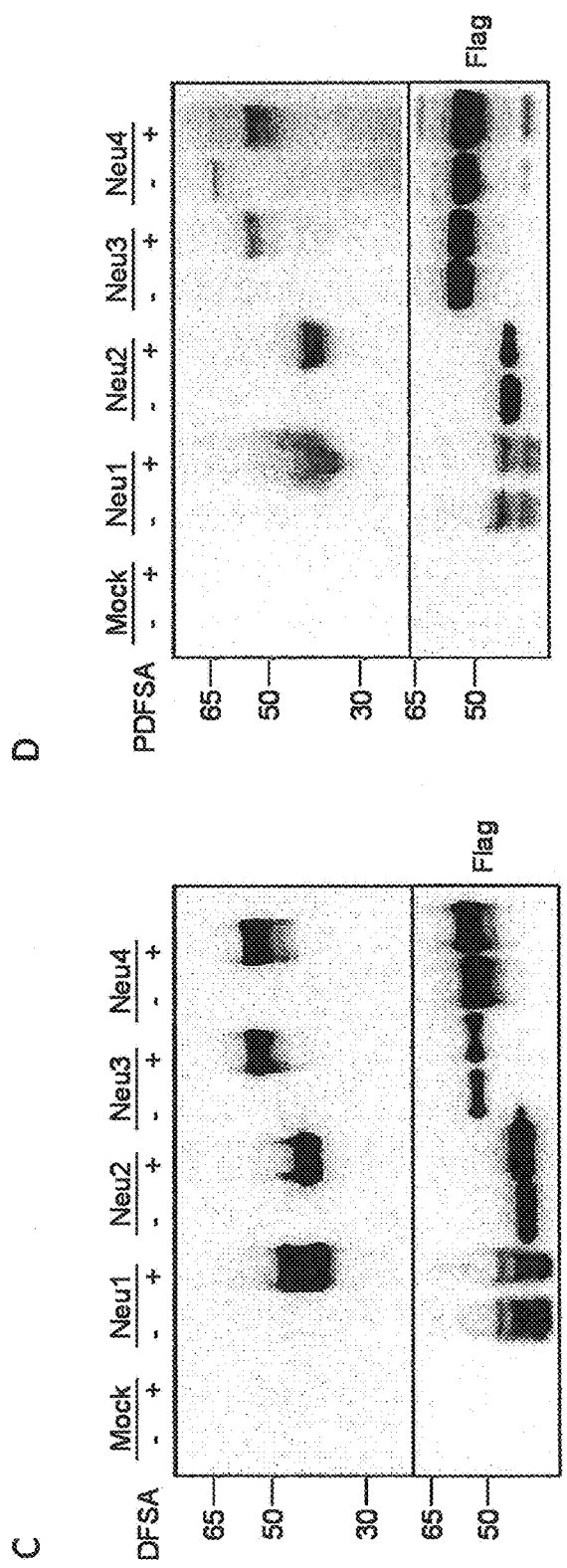
Figure 2:
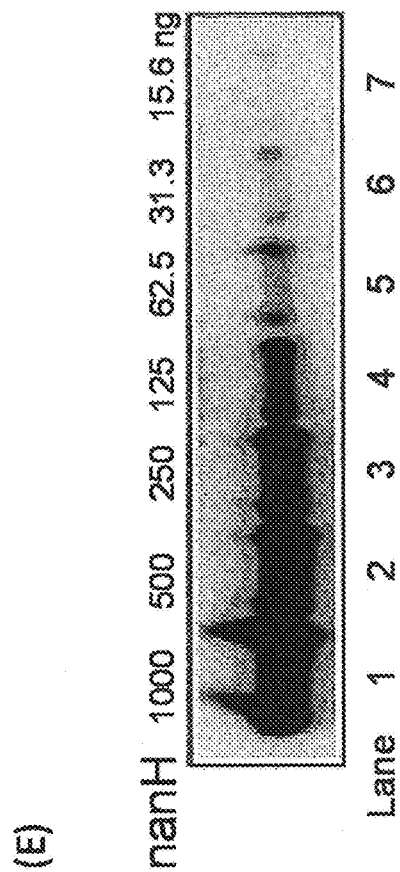

The influenza neuraminidase located at the surface of influenza virus (A/WSN/1933/H1N1) also formed a DFSA adduct that could be out competed by the neuraminidase inhibitor oseltamivir acid (OS), suggesting that DFSA interacted with neuraminidase at the active site (FIG. 2B).

Similar to the labeling of influenza neuraminidase by DFSA-5-yne, specific DFSA labeling was identified by four human sialidases in the crude extracts of transfected 293T cells (FIG. 2C).

Figure 3:
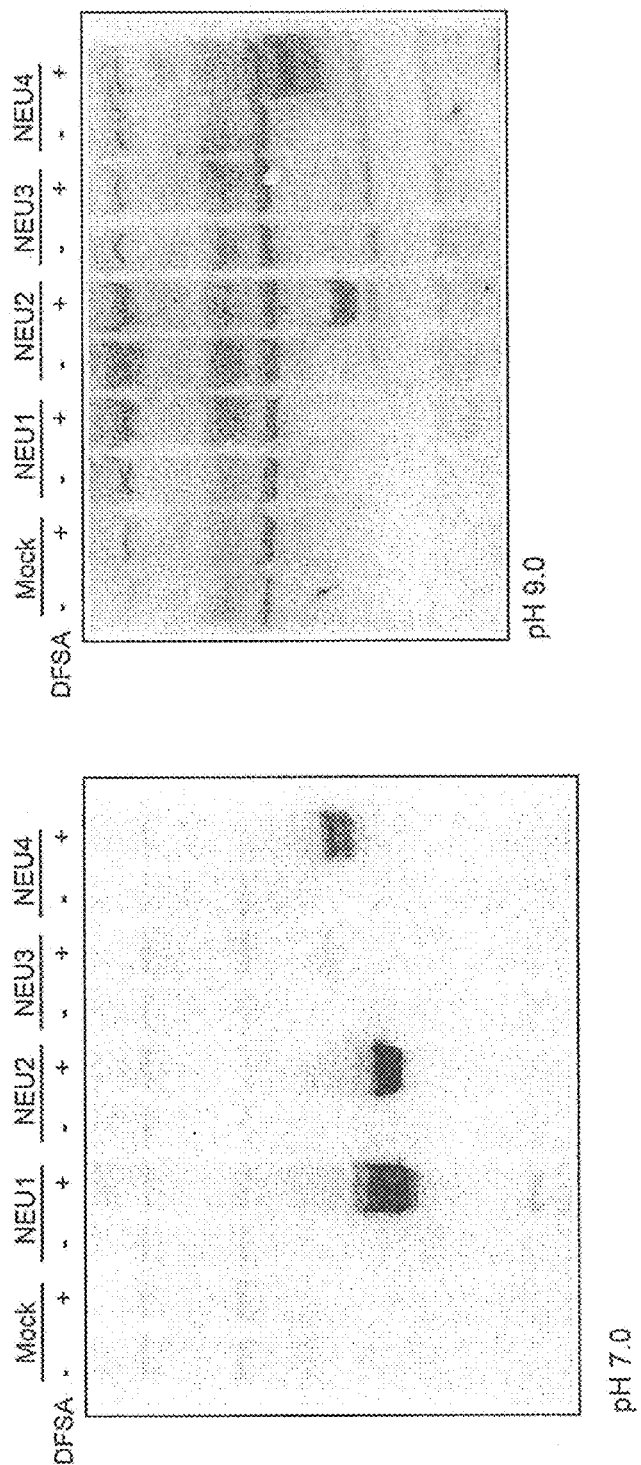
FIG. 3. pH dependent labeling of human sialidases in cell lysates. Lysates of recombinant sialidase expressing cells were collected in different buffers (pH 7.0 or 9.0) and incubated with DFSA (100 µM) to label sialidases.

The disclosure reveals that the DFSA labeling of human sialidases were sensitive to pH conditions. Neu1 and Neu3 were poorly labeled at pH 9. For Neu3, weak labeling was observed even at pH 7 (FIG. 3).

Using the bacterial nanH as an example, the DFSA labeled products were roughly proportional to the amounts of sialidase (FIG. 2E).

The disclosure provides LC-MS/MS analyses on the tryptic peptide fragments of the DFSA-labeled sialidases to identify the interacting amino acids. All six bacterial sialidase peptides were found to be labeled by the 3-fluorosialyl moiety at the tyrosine residues (Table 2).

TABLE 2

DFSA-labeled tryptic peptides from different sialidases.

| Sialidase | Tryptic peptide | Modified sites |
|---|---|---|
| nanA | [723]FAYNSIQEIGNGEYGIIYEHTEKGQNAYTISFR[755] (SEQ ID NO: 1) | Y725 |
| nanB | [628]YHYDIDIPSYGYAYSAITEIPNHHIGVIFEK[658] (SEQ ID NO: 2) | Y639 and Y641[a] |
| nanC | [708]YHHDVDYSNYGYSYSTITEIPNHEIGIMFEK[738] (SEQ ID NO: 3) | Y721 |

TABLE 2-continued

DFSA-labeled tryptic peptides from different sialidases.

| Sialidase | Tryptic peptide | Modified sites |
|---|---|---|
| nanI | $^{649}$IVKPGYYAYSCITE$^{762}$ (SEQ ID NO: 4) | Y657 |
| nanJ | $^{779}$TVKPGSFAYSCITEIPDGNIGIFYEGEGAGR$^{809}$ (SEQ ID NO: 5) | Y787 |
| nanH | $^{369}$IGGGYSCISFK$^{379}$ (SEQ ID NO: 6) | Y373 |

$^a$The LC-MS/MS analysis showed that DFSA was covalently linked to Tyr639 and Tyr641 in a ratio of 85:15.

For the profiling of intracellular sialidases, the probe needs to be cell permeable. However, being a hydrophilic compound, DFSA-5-yne is poorly permeable to cells. To enhance the cellular uptake, the ester-protected probe, PDFSA-5-yne, was used to test the labeling of intracellular sialidases expressed in 293T cells. In comparison with the sialidase labeling of cell extracts with DFSA-5-yne (FIG. 2C), similar results were observed of sialidase labeling after incubation of live cells with PDFSA-5-yne (FIG. 2D).

Figure 5:
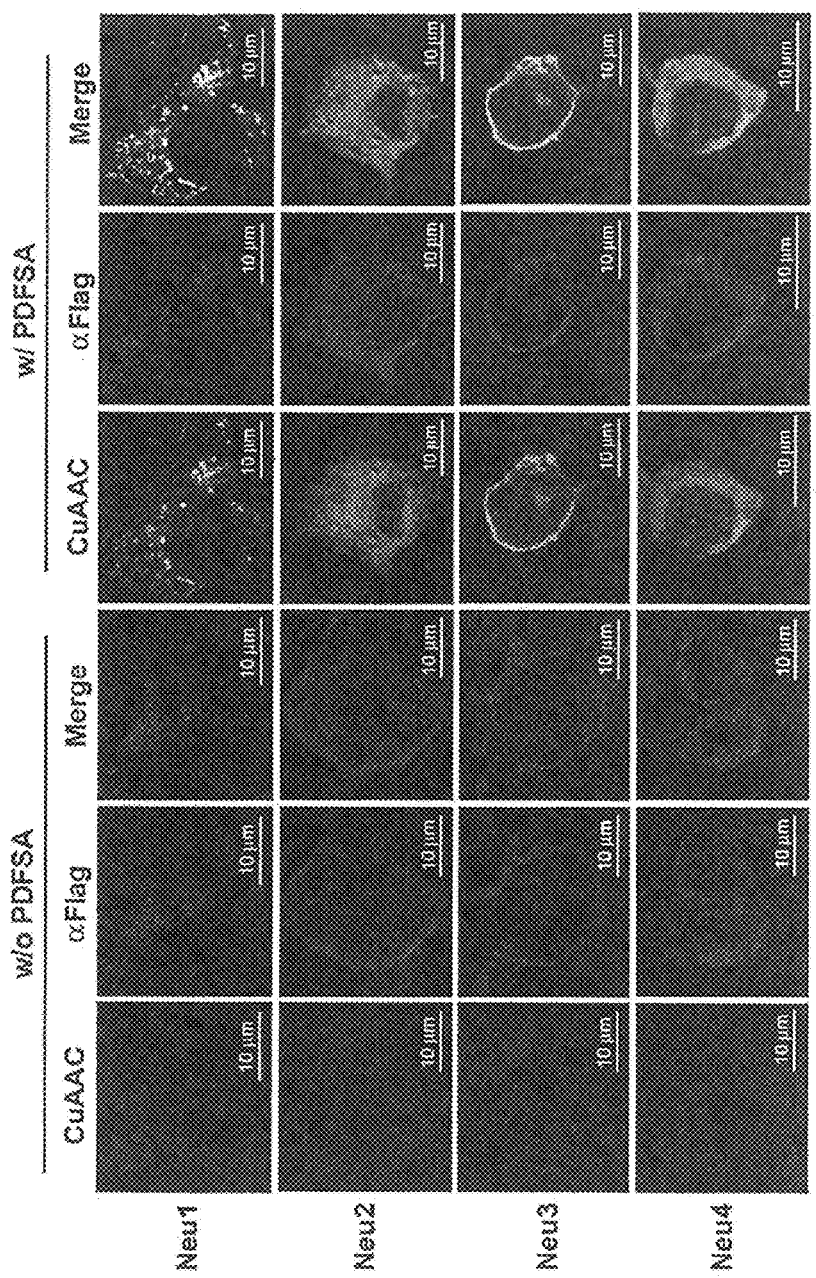
FIG. 5. Imaging analyses of sialidase-expressing 293T cells labeled by PDFSA. Live sialidase-expressing 293T cells were treated with PDFSA at 0.2 mM for 15 h. Cells were fixed, permeated, and biotin-tagged for confocal microscopy analyses. PDFSA-mediated sialidase labeling is shown in green, and flag-labeling is shown in red. Scale bars: 10 mm.

The success in sialidase labeling using PDFSA-5-yne prompted us to determine the cellular localizations of the expressed sialidase activities by incubating live cells with PDFSA and examining the cellular location of the sialidase adducts in fixed and permeated cells (FIG. 5). The sialidase activities were detected as green signals through the PDFSA mediated sialidase labeling, the sialidase proteins were detected as red signals by staining with anti-flag antibody.

FIG. 5 shows that the sialidase signals are located in lysosomes for Neu1-/Neu4-, cytosol for Neu2-, and plasma membrane for Neu3-expressing cells, consistent with the previous reports. (T. Miyagi and K. Yamaguchi, *Glycobiology* 2012, 22, 880. T. Miyagi, et al. *Glycoconj. J.* 2004, 20, 189.)

Analyses of sialidase activity and Neu1 in expressing cells showed high co-localization at ~85%. Similar high co-localization was found in Neu2 and Neu3 expressing cells, suggesting that the observed sialidase activity profiling is correlated with the enzyme distribution.

The activity and co-localization for the Neu4 expressing cells is lower at only 68%. The possible explanation is that Neu4 is expressed in long and short isoforms, differing in the presence and absence of a 12-amino-acid sequence at the N-terminus. (V. Seyrantepe, et al. *J. Biol. Chem.* 2004, 279, 3702. K. Yamaguchi, et al. *Biochem. J.* 2005, 390, 85. A. Bigi, et al. *Glycobiology* 2010, 20, 148.) The Neu4 long is mainly located in mitochondria and has the N-terminal flag-tag, while the Neu4 short targets membrane and does not have the flag-tag. The fact that these two expressed Neu4 sialidase forms are different in cellular localizations and flag-antigen expressions could explain the apparent low co-localization observations.

The results of profiling sialidase activity in the four sialidases thus suggest that PDFSA is a useful probe for living cells.

Figure 6:
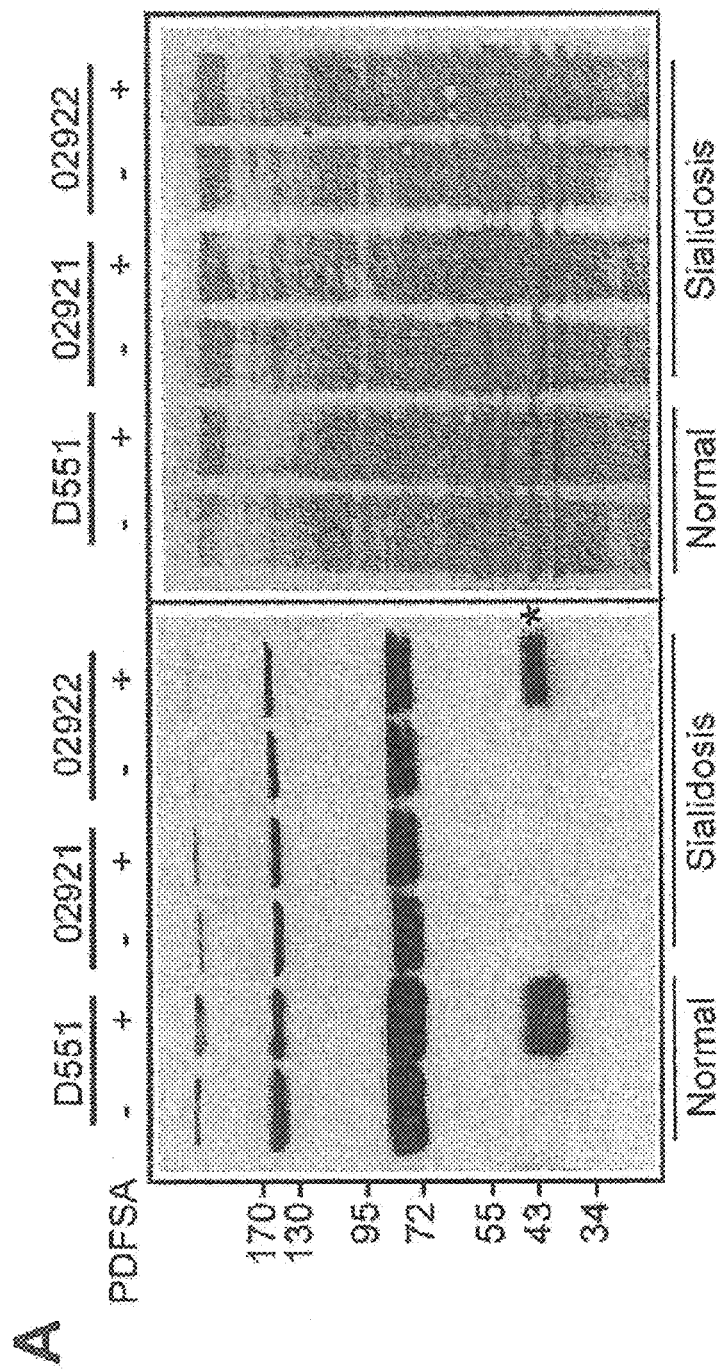
FIG. 6. Profiling of sialidase changes in the fibroblasts of sialidosis patients. (6A) Fibroblast cells derived from normal (D551) or sialidosis paitents (GM02921 & GM02922) were cultured for in situ sialidase labeling with PDFSA (10 µM). The relevant sialidase labeling signals are marked with stars (left panel). These total lysates were also shown by DB71 staining (right panel). (6B) Fibroblast cells derived from normal (D551) or sialidosis paitents (GM02921 & GM02922) were analyzed by Anti-Neu1 antibody. (6C) Cellular sialidase activities were measured using MUNANA as the substrate and compared to the sialidase activities in extracts of cells cultured with or without prior incubation with PDFSA. Values are means±SEM of three independent experiments.
Figure 6:
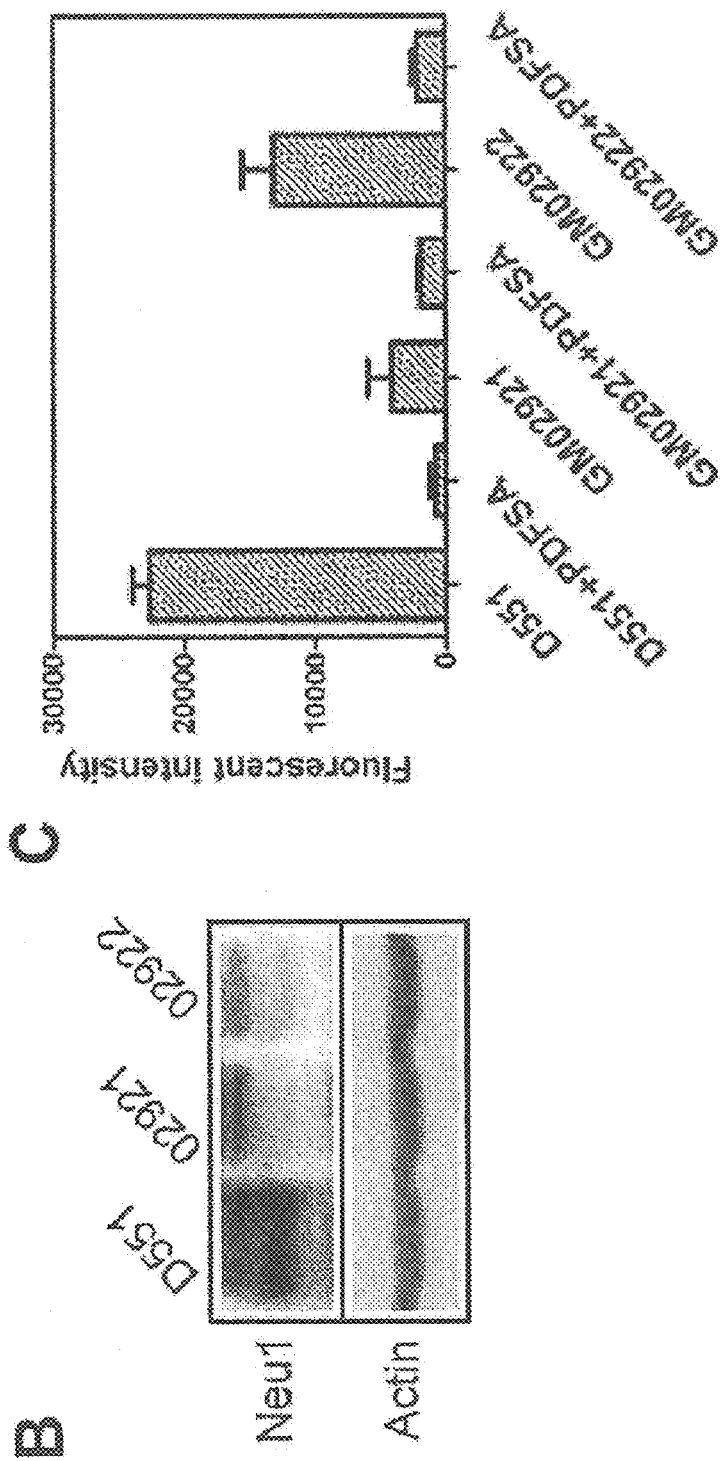

Sialidosis is an inherited lysosomal storage disease usually due to Neu1 deficiency. Neu1 activity differences in fibroblasts of normal and sialydosis patients were examined by live cell labeling using PDFSA-5-yne. The sialidase labeling was significantly reduced in the more sever sialidosis (GM02921) fibroblast cells than the milder sialydosis (GM02922) cells (FIG. 6A). (A. V. Pshezhetsky and M. Potier, *J. Biol. Chem.* 1996, 271, 28359.)

The results of the sialidase activity difference observed by PDFSA labeling are consistent with the conventional activity measurement of the cell extracts using MUNANA as the substrate (FIG. 6C). The similar sialidase activity determined by adduct formation through PDFSA-5-yne treatment and by MUNANA processing using cell lysates suggest that the intracellular sialidase was effectively modified by adduct formation.

Figure 4:
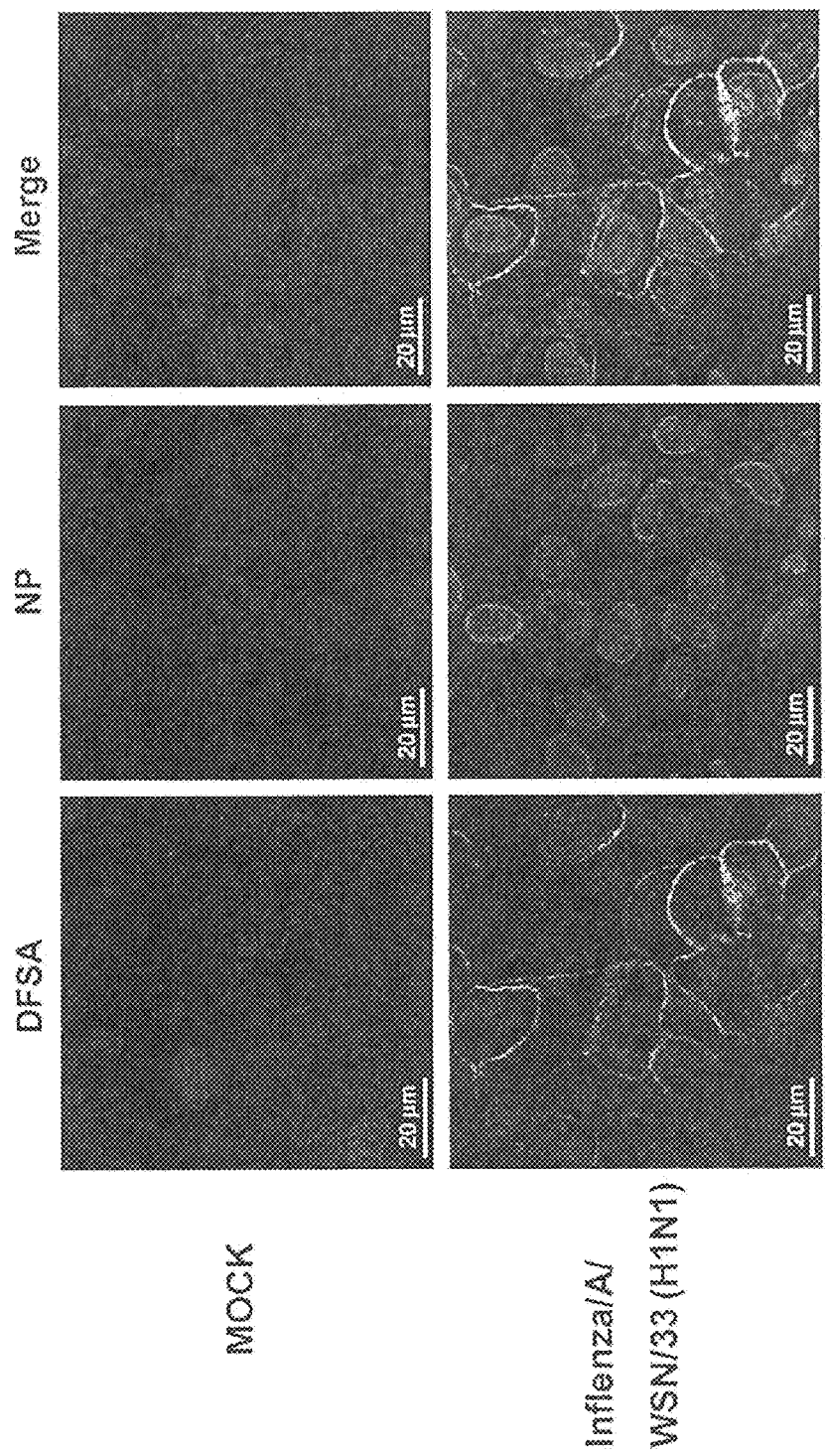
FIG. 4. Visualization of influenza infected cells using DFSA labeling. Fluorescence image of influenza infected cells that were treated with 30 µM DFSA, biotin-tagged, and stained with FITC-tagged streptavidin. The influenza neuraminidase is shown in green, and influenza nucleoprotein (NP) is shown in red after anti-NP monoclonal antibody staining. Cell nuclei are shown in blue by DAPI staining. Scale bars: 20 µm. Mock: non-infected cells. DAPI: 4',6-diamidino-2-phenylindole.

DFSA was also successfully used to image the influenza virus infected cells that express neuraminidase on the cell surface accessible to DFSA labeling (FIG. 4).

To determine the sensitivity of influenza detection using DFSA, DFSA-5-yne with varied quantities of influenza viruses were incubated and then immobilized the viral samples on membrane followed by similar detection procedures used in SDS-PAGE. This procedure allowed the detection of influenza virus present at $10^4$ or higher titers (FIG. 7A).

Figure 7:
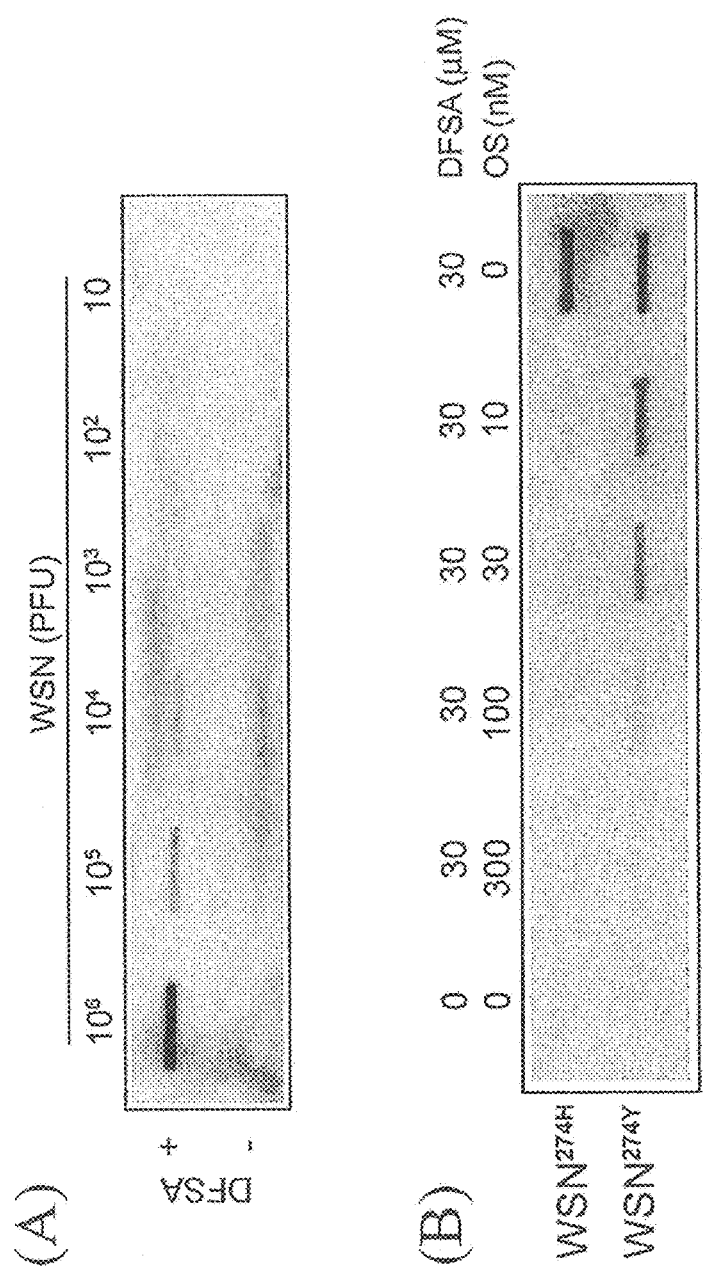
FIG. 7. Detection of influenza virus with DFSA on PVDF membrane. (A) Detection limit of influenza virus by DFSA labeling. (B) Differentiation of oseltavimir-sensitive (WSN$^{274H}$) and oseltamivir-resistant (WSN$^{274Y}$) influenza viruses by DFSA staining in the presence of competing OS (osletamivir). PVDF: polyvinylidene fluoride.
Figure 8:
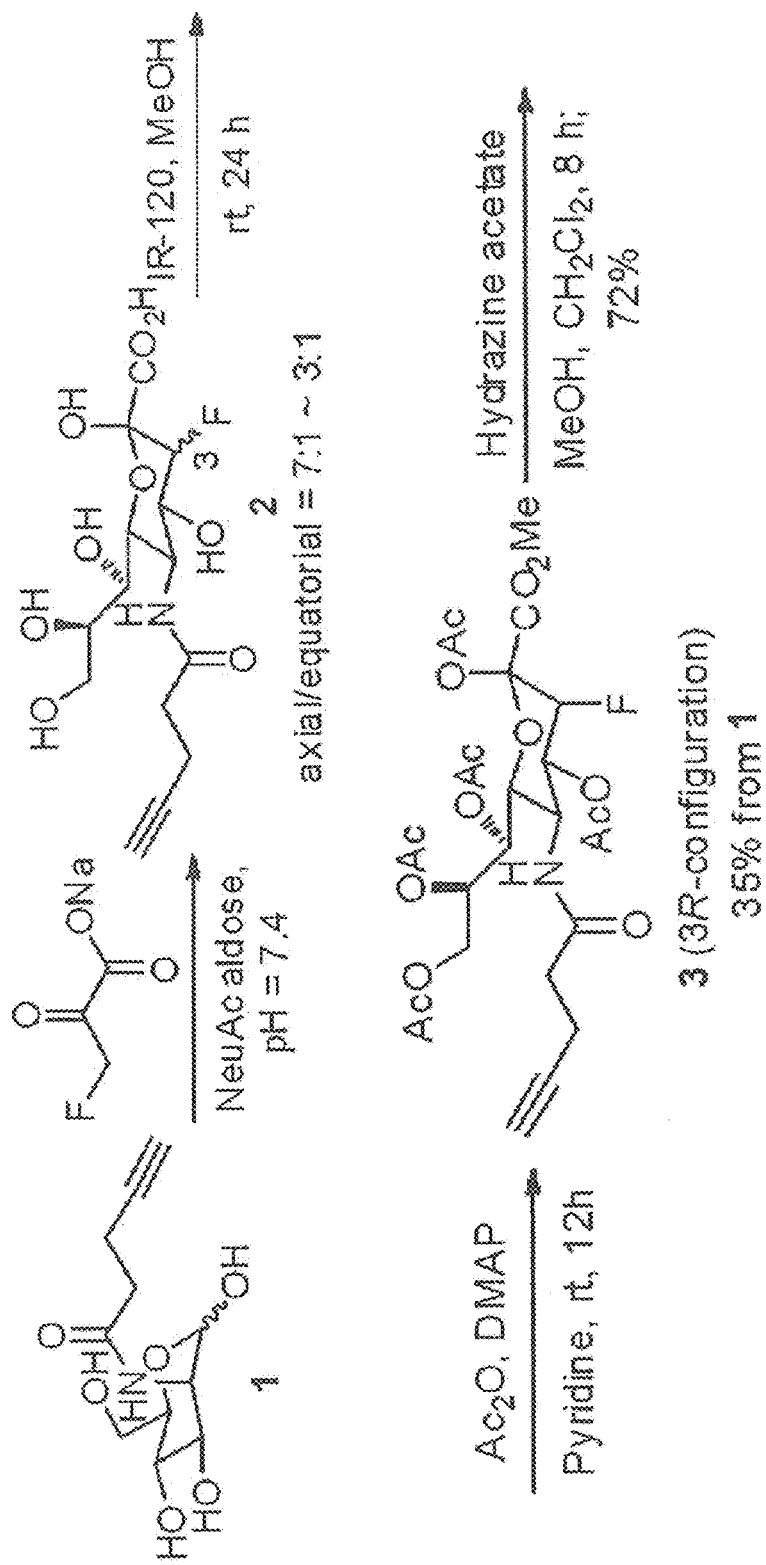
FIG. 8. Schematic diagram of a method for synthesis of PDFSA and DFSA.
Figure 8:
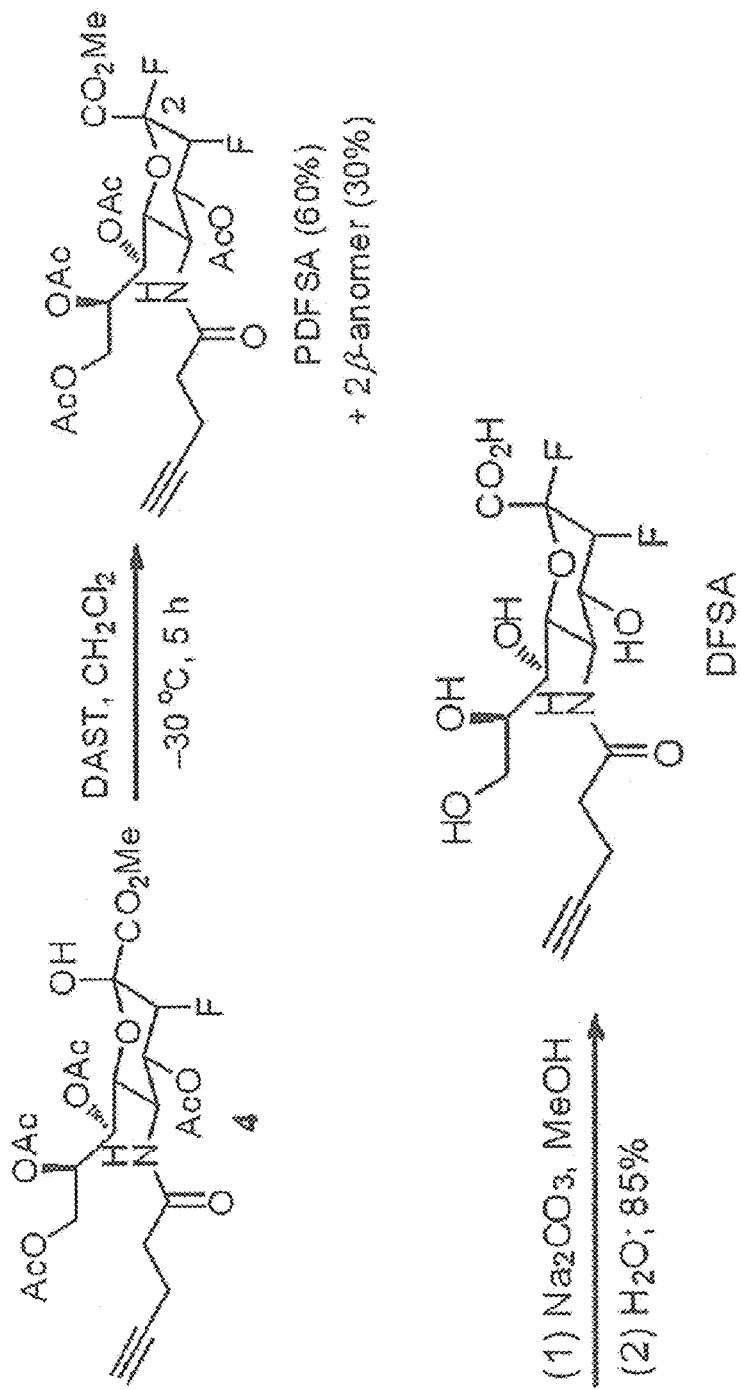

DFSA-5-yne is shown to bind at the active site of influenza neuraminidase, and the binding can be competitively inhibited by OS (FIG. 7B). It was expected that OS can inhibit the DFSA labeling to oseltamivir-sensitive ($OS^s$) viruses competitively because both compounds bind the active site of neuraminidase. However, for oseltamivir-resistant ($OS^r$) influenza viruses that are the prevailing clinical isolates for $H_1N_1$ since 2008, (T. G. Sheu, et al. *Antimicrob. Agents Chemother.* 2008, 52, 3284.) OS cannot bind the active site of the mutant neuraminidase and should not inhibit the DFSA binding to influenza. Indeed, both $OS^s$ and $OS^r$ H1N1 influenza viruses were labeled by DFSA in the absence of OS, but only the $OS^r$ virus was detectable by DFSA labeling in the presence of competing OS, suggesting the possibility of using DFSA probe to detect drug resistant influenza strains.

The disclosure provides an activity-based sialidase probe DFSA-5-yne by using the 3-fluorosialyl fluoride as the mechanism-based inhibitor and by incorporating an alkyne group for reporter ligation. Biochemical analyses of the DFSA inactivated sialidases by LC-MS/MS analysis showed that the tyrosine residues in the enzyme active site were specifically labeled by DFSA. The ability of DFSA-5-yne to label all sialidases from viral, bacterial, and human enzymes suggests that DFSA-5-yne may be used as a general sialidase probe for various applications.

DFSA-5-yne is advantageous as a general ABPP because of its small size. Introduction of the ester-protected PDFSA-5-yne enhances cell permeable properties and allows the profiling of intracellular sialidases. The ability of PDFSA-5-yne to probe intracellular sialidases using living cells has an added advantage over the labeling using cell lysates, particularly for unstable sialidases. Since sialidases are known to be involved in various diseases, these probes can be useful in developing sialidase-based diagnoses.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1: Methods and Materials

Unless otherwise noted, all compounds and reagents were purchased from Acros or Sigma-Aldrich. All chemicals were purchased as reagent grade and used without further purification. N-Acetylneuraminic acid aldolase was purchased from ToYoBo STC. Reactions were monitored with analytical thin-layer chromatography (TLC) in EM silica gel 60 F254 plates and visualized under UV (254 nm) and/or staining with acidic ceric ammonium molybdate or ninhydrin. Flash column chromatography was performed on silica gel 60 Geduran (35-75 μm, EM Science). $^1$H NMR spectra were recorded on a Bruker DRX-400 (400 MHz) spectrometer at 20° C. Chemical shifts were assigned according to the CHCl$_3$ (δ=7.24 ppm). $^{13}$C NMR spectra were obtained using Attached Proton Test (APT) on a Bruker DRX-400 (100 MHz) spectrometer and were reported using the signal of CDCl$_3$ (δ=77.0 ppm of central line) for calibration. Mass spectra were obtained by the analytical services of The Scripps Research Institute (Agilent ESI-TOF) and The Genomics Research Center (Acadmia Sinica) (LTQ Orbitrap XL ETD). Fluorescence spectra were obtained on a Molecular Devices Spectramax M5 spectrometer. Protease inhibitors were purchased from Roche Applied Sciences, PVDF membranes were from Millipore. NuPAGE® Bis-Tris Mini gels (4-12%), PBS and cell culture media and reagents were from Invitrogen. Protein concentration was measured by either BCA protein assay (Thermo Scientific) or Bradford assay (Bio-rad). GM02921 and GM02922 were obtained from the NIGMS Human Genetic Mutant Cell Repository. Chemiluminescence on protein blots was visualized and quantified using FUJI LAS3000 imaging system (Fujifilm). Confocal microscopy of sialidase-expressing 293T cells were obtained using Leica TCS-SP5-MP-SMD.

Example 2: Methyl 5-(pent-4-ynamido)-2,4,7,8,9-penta-O-acetyl-3,5-dideoxy-3-fluoro-D-erythro-α-L-manno-non-2-ulopyranosonate (4)

A mixture of N-4-pentynoylmannosamine (460.0 mg, 1.78 mmol) (Z. Zhou and C. J. Fahrni, J. Am. Chem. Soc. 2004, 126, 8862.), 3-fluoropyruvic acid (as the sodium salt, 458.2 mg, 3.56 mmol), NaN$_3$ (1%, 500 μL), and N-acetylneuraminic acid aldolase (200 U), in potassium phosphate buffer (pH 7.4, 0.05 mmol/L, 25.0 mL), was incubated at room temperature for 3 days. The mixture was concentrated. The residue was applied to a Dowex® column (1×2, 200 mesh), and eluted with water and formic acid (0.1-1.0 mol/L) sequentially. Fractions containing the desired product 2 were pooled, and concentrated under reduced pressure. The diastereomeric ratio (axial/equatorial=7:1) 2 was determined by NMR analyses.

To the crude product 2 were added MeOH (30 mL) and ion exchange resin Amberlite® IR 120-H (500 mg). The mixture was stirred at room temperature for 24 h, and filtered through a pad of Celite, giving ester 3. MeOH was removed, and the residue was treated with pyridine (25 mL), DMAP (10.0 mg) and Ac$_2$O (10 mL). The mixture was stirred at room temperature for 12 h. After that, pyridine was removed under vacuum first and the residue was taken up in EtOAc (100 mL) and washed with 5% citric acid (×3), 10% NaHCO$_3$ (×3) and brine. The combined organic layers were dried over anhydrous MgSO$_4$, filtered and concentrated. The single diastereomer 4 (366.6 mg, 35% overall yield) was obtained as white foam after silica gel column chromatography eluted with EtOAc/hexane (4:1). TLC (EtOAc/hexane=3:1) R$_f$=0.31. $^1$H-NMR (CDCl$_3$, 400 MHz) δ 5.66 (d, J=9.0 Hz, 1H), 5.55 (d, J=2.4, 10.9, 27.7 Hz, 1H), 5.34 (dd, J=1.9, 5.3 Hz, 1H), 5.11 (m, 1H), 4.92 (dd, J=2.4, 49.1 Hz, 1H), 4.51 (dd, J=2.4, 12.5 Hz, 1H), 4.25 (dd, J=1.3, 10.6 Hz, 1H), 4.17 (dd, J=6.4, 12.5 Hz, 1H), 4.13 (m, 1H), 2.53-2.39 (m, 2H), 2.37-2.26 (m, 2H), 2.16 (s, 3H), 2.13 (s, 3H), 2.07 (s, 3H), 2.01 (s, 3H), 1.99 (s, 3H), 1.97 (t, J=2.5 Hz, 1H). $^{13}$C-NMR (CDCl$_3$, 100 MHz) δ 171.2, 170.6, 170.5, 170.3, 170.2, 167.1, 165.1, 95.1 (d, J=29.0 Hz), 86.9 (d, J=184.0 Hz), 82.7, 71.6, 71.1, 69.6, 68.2, 68.1, 68.0, 62.1, 53.5, 45.7, 35.4, 0.8 (2×), 20.7, 20.5, 14.6. $^{19}$F-NMR: (CDCl$_3$, 282.4 MHz) δ−209.1 (dd, J=28.0, 52.0 Hz) HR-ESI MS calcd for C$_{25}$H$_{33}$NO$_{14}$ [M+H]$^+$: 548.1774; found: 548.1770.

Example 3: Methyl 5-(pent-4-ynamido)-4,7,8,9-tetra-O-acetyl-3,5-dideoxy-3-fluoro-D-erythro-α-L-manno-2-non-2-ulopyranosonate (5)

To a solution of compound 4 (165.0 mg, 0.28 mmol) in 10 mL of CH$_2$Cl$_2$ was added hydrazine acetate (116.0 mg, 1.26 mmol) in 2.0 mL of MeOH. The mixture was stirred at 0° C. for 8 h, and then concentrated under reduced pressure. The product 5 (110.0 mg, 72%) was obtained as an oil after silica gel column chromatography eluted with EtOAc/hexane (4:1). TLC (EtOAc/hexane=3:1) R$_f$=0.31. $^1$H-NMR (400 MHz, CDCl$_3$+CD$_3$OD) δ 5.46 (dd, J=2.4, 4.4 Hz, 1H), 5.39-5.26 (m, 2H), 4.97 (dd, J=2.4, 50 Hz, 1H), 4.76 (m, 1H), 4.46-4.34 (m, 2H), 4.20 (dd, J=7.4, 12.4 Hz, 1H), 3.85 (s, 3H), 2.54-2.40 (m, 2H), 2.36-2.30 (m, 2H), 2.17 (s, 3H), 2.11 (s, 3H), 2.09 (s, 3H), 2.07-2.05 (m, 4H). $^{13}$C-NMR (100 Hz, CDCl$_3$+CD$_3$OD) δ 173.7, 172.4, 171.9, 171.7, 171.6, 168.7, 95.5 (d, J=20.0 Hz), 88.5 (d, J=146.0 Hz), 83.5, 72.6, 71.2, 71.1, 71.0, 70.0, 69.3, 63.6, 53.4, 45.4, 36.1, 21.1 (2×), 21.0, 15.4. $^{19}$F-NMR (CDCl$_3$, 282.4 MHz) δ −205.3 (dd, J=28.0, 52.0 Hz). HR-ESI MS calcd for C$_{23}$H$_{31}$FNO$_{13}$ [M+H]$^+$: 522.1618; found: 522.1211.

Example 4: Methyl 5-(pent-4-ynamido)-4,7,8,9-tetra-O-acetyl-2,3,5-trideoxy-3-fluoro-D-erythro-β-L-manno-non-2-ulopyranosylonate fluoride (PDFSA-5-yne)

To a solution of compound 5 (75.0 mg, 0.14 mmol) in 5 mL of CH$_2$Cl$_2$ was added 19 μL (0.19 mmol) of DAST at −30° C., and stirred for 5 h. The reaction was quenched by adding small amount of silica gel and 1.5 mL of MeOH. The mixture was concentrated under reduced pressure. PDFSA-5-yne (α-anomer, 46.0 mg, 60%) and the β-anomer (23.0 mg, 30%) were isolated by silica gel column chromatography eluted with EtOAc/hexane (5:1).

PDFSA-5-yne (α-anomer): TLC (EtOAc/hexane=3:1) R$_f$=0.33. $^1$H-NMR (400 MHz, CDCl$_3$) δ 5.79 (d, J=8.9 Hz, 1H), 5.46 (dd, J=10.7, 25.6 Hz, 1H), 5.36-5.28 (m, 1H), 5.10 (ddd, J=2.6, 2.7, 50.7, 1H), 4.34 (d, J=10.9 Hz, 1H), 4.29 (dd, J=1.7, 12.4 Hz, 1H), 4.16 (dd, J=4.2, 12.4 Hz, 1H), 4.08 (m, 1H), 3.87 (s, 3H), 2.52-2.37 (m, 2H), 2.36-2.23 (m, 2H), 2.12 (s, 3H), 2.08 (s, 3H), 2.06 (s, 3H), 1.99 (s, 3H), 1.97 (t, J=2.5 Hz, 1H). $^{13}$C-NMR (100 Hz, CDCl$_3$) δ 171.3, 170.5 (2×), 170.4, 170.2, 164.3 (d, J=20.0 Hz), 104.5 (dd, J=13.0, 179.0 Hz), 85.4 (dd, J=16.0, 154.0 Hz), 82.7, 72.5, 69.6, 69.0, 68.3 (d, J=5.0 Hz), 67.0, 61.8, 53.7, 45.5 (d, J=3.0 Hz), 35.4, 20.7, 20.6 (2×), 20.5, 14.6. $^{19}$F-NMR: (CDCl$_3$, 282.4

MHz) δ −123.3 (d, J=12.0 Hz), −217.1 (ddd, J=12.0, 24.0, 52.0 Hz). ESI-HRMS calcd for $C_{23}H_{30}F_2NO_{12}$ [M+H]$^+$: 550.1730; found: 550.1736.

PDFSA-5-yne (β-Anomer): TLC (EtOAc/hexane=3:1) $R_f$=0.37. $^1$H-NMR (400 MHz, CDCl$_3$) δ 5.68 (d, J=9.7 Hz, 1H), 5.42 (dd, J=2.1, 6.3 Hz, 1H), 5.38 (m, 1H), 5.25 (m, 1H), 5.10 (dd, J=2.3, 48.6 Hz, 1H), 4.48 (dd, J=2.6, 12.6 Hz, 1H), 4.43 (dd, J=10.5, 20.8 Hz, 1H), 4.32 (d, J=10.7 Hz, 1H), 4.11 (dd, J=10.5, 20.8 Hz, 1H), 3.86 (s, 3H), 2.38-2.53 (m, 2H), 2.23-2.37 (m, 2H), 2.13 (s, 3H), 2.09 (s, 3H), 2.04 (s, 3H), 2.03 (s, 3H), 1.99 (t, J=2.6 Hz, 1H). $^{13}$C-NMR (100 Hz, CDCl$_3$) δ 171.1, 170.6, 170.5, 170.2, 169.9, 162.6 (d, J=21.0 Hz), 105.0 (dd, J=23.0, 183.0 Hz), 84.6 (dd, J=35.0, 147.0 Hz), 82.84, 72.7 (d, J=2.0 HZ), 72.3 (d, J=2.0 Hz), 69.6, 68.4 (d, J=14.0 Hz), 67.1, 62.1, 53.7, 44.5, 35.4, 20.7 (3×), 20.6, 14.6. $^{19}$F-NMR: (CDCl$_3$, 282.4 MHz) δ −122.4 (d, J=20.0 Hz), −207.2 (d, J=16.0 Hz).

Example 5: 5-(Pent-4-ynamido)-2,3,5-trideoxy-3-fluoro-D-erythro-β-L-manno-non-2-ulopyranosylonic fluoride (DFSA-5-yne)

To a solution of PDFSA-5-yne (42.0 mg, 0.076 mmol) in 5 mL of CH$_3$OH was added Na$_2$CO$_3$ (32.4 mg, 0.31 mmol) at room temperature for 1 h. H$_2$O (1 mL) was added, and the mixture was left at room for 2 h. The mixture was neutralized by ion exchange resin Amberlite® IR 120-H, and filtered through a pad of Celite. The filtrate was concentrated under reduced pressure, and the crude product was chromatographed on a silica gel 100 reversed-phase C18 column (H$_2$O to 10% aqueous MeOH) to yield product DFSA (23.7 mg, 85%) as a white foam. $^1$H-NMR (400 MHz, D$_2$O) δ 5.24 (ddd, J=2.5, 2.5, 51.3 Hz, 1H), 4.12-4.37 (m, 2H), 3.82-3.93 (m, 3H), 3.61-3.72 (m, 2H), 2.51-2.60 (m, 4H), 2.42 (s, 1H). $^{13}$C-NMR (150 Hz, D$_2$O) δ 175.6, 168.2 (d, J=40.6 Hz), 106.1 (dd, J=15.5, 218.1 Hz), 88.4 (dd, J=18.0, 183.5 Hz), 83.3, 72.7 (d, J=3.3 Hz), 70.3 (d, J=5.6 Hz), 68.6 (dd, J=5.6, 17.8 Hz), 67.8, 63.0, 48.8, 46.8 (d, J=3.3 Hz), 34.6 (d, J=7.1 Hz), 14.5. $^{19}$F-NMR (CDCl$_3$, 282.4 MHz) δ −121.3 (d, J=12.0 Hz), −218.0 (ddd, J=12, 28, 52 Hz). HR-ESI MS calcd for $C_{14}H_{20}F_2NO_8$ [M+H]$^+$: 368.1151; found: 368.1152.

Example 6: Cloning of Bacterial Sialidases

The cDNA of sialidases nanA (SP1693), nanB (SP1687) and nanC (SP1326) were amplified by PCR from *Streptococcus pneumonia* TIGR4 genomic DNA (ATCC ATCC BAA-334). Similarly, the cDNA of sialidases nanH (CPF 0985), nanI (CPF 0721) and nanJ (CPF 0532) were from *Clostridium perfringens* NCTC 8237 genomic DNA (ATCC 13124D-5) by specific primers (Table S3). The obtained cDNAs were then cloned into modified form of pET47b+ (Novagen, Madison, Wis.) for expressions in *E. coli*. The hydrophobic regions at the N-terminus of those sialidases predicted to be a signal peptide by SignalIP were not included in the primers during cloning. All these bacterial sialidases were expressed with N-terminal His tag for protein purification and antibody identification.

Example 7: Expression of Sialidase in *E. coli* and Purification of the Recombinant Sialidases All sialidase genes were obtained via PCR from genomic DNA or cDNA library by respective primer (Table S3). The PCR products were ligated into the modified form of pET47b vector and confirmed by DNA sequencing. The plasmids with correct sequences were transformed into ArcticExpress/RIL competent cells by chemical transformation method. Single colonies were picked and cultured in TB medium with kanamycin overnight. The cell cultures into fresh TB medium, were induced by 0.1 mM IPTG and to grow at 16° C. for 24 h. *E. coli* cells were harvested and disrupted in a buffer containing 50 mM sodium phosphate buffer, pH 8.0, 300 mM sodium chloride, and 10 mM imidazole by microfluidizer and clarified by Centrifugation. The expressed sialidases were purified by Ni-NTA agarose. The protein concentration was determined by Qubit Protein Quantitation (Invitrogen, CA), and purity was confirmed by SDS-PAGE.

Example 8: Cloning of Human Sialidase

The cDNA of human sialidases, Neu1, Neu2 and Neu4 were amplified from MGC clone (Clone ID: 40004620 and 40125765, respectively) by PCR and sub-cloned into modified form of expression vector, pCMV-Tag 2 (Sigma, St. Louis, Mo.) with N-terminal FLAG tag, whereas Neu1 with both FLAG tags in N- and C-terminals (Clone ID: 3506824) by primer addition. Neu3 cDNA was synthesized according to its sequence (Genbank: BC144059.1) and cloned as other three sialidases. All clones are confirmed by DNA sequencing, and sialidase expressions confirmed by FLAG-specific antibody.

Example 9: Determination of IC$_{50}$ of DFSA and PDFSA

Sialidase inhibition was determined by mixing inhibitor and neuraminidase for 10 min at room temperature, followed by the addition of 200 μM of substrate MUNANA. Inhibitor IC$_{50}$ value was determined from the dose-response curves by plotting the percent inhibition of NA activity versus inhibitor concentrations using Graph Pad Prism 4.

Example 10: Membrane Click Reaction

The PVDF membranes were blocked with blocking buffer 5% BSA/PBST (0.1% Tween 20/PBS) and streptavidin blocking buffer 0.02% streptavidin/3% BSA/PBST (0.1% Tween 20/PBS) for 1 h, respectively. The membranes were washed twice with PBS for 5 min. The protein side of the PVDF membrane was faced down to immerse in the click reaction mixture (0.1 mM azido-biotin, 0.1 mM tris-triazole ligand, 1 mM CuSO$_4$, 2 mM sodium ascorbate; with 1 mL for a blot of a minigel size) and incubated at room temperature for 1 h. After washing with PBST twice, the membrane was probed with peroxidase-conjugated streptavidin for biotin labels on blots. The signals were detected by ECL system.

Example 11: Labeling of Bacteria Sialidase, Influenza Neuraminidase, and Recombinant Human Sialidases Purified bacteria sialidases (1 μg) were incubated with DFSA (0.1 mM) at room temperature for 1 h, and separated on 4-12% NuPAGE (Invitrogen). 5×10$^5$ influenza viruses were incubated with DFSA (0.1 mM) at room temperature for 1 h, and separated on 4-12% NuPAGE (Invitrogen). Sialidase transfectant 293T cells were lysed by different lysis buffers: pH4.5 (1% NP-40, 100 mM NaOAc, 150 mM NaCl, 3 mM KCl, pH 4.5, 1×EDTA-free protease inhibitor cocktail from Roche), pH 7.4 buffer (1% NP-40, 25 mM Tris, 150 mM NaCl, 3 mM KCl, pH 7.4, 1×EDTA-free protease inhibitor cocktail from Roche), and pH 9.0 buffer (1% NP-40, 25 mM Tris, 150 mM NaCl, 3 mM KCl, pH 9.0, 1×EDTA-free protease inhibitor cocktail from Roche). The lysates were collected and incubated with DFSA (0.1 mM) at 37° C. for 1 h. Following incubation, the samples were clarified, and protein concentrations were determined by bicinchoninic acid protein assay kit (Pierce). For each sample, 20 μg total lysate was separated on 4-12% NuPAGE (Invitrogen). After electrophoresis, the gels were blotted onto PVDF membranes (Millipore). Click reactions were performed on the PVDF membranes, and labeling signals were processed and analyzed by chemiluminescence detector.

Example 12: In Situ Labeling of Sialidase Expressing Cells with PDFSA

Sialidase transfectant 293T cells, normal (D551) and sialidosis fibroblasts/(GM02921 and GM02922) were incubated with PDFSA (0.2 mM) at 37° C. for 15 h. Cells were lysed by lysis buffer (1% NP-40, 25 mM Tris, 150 mM NaCl, 3 mM KCl, pH 7.4, 1×EDTA-free protease inhibitor cocktail from Roche) and then incubated on ice for 15 min. Following incubation, the samples were spun at 18,000×g for 15 min. The supernatants were collected, and protein concentrations were determined by bicinchoninic acid protein assay kit (Pierce). For each sample, 50 μg total lysate was loaded and separated on 4-12% NuPAGE (Invitrogen). After transferring proteins onto the PVDF membrane (Millipore), membrane click reaction was performed and labeling signal was analyzed by chemiluminescence detector.

For confocal microscopy analysis, sialidase transfectant 293T cells were seeded onto four-well chamber slices (3×10$^5$/mL per well), and were cultivated in penicillin/streptomycin-containing 10% FBS/DMEM. Growth medium was supplemented with PDSFA (0.2 mM) and cultured for 15 h. Cells were fixed with 4% paraformaldehyde for 15 min, permeabilized in 0.5% TritonX-100 for 10 min at room temperature, and subjected to the probe labeling reaction consisting 0.1 mM azide-biotin probe/0.1 mM tris-triazole ligand/1 mM CuSO$_4$/2 mM sodium ascorbate, in PBS, at room temperature for 1 h. Subsequently, the fixed and labeled cells were rinsed with PBS and stained with Dylight 488-conjugated streptavidin (2.5 μg/mL in 0.5% BSA/PBS) at room temperature for 30 min. Recombinant sialidases were detected by Alexa Fluor 594-conjugated anti-FLAG antibody (5 ug/ml in 0.5% BSA/PBS). Fluorescent images were captured by Leica TCS-SP5-MP-SMD.

Example 13: Sialidase Activity Assays

Fibroblasts (from D551, GM02921, and GM02922) were fed with PDFSA (0.2 mM) at 37° C. for 15 h. Fibroblasts were lysed by lysis buffer (1% NP-40, 100 mM NaOAc, 150 mM NaCl, 3 mM KCl, pH 4.5, 1×EDTA-free protease inhibitor cocktail from Roche) and then incubated on ice for 15 min. Following incubation, the samples were spun at 18,000×g for 15 min. The supernatants were collected. One hundred g total lysates in a total volume of 0.1 mL were incubated with MUNANA (0.1 mM) at 37° C. for 1 h. The reaction was terminated with 0.1 mL of 0.85 M glycine-carbonate buffer (pH 9.3), and kept at 4° C. before reading fluorescence. Fluorescence was determined on a fluorometer with excitation at 365 nm and emission at 450 nm.

Example 14: Visualization of Flu Infected Cells Using DFSA

The human kidney cell line, MDCK, were seeded onto six-well plates (3×10$^5$/2 ml per well) containing glass coverslips, and were cultivated in 2% FCS/DMEM, and 1% P/S antibiotic-antimycotic. Cells were infected with 0.03 multiplicity of infection (MOI) of flu virus for 20 h at 35° C. and treated with 30 μM of DFSA for 1 h at 35° C. Cells on coverslips were fixed with methanol for 3 min, then permeabilized with 0.05% triton-X100 in PBS for 1 min. Cells were subjected to the probe labeling reaction (0.1 mM azide-biotin probe, 0.1 mM tris-triazole ligand, 1 mM CuSO$_4$, 2 mM sodium ascorbate in PBS) at room temperature for 30 min. Subsequently, the fixed and labeled cells were rinsed with PBS and stained with anti-NP monoclonal antibody (500 fold dilution in PBS), streptavidin-DyLight 488 (2 μg/mL in 5% BSA/PBS), and 0.6 μg/mL of Alexa Fluor® 594 labeled Goat Anti-Mouse IgG (Invitrogen cat#A11020) at room temperature for 30 min. DAPI (10 μg/mL in PBS) was used to stain nuclei. Fluorescent images were captured by Leica upright microscope DM 6000B.

Example 15: Quick Detection of OS Susceptibility of Influenza Viruses on Membrane Polyvinylidene fluoride (PVDF) membrane mounted on Bio-Dot SF of Bio-Rad Inc. (Bio-Rad, CA, USA) was wetted with methanol. Influenza viral samples that were previously treated for 1 h with either 30 μM DFSA or 30 μM DFSA plus OS were introduced to neighboring slots by suction. The membranes were blotted using PBS with 3% BSA and then PBS with streptavidin 5 μg/mL to lower the endogenous biotin noise. Following the click reaction and then incubated with horseradish peroxidase conjugated streptavidin from KPL (Gaithersburg, Md., USA) according to the manufacturer's instruction. After additional washing using PBS with 0.05% tween-20, horseradish peroxidase substrate ECL (Calbiochem®) was added for chemiluminescent development.

Example 16: Mass Spectrometric Analyses of Tryptic Peptides of DFSA-Labeled Sialidases DFSA-labeled sialidases (5 μg) were dissolved in 100 mM ammonium bicarbonate and 8 mM dithiothreitol, and incubated at 65° C. for 1 h. To the protein solutions were added 4 μL of 40 mM iodoacetamide, and incubated in dark at room temperature for 1 h. The protein solutions were added 1 μL of 40 mM dithiothreitol at room temperature for 1 h. The sialidases samples were treated with trypsin at neutral pH for 17 h, heated to inactivate trypsin, and dried for MS analysis.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

REFERENCES

G. C. Adam, E. J. Sorensen, B. F. Cravatt, *Nat. Biotechnol.* 2002, 20, 805-809. Proteomic profiling of mechanistically distinct enzyme classes using a common chemotype.

T. Angata, A. Varki, *Chem. Rev.* 2002, 102, 439-469. Chemical diversity in the sialic acids and related alpha-keto acids: an evolutionary perspective.

A. Bigi, L. Morosi, C. Pozzi, M. Forcella, G. Tettamanti, B. Venerando, E. Monti, P. Fusi, *Glycobiology* 2010, 20, 148-157. Human sialidase NEU4 long and short are extrinsic proteins bound to outer mitochondrial membrane and the endoplasmic reticulum, respectively.

H. B. Bosmann, T. C. Hall, *Proc. Natl. Acad. Sci. USA* 1974, 71, 1833-1837. Enzyme activity in invasive tumors of human breast and colon.

S. Buchini, A. Buschiazzo, S. G. Withers, *Angew. Chem. Int. Ed.* 2008, 47, 2700-2703. A new generation of specific *Trypanosoma cruzi* trans-sialidase inhibitors.

M. J. Evans, B. F. Cravatt, *Chem. Rev.* 2006, 106, 3279-3301. Mechanism-based profiling of enzyme families.

D. Greenbaum, A. Baruch, L. Hayrapetian, Z. Darula, A. Burlingame, K. F. Medzihradszky, M. Bogyo, *Mol. Cell. Proteomics* 2002, 1, 60-68. Chemical approaches for functionally probing the proteome.

G. T. van der Horst, G. M. Mancini, R. Brossmer, U. Rose, F. W. Verheijen, *J. Biol. Chem.* 1990, 265, 10801-10804. Photoaffinity labeling of a bacterial sialidase with an aryl azide derivative of sialic acid.

T. L. Hsu, S. R. Hanson, K. Kishikawa, S. K. Wang, M. Sawa, C. H. Wong, *Proc. Natl. Acad. Sci. USA* 2007, 104, 2614-2619. Alkynyl sugar analogs for the labeling and visualization of glycoconjugates in cells.

C. L. Jacobs, K. J. Yarema, L. K. Mahal, D. A. Nauman, N. W. Charters, C. R. Bertozzi, *Methods Enzymol.* 2000, 327, 260-275. Metabolic labeling of glycoproteins with chemical tags through unnatural sialic acid biosynthesis.

K. A. Kalesh, L. P. Tan, K. Lu, L. Gao, J. Wang, S. Q. Yao, *Chem. Commun.* 2010, 46, 589-591. Peptide-based activity-based probes (ABPs) for target-specific profiling of protein tyrosine phosphatases (PTPs).

R. Kannappan, M. Ando, K. Furuhata, Y. Uda, *Biol. Pharm. Bull.* 2008, 31, 352-356. Photoaffinity labeling of sialidase with a biotin-conjugated phenylaminodiazirine derivative of 2,3-didehydro-2-deoxy-N-acetylneuraminic acid.

D. Kidd, Y. Liu, B. F. Cravatt, *Biochemistry* 2001, 40, 4005-4015. Profiling serine hydrolase activities in complex proteomes.

H. C. Kolb, K. B. Sharpless, *Drug Discov Today* 2003, 8, 1128-1137. The growing impact of click chemistry on drug discovery.

Y. Liu, M. P. Patricelli, B. F. Cravatt, *Proc. Natl. Acad. Sci. USA* 1999, 96, 14694-14699. Activity-based protein profiling: the serine hydrolases.

C. P. Lu, C. T. Ren, Y. N. Lai, S. H. Wu, W. M. Wang, J. Y. Chen, L. C. Lo, *Angew. Chem. Int. Ed.* 2005, 44, 6888-6892. Design of a mechanism-based probe for neuraminidase to capture influenza viruses.

T. Miyagi, T. Wada, K. Yamaguchi, K. Hata, *Glycoconj. J.* 2004, 20, 189-198. Sialidase and malignancy: a minireview.

T. Miyagi, *Proc. Jpn. Acad. Ser. B Phys Biol. Sci.* 2008, 84, 407-418. Aberrant expression of sialidase and cancer progression.

T. Miyagi, T. Wada, K. Yamaguchi, K. Hata, K. Shiozaki, *J. Biochem.* 2008, 144, 279-285. Plasma membrane-associated sialidase as a crucial regulator of transmembrane signaling.

T. Miyagi, K. Yamaguchi, *Glycobiology* 2012, 22, 880-896. Mammalian sialidases: Physiological and pathological roles in cellular functions.

MMWR. *Morb. Mortal. Wkly. Rep.* 2008, 57, 692-697. Influenza activity—United States and worldwide, 2007-08 season.

E. Monti, E. Bonten, A. D'Azzo, R. Bresciani, B. Venerando, G. Borsani, R. Schauer, G. Tettamanti, *Adv. Carbohydr. Chem. Biochem.* 2010, 64, 403-479. Sialidases in vertebrates: a family of enzymes tailored for several cell functions.

M. P. Patricelli, A. K. Szardenings, M. Liyanage, T. K. Nomanbhoy, M. Wu, H. Weissig, A. Aban, D. Chun, S. Tanner, J. W. Kozarich, *Biochemistry* 2007, 46, 350-358. Functional interrogation of the kinome using nucleotide acyl phosphates.

A. V. Pshezhetsky, M. Potier, *J. Biol. Chem.* 1996, 271, 28359-28365. Association of N-acetylgalactosamine-6-sulfate sulfatase with the multienzyme lysosomal complex of beta-galactosidase, cathepsin A, and neuraminidase. Possible implication for intralysosomal catabolism of keratan sulfate.

V. V. Rostovtsev, L. G. Green, V. V. Fokin, K. B. Sharpless, *Angew. Chem. Int. Ed.* 2002, 41, 2596-2599. A stepwise Huisgen cycloaddition process: copper(I)-catalyzed regioselective "ligation" of azides and terminal alkynes.

R. K. Y. M. Saito, *Biochemistry and function of sialidases*, Plenum Press: New York, 1995.

C. M. Salisbury, B. F. Cravatt, *Proc. Natl. Acad. Sci. USA* 2007, 104, 1171-1176. Activity-based probes for proteomic profiling of histone deacetylase complexes.

A. K. Sarkar, T. A. Fritz, W. H. Taylor, J. D. Esko, *Proc. Natl. Acad. Sci. USA* 1995, 92, 3323-3327. Disaccharide uptake and priming in animal cells: inhibition of sialyl Lewis X by acetylated Gal beta 1→4 GlcNAc beta-O-naphthalenemethanol.

C. L. Schengrund, D. S. Jensen, A. Rosenberg, *J. Biol. Chem.* 1972, 247, 2742-2746. Localization of sialidase in the plasma membrane of rat liver cells.

E. Severi, D. W. Hood, G. H. Thomas, *Microbiology* 2007, 153, 2817-2822. Sialic acid utilization by bacterial pathogens.

V. Seyrantepe, K. Landry, S. Trudel, J. A. Hassan, C. R. Morales, A. V. Pshezhetsky, *J. Biol. Chem.* 2004, 279, 37021-37029. Neu4, a novel human lysosomal lumen sialidase, confers normal phenotype to sialidosis and galactosialidosis cells.

T. G. Sheu, V. M. Deyde, M. Okomo-Adhiambo, R. J. Garten, X. Xu, R. A. Bright, E. N. Butler, T. R. Wallis, A. I. Klimov, L. V. Gubareva, *Antimicrob. Agents Chemother.* 2008, 52, 3284-3292. Surveillance for neuraminidase inhibitor resistance among human influenza A and B viruses circulating worldwide from 2004 to 2008.

S. A. Sieber, S. Niessen, H. S. Hoover, B. F. Cravatt, *Nat. Chem. Biol.* 2006, 2, 274-281. Proteomic profiling of metalloprotease activities with cocktails of active-site probes.

K. A. Stubbs, A. Scaffidi, A. W. Debowski, B. L. Mark, R. V. Stick, D. J. Vocadlo, *J. Am. Chem. Soc.* 2008, 130, 327-335. Synthesis and use of mechanism-based protein-profiling probes for retaining beta-D-glucosaminidases facilitate identification of *Pseudomonas aeruginosa* NagZ.

G. H. Thomas, Disorders of Glycoprotein Degradation: α-Mannosidosis, β-Mannosidosis, Fucosidosis, and Sialidosis, 8 ed., McGraw-Hill: New York, 2001.

C. S. Tsai, Y. K. Li, L. C. Lo, *Org. Lett.* 2002, 4, 3607-3610. Design and synthesis of activity probes for glycosidases.

A. Varki, *Nature* 2007, 446, 1023-1029. Glycan-based interactions involving vertebrate sialic-acid-recognizing proteins.

M. V. Vinogradova, L. Michaud, A. V. Mezentsev, K. E. Lukong, M. El-Alfy, C. R. Morales, M. Potier, A. V. Pshezhetsky, *Biochem. J.* 1998, 330, 641-650. Molecular mechanism of lysosomal sialidase deficiency in galactosialidosis involves its rapid degradation.

D. J. Vocadlo, C. R. Bertozzi, *Angew. Chem. Int. Ed.* 2004, 43, 5338-5342. A strategy for functional proteomic analysis of glycosidase activity from cell lysates.

T. Wada, K. Hata, K. Yamaguchi, K. Shiozaki, K. Koseki, S. Moriya, T. Miyagi, *Oncogene* 2007, 26, 2483-2490. A crucial role of plasma membrane-associated sialidase in the survival of human cancer cells.

C. Walls, B. Zhou, Z. Y. Zhang, *Methods Mol. Biol.* 2009, 519, 417-429. Activity-based protein profiling of protein tyrosine phosphatases.

A. G. Watts, I. Damager, M. L. Amaya, A. Buschiazzo, P. Alzari, A. C. Frasch, S. G. Withers, *J. Am. Chem. Soc.* 2003, 125, 7532-7533. *Trypanosoma cruzi* trans-sialidase operates through a covalent sialyl-enzyme intermediate: tyrosine is the catalytic nucleophile.

M. D. Witte, W. W. Kallemeijn, J. Aten, K. Y. Li, A. Strijland, W. E. Donker-Koopman, A. M. van den Nieuwendijk, B. Bleijlevens, G. Kramer, B. I. Florea, B. Hooibrink, C. E. Hollak, R. Ottenhoff, R. G. Boot, G. A. van der Marel, H. S. Overkleeft, J. M. Aerts, *Nat. Chem. Biol.* 2010, 6, 907-913. Ultrasensitive in situ visualization of active glucocerebrosidase molecules.

K. Yamaguchi, K. Hata, K. Koseki, K. Shiozaki, H. Akita, T. Wada, S. Moriya, T. Miyagi, *Biochem. J.* 2005, 390, 85-93. Evidence for mitochondrial localization of a novel human sialidase (NEU4).

All publications and patent applications cited in this specification are herein incorporated by reference as if each individual publication or patent application was specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A compound of formula (I):

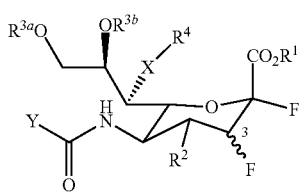

(I)

or a salt thereof,
wherein
F atom at the C3-position is axial or equatorial;
$R^1$ is H or $C_{1-6}$ alkyl;
$R^2$ is $OR^{2O}$, $N_3$, $N(R^{2N})_2$, or $-NH(C=NH)NH_2$;
each instance of $R^{2O}$ is independently hydrogen, $C_{1-6}$ alkyl, acyl, or a hydroxyl protecting group;
each instance of $R^{2N}$ is independently hydrogen, $C_{1-6}$ alkyl, acyl, or an amine protecting group;
each instance of $R^{3a}$ and $R^{3b}$ is independently hydrogen, $-C(=O)-R^{3r}$, or a hydroxyl protecting group;
each instance of $R^{3r}$ is $C_{1-6}$ alkyl, aryl, heteroaryl, heterocyclyl, alkylaryl, alkylheteroaryl, or alkylheterocyclyl;
X is selected from the group consisting of $-O-$, $-O(C=O)-$, $-NH-$, $-NH(C=O)-$, $-(C=O)NH-$, $-O(C=O)NH-$, $-O(C=S)NH-$, $-NH(C=O)NH-$, and $-NH(C=S)NH-$;
$R^4$ is H, $C_{1-6}$ alkyl, or -L-Z;
Y is $CF_3$, $C_{1-6}$ alkyl or -L-Z;
each instance of L is independently selected from the group consisting of $-(CH_2)_n-$, $-(CH_2)_nC=O-$, $-(CH_2)_nNH-$, $-(C=O)(CH_2)_n-$, $-(CH_2)_nNH(C=O)-$, $-(C=O)(CH_2)_nNH(C=O)-$, $-(CH_2)_nSCH_2(C=O)-$, and $-(CH_2CH_2O)_n-$;
each instance of n is an integer from 1 to 8, inclusive;
each instance of Z is alkynyl, alkenyl, halogen, $N(R^N)_2$, $OR^O$, $SR^S$, or $CO_2R^O$;
each instance of $R^N$ is independently hydrogen, $C_{1-6}$ alkyl, acyl, or an amine protecting group;
each instance of $R^O$ is independently hydrogen, $C_{1-6}$ alkyl, acyl, or a hydroxyl protecting group;

each instance of $R^S$ is independently hydrogen, $C_{1-6}$ alkyl, or a thiol protecting group;

provided that the compound is not of the formula

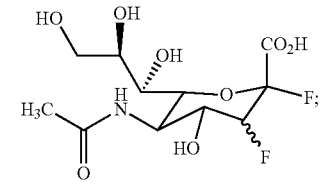

provided that when $R^4$ is -L-Z, Y is $C_{1-6}$ alkyl; and
provided that when Y is -L-Z, $R^4$ is H or $C_{1-6}$ alkyl.

2. The compound of claim 1 of formula (II-a):

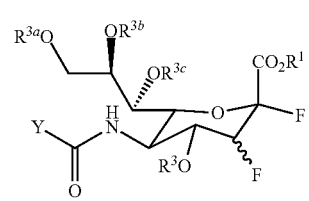

(II-a)

or a salt thereof,
wherein $R^{3c}$ is independently hydrogen, $C_{1-6}$ alkyl, acyl, or a hydroxyl protecting group.

3. The compound of claim 2 of formula (II-b):

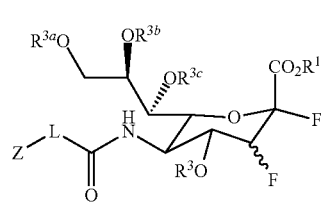

(II-b)

or a salt thereof.

4. The compound of claim 3, having a formula (II-b1):

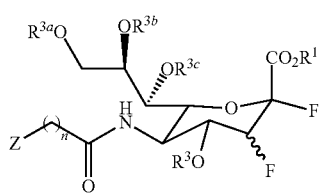

(II-b1)

or a salt thereof.

5. The compound of claim 4, having the formula (II-b2):

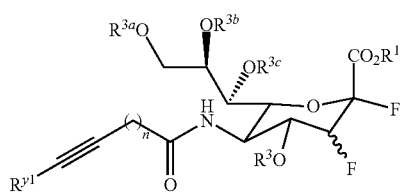

(II-b2)

wherein $R^{y1}$ is hydrogen, halogen, or $C_{1-6}$ alkyl, or a salt thereof.

6. The compound of claim 1 of formula (II-c):

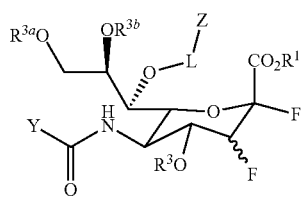

(II-c)

or a salt thereof.

7. The compound of claim 6, having a formula selected from (II-c1) and (II-C2):

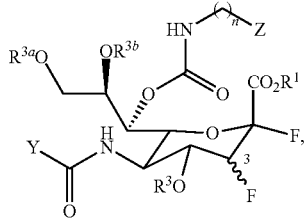

(II-c1)

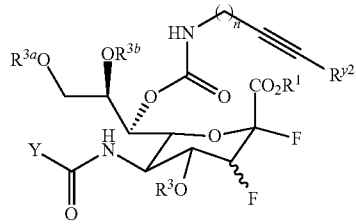

(II-c2)

wherein $R^{y2}$ is hydrogen or $C_{1-6}$ alkyl, or a salt thereof.

8. The compound of claim 6, wherein Y is $C_{1-6}$ alkyl.

9. The compound of claim 8, wherein Y is methyl or $CF_3$.

10. The compound of claim 1, wherein $R^1$ is H or methyl.

11. The compound of claim 1, wherein the F atom at the C3-position is axial.

12. The compound of claim 1, wherein the F atom at the C3-position is equatorial.

13. The compound of claim 1, wherein $R^{3a}$ is —C(═O)—$R^{3r}$, wherein $R^{3r}$ is $C_{1-6}$ alkyl or aryl.

14. The compound of claim 1, wherein $R^{3a}$ is benzoyl.

15. The compound of claim 1, wherein $R^{3a}$ is $CH_3CO$—, $C_2H_5CO$—, $C_3H_7CO$—, t-BuCO—, $CF_3CO$—, $PhCH_2CO$—, or $C_6H_5CO$—.

16. The compound of claim 1, wherein the compound is one of the following formulae:

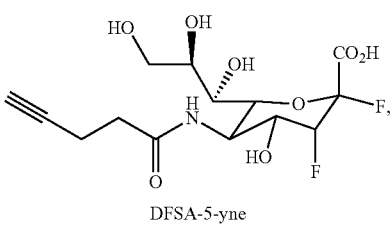

(III)

DFSA-5-yne

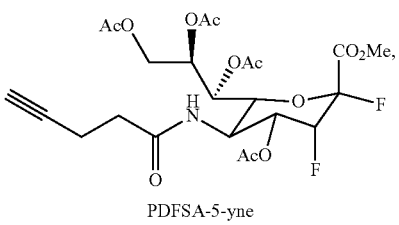

(IV)

PDFSA-5-yne

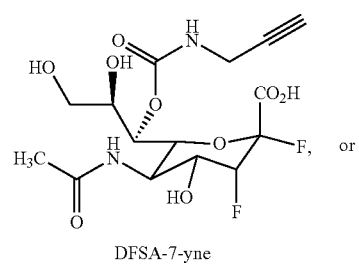

(VI)

DFSA-7-yne

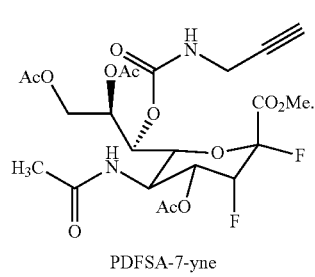

(VII)

PDFSA-7-yne

* * * * *

SEQUENCE LISTING

<160> NUMBER OF SEQ ID NOS: 7

<210> SEQ ID NO 1
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

Phe Ala Tyr Asn Ser Ile Gln Glu Ile Gly Asn Gly Glu Tyr Gly Ile

-continued

```
                1               5                   10                  15
Ile Tyr Glu His Thr Glu Lys Gly Gln Asn Ala Tyr Thr Ile Ser Phe
                20                  25                  30
Arg

<210> SEQ ID NO 2
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Tyr His Tyr Asp Ile Asp Ile Pro Ser Tyr Gly Tyr Ala Tyr Ser Ala
1               5                   10                  15
Ile Thr Glu Ile Pro Asn His His Ile Gly Val Ile Phe Glu Lys
                20                  25                  30

<210> SEQ ID NO 3
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Tyr His His Asp Val Asp Tyr Ser Asn Tyr Gly Tyr Ser Tyr Ser Thr
1               5                   10                  15
Ile Thr Glu Ile Pro Asn His Glu Ile Gly Ile Met Phe Glu Lys
                20                  25                  30

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ile Val Lys Pro Gly Tyr Tyr Ala Tyr Ser Cys Ile Thr Glu
1               5                   10

<210> SEQ ID NO 5
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Thr Val Lys Pro Gly Ser Phe Ala Tyr Ser Cys Ile Thr Glu Ile Pro
1               5                   10                  15
Asp Gly Asn Ile Gly Ile Phe Tyr Glu Gly Glu Gly Ala Gly Arg
                20                  25                  30

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 6

Ile Gly Gly Gly Tyr Ser Cys Ile Ser Phe Lys
1               5                   10

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 7

His His His His His His
1               5